(12) United States Patent
Wu et al.

(10) Patent No.: US 6,262,030 B1
(45) Date of Patent: Jul. 17, 2001

(54) ERYTHROMYCIN DERIVATIVES

(75) Inventors: Yong-Jin Wu; Wei-Guo Su, both of East Lyme, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/432,500

(22) Filed: Nov. 2, 1999

Related U.S. Application Data

(60) Provisional application No. 60/106,820, filed on Nov. 3, 1998.

(51) Int. Cl.[7] .................... C07H 17/08; A61K 31/70
(52) U.S. Cl. ................................ 514/29; 536/7.4
(58) Field of Search .................. 536/7.4, 7.2; 574/29

(56) References Cited

FOREIGN PATENT DOCUMENTS

WO 98/58917   12/1998   (WO) .
WO 99/00124    1/1999   (WO) .

*Primary Examiner*—Elli Peselev
(74) *Attorney, Agent, or Firm*—Peter C. Richardson; Paul H. Ginsburg; Bryan C. Zielinski

(57) ABSTRACT

The invention relates to the compounds of the formula 1

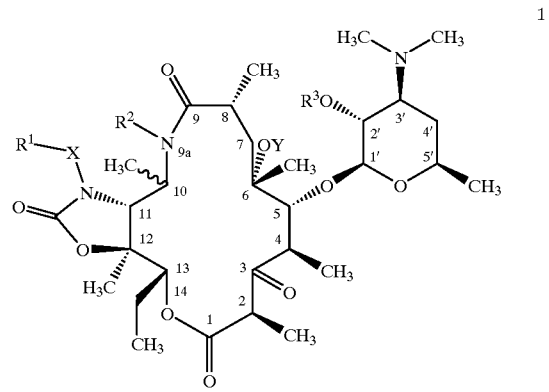

and to pharmaceutically acceptable salts thereof, wherein $R^1$, $R^2$, $R^3$, X and Y are as defined herein. The invention also relates to pharmaceutical compositions containing the compounds of formula 1, methods of using said compounds of formula 1 in the treatment of infections, and methods of preparing said the compounds of formula 1.

30 Claims, No Drawings

ERYTHROMYCIN DERIVATIVES

Priority is claimed from United States Provisional Patent Application Number 60/106,820, filed Nov. 3, 1998.

BACKGROUND OF THE INVENTION

This invention relates to novel erythromycin A derivatives that are useful as antibacterial agents and antiprotozoa agents and for other applications (e.g., anticancer, atherosclerosis, gastric motility reduction, etc.) in mammals, including man, as well as in fish and birds. This invention also relates to pharmaceutical compositions containing the novel compounds and to methods of treating bacterial infections and protozoa infections and in mammals, fish and birds by administering the novel compounds to mammals, fish and birds requiring such treatment.

Macrolide antibiotics are known to be useful in the treatment of a broad spectrum of bacterial infections and protozoa infections in mammals, fish and birds. Such antibiotics include various derivatives of erythromycin A such as azithromycin which is commercially available and is referred to in U.S. Pat. Nos. 4,474,768 and 4,517,359, both of which are incorporated herein by reference in their entirety. Additional macrolides are referred to in U.S. patent application Ser. No. 60/049,349, filed Jun. 11, 1997 (Yong-Jin Wu), International Application No. PCT/IB98/00741, filed May 15, 1998 (Yong-Jin Wu), U.S. patent application Ser. No. 60/046,150, filed May 9, 1997 (Yong-Jin Wu), U.S. patent application Ser. No. 60/063,676, filed Oct. 29, 1997 (Yong-Jin Wu), U.S. application Ser. No. 60/063,161, filed Oct. 29, 1997 (Yong-Jin Wu), U.S. application Ser. No. 60/054,866, filed Aug. 6, 1997 (Hiroko Masamune, Yong-Jin Wu, Takushi Kaneko and Paul R. McGuirk), U.S. application Ser. No. 60/049,980, filed Jun. 11, 1997 (Brian S. Bronk, Henry Cheng, E. A. Glaser, Michael A. Letavic, Takushi Kaneko and Bingwei V. Yang), U.S. application Ser. No. 60/049,348, filed Jun. 11, 1997 (Brian S. Bronk, Henry Cheng, E. A. Glaser, Michael A. Letavic, Takushi Kaneko and Bingwei V. Yang), International Application No. PCT/GB97/01810 filed Jul. 4, 1997 (Peter Francis Leadlay, James Staunton, Jesus Cortes and Michael Stephen Pacey), International Application No. PCT/GB97/01819 filed Jul. 4, 1997 (Peter Francis Leadlay, James Staunton, and Jesus Cortes), U.S. application Ser. No. 60/070,343, filed Jan. 2, 1998 (Dirlam), U.S. application Ser. No. 60/070,358, filed Jan. 2, 1998 (Yong-Jin Wu) and U.S. application Ser. No. 60/097,075, filed Aug. 19, 1998 (Hengmiao Cheng, Michael A. Letavic, Carl B. Ziegler, Jason K Dutra, Brian S. Bronk), all of which are incorporated herein by reference in their entirety. Like azithromycin and other macrolide antibiotics, the novel macrolide compounds of the present invention possess potent activity against various bacterial infections and protozoa infections as described below.

SUMMARY OF THE INVENTION

The present invention relates to a compound of the formula 1

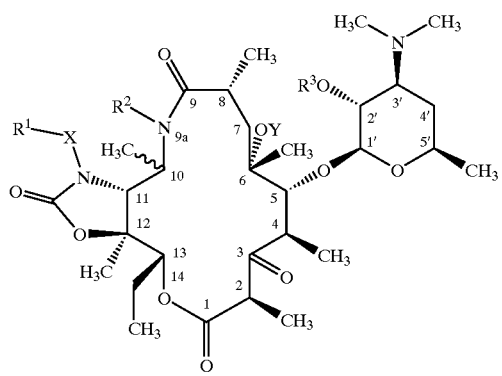

and pharmaceutically acceptable salts thereof, wherein:

X is —O—, —NR$^5$—, or (CR$^5$R$^6$)$_g$, wherein g is 0 or 1 and wherein, when X is —NR$^5$—, R$^5$ and R$^2$ are taken together to form —(CR$^7$R$^8$)—;

or X is taken together with R$^1$ to form —N=CR$^7$R$^8$;

or X and R$^1$ are taken together to form a heterocyclic ring of the formula XI

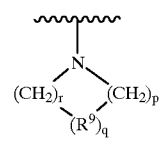

XI wherein in said ring of formula XI, r and p are each independently an integer ranging from 1 to 3, q is 0 or 1, and R$^9$ is —CH$_2$—, O, S, —C(O)—, —C(S)—, —SO$_2$—, —CH=CH—, —CH(OH)CH(OH)—, or —NH—; and wherein the (CH$_2$)$_r$ and (CH$_2$)$_p$ portions of said ring of formula XI are optionally substituted by 1 to 4 substituents and wherein each hydrogen atom of R$^9$ when R$^9$ is —CH$_2$—, —CH=CH—, —CH(OH)CH(OH)—, or —NH is optionally substituted by one substituent, said optional substituents being independently selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, C$_6$–C$_{10}$ aryl, 4–10 membered heterocyclic, —S(O)$_n$R$^{10}$, and —SO$_2$NR$^{10}$R$^{11}$, wherein n is an integer ranging from 0 to 2;

Y is R$^7$ or —(CR$^5$R$^6$)$_m$R$^{12}$, wherein m is an integer ranging from 0 to 6; and R$^5$ and R$^6$ may each independently vary when m is greater than 1;

R$^1$ is H, R$^7$, —C(O)R$^7$, —C(O)R$^{12}$, —C(O)OR$^7$, —C(O)OR$^{12}$, or —(CR$^5$R$^6$)$_m$R$^{12}$, wherein integer ranging from 0 to 6;

R$^2$ is H or C$_1$–C$_{12}$ alkyl, wherein one or two carbons of said alkyl are optionally replaced by a heteroatom selected from O, S and N, and are optionally substituted by 1 to 3 substituents selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, C$_6$–C$_{10}$ aryl, 4–10 membered heterocyclic, —S(O)$_n$R$^{10}$, and —SO$_2$NR$^{10}$R$^{11}$, wherein n is an integer ranging from 0 to 2;

each R$^3$ is independently selected from H, —C(O)R$^{12}$ or C$_1$–C$_{18}$ alkanoyl, wherein in the alkyl portion of said alkanoyl one or two carbons optionally may be replaced by a heteroatom selected from O, S and N;

each $R^5$ and $R^6$ is independently H, halo, or $C_1$–$C_{10}$ alkyl and $R^5$ and $R^6$ may each independently vary when m is greater than 1;

each $R^7$ and $R^8$ is independently selected from H and $C_1$–$C_{18}$ alkyl, wherein one or two carbons of said alkyl are optionally replaced by a heteroatom selected from O, S and N, and are optionally substituted by 1 to 3 substituents selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, $C_6$–$C_{10}$ aryl, 4–10 membered heterocyclic, —S(O)nR10 and —SO$_2$NR$^{10}$R$^{11}$, wherein n is an integer ranging from 0 to 2;

each $R^{10}$ and $R^{11}$ is independently H or $C_1$–$C_{10}$ alkyl; and, $R^{12}$ is a 4–10 membered heterocycyl or $C_6$–$C_{10}$ aryl, wherein said heterocycyl and aryl groups are optionally substituted by 1 to 3 substituents independently selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, $C_6$–$C_{10}$ aryl, 4–10 membered heterocyclic, —S(O)$_n$R$^{10}$, and —SO$_2$NR$^{10}$OR$^{11}$, wherein n is an integer ranging from 0 to 2.

This invention further relates to a compound of the formula 2

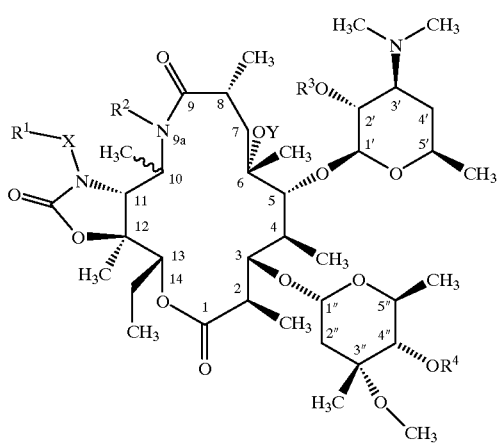

2 and pharmaceutically acceptable salts thereof, wherein:

X is —O—, —NR$^5$—, or (CR$^5$R$^6$)$_g$, wherein g is 0 or 1 and wherein, when X is —NR$^5$—, $R^5$ $R^2$ are taken together to form —(CR$^7$R$^8$)—;

or X is taken together with $R^1$ to form —N=CR$^7$R$^8$;

or X and $R^1$ are taken together to form a heterocyclic ring of the formula XI

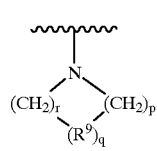

XI wherein in said ring of formula XI, r and p are each independently an integer ranging from 1 to 3, q is 0 or 1, and $R^9$ is —CH$_2$—, O, S, —C(O)—, —C(S)—, —SO$_2$—, —CH=CH—, —CH(OH)CH(OH)—, or —NH—; and wherein the (CH$_2$)$_r$ and (CH$_2$)$_p$ portions of said ring of formula XI are optionally substituted by 1 to 4 substituents and wherein each hydrogen atom of $R^9$ when $R^9$ is —CH$_2$—, —CH=CH—, —CH(OH)CH(OH)—, or —NH is optionally substituted by one substituent, said optional substituents being indepently selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, $C_6$–$C_{10}$ aryl, 4–10 membered heterocyclic, —S(O)$_n$R$^{10}$, and —SO$_2$NR$^{10}$R$^{11}$, wherein n is an integer ranging from 0 to 2;

$R^1$ is H, $R^7$, —C(O)R$^7$, —C(O)R$^{12}$, —C(O)OR$^7$, —C(O)OR$^{12}$, or —(CR$^5$R$^6$)$_m$R$^{12}$, wherein m is an interger ranging from 0 to 6;

$R^2$ is H or $C_1$–$C_{12}$ alkyl, wherein one or two carbons of said alkyl are optionally replaced by a heteroatom selected from O, S and N, and are optionally substituted by 1 to 3 substituents selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, $C_6$–$C_{10}$ aryl, 4–10 membered heterocyclic, —S(O)$_n$R$^{10}$, and —SO$_2$NR$^{10}$R$^{11}$, wherein n is an integer ranging from 0 to 2;

each $R^3$ and $R^4$ is independently selected from H, —C(O)R$^{12}$ or $C_1$–$C_{18}$ alkanoyl, wherein in the alkyl portion of said alkanoyl one or two carbons optionally may be replaced by a heteroatom selected from O, S and N;

each $R^5$ and $R^6$ is independently H, halo, or $C_1$–$C_{10}$ alkyl and $R^5$ and $R^6$ may each independently vary when m is greater than 1;

each $R^7$ and $R^8$ is independently selected from H and $C_1$–$C_{18}$ alkyl, wherein one or two carbons of said alkyl are optionally replaced by a heteroatom selected from O, S and N, and are optionally substituted by 1 to 3 substituents selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, $C_6$–$C_{10}$ aryl, 4–10 membered heterocyclic, —S(O)nR10 and —SO$_2$NR$^{10}$R$^{11}$, wherein n is an integer ranging from 0 to 2;

each $R^{10}$ and $R^{11}$ is independently H or $C_1$–$C_{10}$ alkyl;

$R^{12}$ is a 4–10 membered heterocycyl or $C_6$–$C_{10}$ aryl, wherein said heterocycyl and aryl groups are optionally substituted by 1 to 3 substituents independently selected from the group consisting of —C(O)OR$^{10}$, —OR$^{10}$, —C(O)R$^{10}$, halo, nitro, cyano, 4–10 membered heterocyclic, —R$^{10}$, —NR$^{10}$, R$^{11}$—NHC(O)R$^{10}$, —NHC(O)NR$^{10}$R$^{11}$, $C_6$–$C_{10}$ aryl, 4–10 membered heterocyclic, —S(O)$_n$R$^{10}$, and —SO$_2$NR$^{10}$R$^{11}$, wherein n is an integer ranging from 0 to 2; and Y is $R^7$ or —(CR$^5$R$^6$)$_m$R$^{12}$, wherein m is an interger ranging from 0 to 6; and $R^5$ and $R^6$ may each independently vary when m is greater than 1.

This invention further relates to a compound of the formula 3

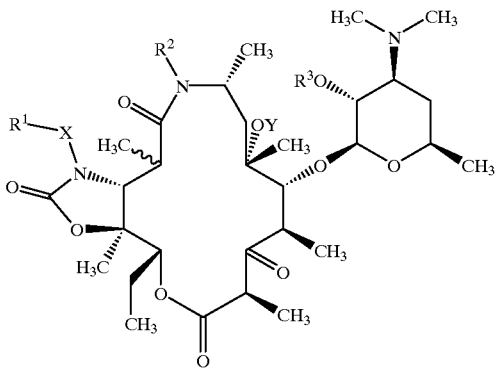

and pharmaceutically acceptable salts thereof, wherein:

X is —O—, —NR$^5$—, or (CR$^5$R$^6$)$_g$, wherein g is 0 or 1; or X is taken together with R$^1$ to form —N=CR$^7$R$^8$; or X and R$^1$ are taken together to form a heterocyclic ring of the formula XI

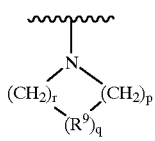

XI wherein in said ring of formula XI, r and p are each independently an integer ranging from 1 to 3, q is 0 or 1, and R$^9$ is —CH$_2$—, O, S, —C(O)—, —C(S)—, —SO$_2$—, —CH=CH—, —CH(OH)CH(OH)—, or —NH—; and wherein the (CH$_2$)$_r$ and (CH$_2$)$_p$ portions of said ring of formula XI are optionally substituted by 1 to 4 substituents and wherein each hydrogen atom of R$^9$ when R$^9$ is —CH$_2$—, —CH=CH—, —CH(OH)CH(OH)—, or —NH is optionally substituted by one substituent, said optional substituents being independently selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, C$_6$–C$_{10}$ aryl, 4–10 membered heterocyclic, —S(O)$_n$R$^{10}$, and —SO$_2$NR$^{10}$R$^{11}$, wherein n is an integer ranging from 0 to 2;

R$^1$ is H, R$^7$, —C(O)R$^7$, —C(O)R$^{12}$, —C(O)OR$^7$, —C(O)OR$^{12}$, or —(CR$^5$R$^6$)$_m$R$^{12}$, wherein m is an interger ranging from 0 to 6;

R$^2$ is H or C$_1$–C$_{12}$ alkyl, wherein one or two carbons of said alkyl are optionally replaced by a heteroatom selected from O, S and N, and are optionally substituted by 1 to 3 substituents selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, C$_6$–C$_{10}$ aryl, 4–10 membered heterocyclic, —S(O)$_n$R$^{10}$, and —SO$_2$NR$^{10}$R$^{11}$, wherein n is an integer ranging from 0 to 2;

each R$^3$ is independently selected from H, —C(O)R$^{12}$ or C$_1$–C$_{18}$ alkanoyl, wherein in the alkyl portion of said alkanoyl one or two carbons optionally may be replaced by a heteroatom selected from O, S and N;

each R$^5$ and R$^6$ is independently H, halo, or C$_1$–C$_{10}$ alkyl and R$^5$ and R$^6$ may each independently vary when m is greater than 1;

each R$^7$ and R$^8$ is independently selected from H and C$_1$–C$_{18}$ alkyl, wherein one or two carbons of said alkyl are optionally replaced by a heteroatom selected from O, S and N, and are optionally substituted by 1 to 3 subsfftuents selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, C$_6$–C$_{10}$ aryl, 4–10 membered heterocyclic, —S(O)nR10 and —SO$_2$NR$^{10}$R$^{11}$, wherein n is an integer ranging from 0 to 2;

each R$^{10}$ and R$^{11}$ is independently H or C$_1$–C$_{10}$ alkyl;

R$^{12}$ is a 4–10 membered heterocycyl or C$_6$–C$_{10}$ aryl, wherein said heterocycyl and aryl groups are optionally substituted by 1 to 3 substituents independently selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, C$_6$–C$_{10}$ aryl, 4–10 membered heterocyclic, —S(O)$_n$R$^{10}$, and —SO$_2$NR$^{10}$R$^{11}$, wherein n is an integer ranging from 0 to 2; and Y is R$^7$ or —(CR$^5$R$^6$)$_m$R$^{12}$, wherein m is an interger ranging from 0 to 6; and R$^5$ and R$^6$ may each independently vary when m is greater than 1.

This invention further relates to a compound of the formula 4

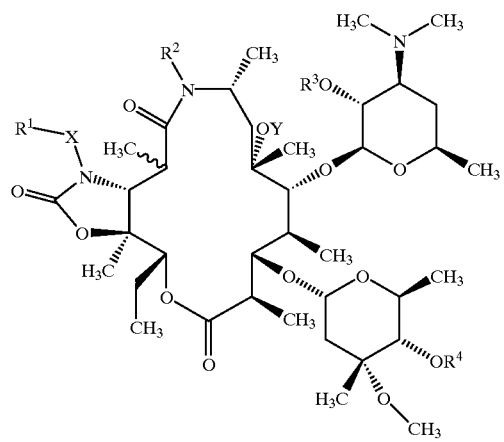

and pharmaceutically acceptable salts thereof, wherein:

X is —O—, —NR$^5$—, or (CR$^5$R$^6$)$_g$, wherein g is 0 or 1; or X is taken together with R$^1$ to form —N=CR$^7$R$^8$; or X and R$^1$ are taken together to form a heterocyclic ring of the formula XI

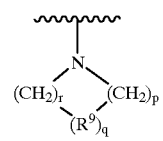

XI wherein in said ring of formula XI, r and p are each independently an integer ranging from 1 to 3, q is 0 or 1, and R$^9$ is —CH$_2$—, O, S, —C(O)—, —C(S)—, —SO$_2$—, —CH=CH—, —CH(OH)CH(OH)—, or —NH—; and wherein the (CH$_2$)$_r$ and (CH$_2$)$_p$ portions of said ring of formula XI are optionally substituted by 1 to 4 substituents and wherein each hydrogen atom of R$^9$ when R$^9$ is —CH$_2$—, —CH=CH—, —CH(OH)CH(OH)—, or —NH is optionally substituted by one substituent, said optional substituents being independently selected from the group consisting of —C(O)OR$^{11}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, C$_6$–C$_{10}$ aryl, 4–10 membered heterocyclic, —S(O)$_n$R$^{10}$, and —SO$_2$NR$^{10}$R$^{11}$, wherein n is an integer ranging from 0 to 2;

R$^1$ is H, R$^7$, —C(O)R$^7$, —C(O)R$^{12}$, —C(O)OR$^{12}$, or —C(O)OR$^7$, —(CR$^5$R$^6$)$_m$R$^{12}$, wherein m is an interger ranging from 0 to 6;

R$^2$ is H or C$_1$–C$_{12}$ alkyl, wherein one or two carbons of said alkyl are optionally replaced by a heteroatom selected from O, S and N, and are optionally substituted by 1 to 3 substituents selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, C$_6$–C$_{10}$ aryl, 4–10 membered heterocyclic, —S(O)$_n$R$^{10}$, and —SO$_2$NR$^{10}$R$^{11}$, wherein n is an integer ranging from 0 to 2;

each R$^3$ and R$^4$ is independently selected from H, —C(O)R$^{12}$ or C$_1$–C$_{18}$ alkanoyl, wherein in the alkyl portion of said alkanoyl one or two carbons optionally may be replaced by a heteroatom selected from O, S and N;

each R$^5$ and R$^6$ is independently H, halo, or C$_1$–C$_{10}$ alkyl and R$^5$ and R$^6$ may each independently vary when m is greater than 1;

each R$^7$ and R$^8$ is independently selected from H and C$_1$–C$_{18}$ alkyl, wherein one or two carbons of said alkyl are optionally replaced by a heteroatom selected from O, S and N, and are optionally substituted by 1 to 3 substituents selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, C$_6$–C$_{10}$ aryl, 4–10 membered heterocyclic, —S(O)$_n$R$^{10}$ and —SO$_2$NR$^{10}$R$^{11}$, wherein n is an integer ranging from 0 to 2;

each R$^{10}$, and R$^{11}$ is independently H or C$_1$–C$_{10}$ alkyl;

R$^{12}$ is a 4–10 membered heterocycyl or C$_6$–C$_{10}$ aryl, wherein said heterocycyl and aryl groups are optionally substituted by 1 to 3 substituents independently selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$OR$^{11}$, C$_6$–C$_{10}$ aryl, 4–10 membered heterocyclic, —S(O)$_n$R$^{10}$, and —SO$_2$NR$^{10}$R$^{11}$, wherein n is an integer ranging from 0 to 2; and Y is R$^7$ or —(CR$^5$R$^6$)$_m$R$^{12}$, wherein m is an interger ranging from 0 to 6; and R$^5$ and R$^6$ may each independently vary when m is greater than 1.

This invention further relates to a compound of the formula 5

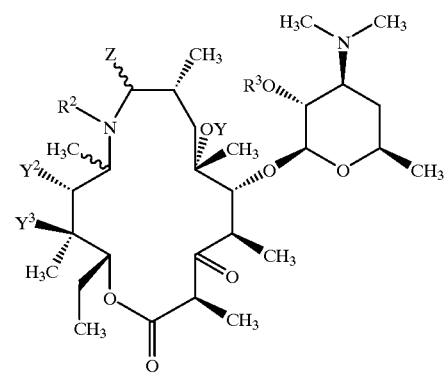

and pharmaceutically acceptable salts thereof, wherein:

X is —O—, —NR$^5$—, or (CR$^5$R$^6$)$_g$, wherein g is 0 or 1 and wherein, when X is —NR$^5$—, R$^5$ and R$^2$ are taken together to form —(CR$^7$R$^8$)—;

or X is taken together with R$^1$ to form —N=CR$^7$R$^8$;

or X and R$^1$ are taken together to form a heterocyclic ring of the formula XI

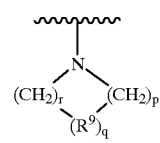

XI wherein in said ring of formula XI, r and p are each independently an integer ranging from 1 to 3, q is 0 or 1, and R$^9$ is —CH$_2$—, O, S, —C(O)—, —C(S)—, —SO$_2$—, —CH=CH—, —CH(OH)CH(OH)—, or —NH—; and wherein the (CH$_2$)$_r$ and (CH$_2$)$_p$ portions of said ring of formula XI are optionally substituted by 1 to 4 substituents and wherein each hydrogen atom of R$^9$ when R$^9$ is —CH$_2$—, —CH=CH—, —CH(OH)CH(OH)—, or —NH is optionally substituted by one substituent, said optional substituents being independently selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, C$_6$–C$_{10}$ aryl, 4–10 membered heterocyclic, —S(O)$_n$R$^{10}$, and —SO$_2$NR$^{10}$R$^{11}$, wherein n is an integer ranging from 0 to 2;

R$^1$ is H, R$^7$, —C(O)R$^7$, —C(O)R$^{12}$, —C(O)OR$^7$, —C(O)OR$^{12}$, or —(CR$^5$R$^6$)$_m$R$^{12}$, wherein m is an interger ranging from 0 to 6;

R$^2$ is H or C$_1$–C$_{18}$ alkyl, wherein one or two carbons of said alkyl are optionally replaced by a heteroatom selected from O, S and N(R$^5$), and are optionally substituted by 1 to 3 substituents selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, C$_6$–C$_{10}$ aryl, 4–10 membered heterocyclic, —S(O)$_n$R$^{10}$, and —SO$_2$NR$^{10}$R$^{11}$, wherein n is an integer ranging from 0 to 2;

each R$^3$ is independently selected from H, —C(O)R$^{12}$ or C$_1$–C$_{18}$ alkanoyl, wherein in the alkyl portion of said alkanoyl one or two carbons optionally may be replaced by a heteroatom selected from O, S and N;

each $R^5$ and $R^6$ is independently H, halo, or $C_1$–$C_{10}$ alkyl and $R^5$ and $R^6$ may each independently vary when m is greater than 1;

each $R^7$ and $R^8$ is independently selected from H and $C_1$–$C_{18}$ alkyl, wherein one or two carbons of said alkyl are optionally replaced by a heteroatom selected from O, S and N, and are optionally substituted by 1 to 3 substituents selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, $C_6$–$C_{10}$ aryl, 4–10 membered heterocyclic, —S(O)nR10 and —SO$_2$NR$^{10}$R$^{11}$, wherein n is an integer ranging from 0 to 2;

each $R^{10}$, $R^{11}$ and Z is independently H or $C_1$–$C_{10}$ alkyl; wherein one or two carbons of said alkyl are optionally replaced by a heteroatom selected from O, S and N, and are optionally substituted by 1 to 3 substituents selected from the group consisting of —C(O)OR$^{13}$, —OR$^{13}$, —C(O)R$^{13}$, halo, nitro, cyano, 4–10 membered heterocyclic, —R$^{13}$, —NR$^{13}$R$^{14}$, —NHC(O)R$^{13}$, —NHC(O)NR$^{13}$R$^{14}$, $C_1$–$C_{10}$ aryl, 4–10 membered heterocyclic, —S(O)$_n$R$^{13}$ wherein n is an integer ranging from 0 to 2, and —SO$_2$NR$^{13}$R$^{14}$;

$R^{12}$ is a 4–10 membered heterocycyl or $C_6$–$C_{10}$ aryl, wherein said heterocycyl and aryl groups are optionally substituted by 1 to 3 substituents independently selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, $C_6$–$C_{10}$ aryl, 4–10 membered heterocyclic, —S(O)$_n$R$^{10}$, and —SO$_2$NR$^{10}$R$^{11}$, wherein n is an integer ranging from 0 to 2;

each $R^{13}$ and $R^{14}$ is independently H or $C_1$–$C_6$ alkyl optionally substituted by 1 to 3 halo groups;

Y is $R^7$ or —(CR$^5$R$^6$)$_m$R$^{12}$, wherein m is an integer ranging from 0 to 6; and $R^5$ and $R^6$ may each independently vary when m is greater than 1;

$Y^2$ is $C_1$–$C_{16}$ alkoxy, —C(O)NH($C_1$–$C_{16}$ alkyl), or —OC(O)NH($C_1$–$C_{16}$ alkyl), wherein the alkyl moieties of the foregoing $Y^2$ groups are optionally substituted by an $R^{12}$ group or 1 to 3 halo groups;

$Y^3$ is hydroxy;

or $Y^2$ and $Y^3$ are taken together to form:

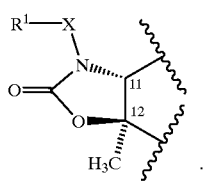

This invention further relates to a compound of the formula 6

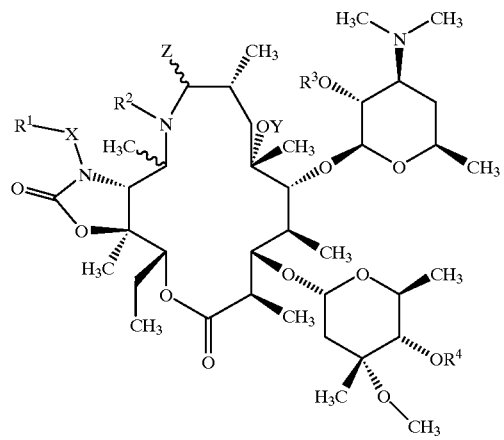

and pharmaceutically acceptable salts thereof, wherein:

X is —O—, —NR$^5$—, or (CR$^5$R$^6$)$_g$, wherein g is 0 or 1 and wherein, when X is —NR$^5$—, R$^5$ and R$^2$ are taken together to formn —(CR$^7$R$^8$)—;

or X is taken together with $R^1$ to form —N=CR$^7$R$^8$;

or X and $R^1$ are taken together to form a heterocyclic ring of the formula XI

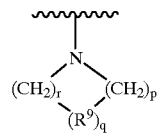

XI wherein in said ring of formula XI, r and p are each indepenently an integer ranging from 1 to 3, q is 0 or 1, and $R^9$ is —CH$_2$—, O, S, —C(O)—, —C(S)—, —SO$_2$—, —CH=CH—, —CH(OH)CH(OH)—, or —NH—; and wherein the (CH$_2$)$_r$ and (CH$_2$)$_p$ portions of said ring of formula XI are optionally substituted by 1 to 4 substituents and wherein each hydrogen atom of $R^9$ when $R^9$ is —CH$_2$—, —CH=CH—, —CH(OH)CH(OH)—, or —NH is optionally substituted by one substituent, said optional substituents being independently selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, $C_6$–$C_{10}$ aryl, 4–10 membered heterocyclic, —S(O)$_n$R$^{10}$, and —SO$_2$NR$^{10}$R$^{11}$, wherein n is an integer ranging from 0 to 2;

$R^1$ is H, $R^7$, —C(O)R$^7$, —C(O)R$^{12}$, C(O)OR$^7$, —C(O)OR$^{12}$, or —(CR$^5$R$^6$)$_m$R$^{12}$, wherein m is an interger ranging from 0 to 6;

$R^2$ is H or $C_1$–$C_{16}$ alkyl, wherein one or two carbons of said alkyl are optionally replaced by a heteroatom selected from O, S and N(R$^5$), and are optionally substituted by 1 to 3 substituents selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, $C_6$–$C_{10}$ aryl, 4–10 membered heterocyclic, —S(O)$_n$R$^{10}$, and —SO$_2$NR$^{10}$R$^{11}$, wherein n is an integer ranging from 0 to 2;

each $R^3$ and $R^4$ is independently selected from H, —C(O)R$^{12}$ or $C_1$–$C_{18}$ alkanoyl, wherein in the alkyl portion of said alkanoyl one or two carbons optionally may be replaced by a heteroatom selected from O, S and N;

each $R^5$ and $R^6$ is independently H, halo, or $C_1$–$C_{10}$ alkyl and $R^5$ and $R^6$ may each independently vary when m is greater than 1;

each $R^7$ and $R^8$ is independently selected from H and $C_1$–$C_{18}$ alkyl, wherein one or two carbons of said alkyl are optionally replaced by a heteroatom selected from O, S and N, and are optionally substituted by 1 to 3 substituents selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, $C_6$–$C_{10}$ aryl, 4–10 membered heterocyclic, —S(O)nR10 and —SO$_2$NR$^{10}$R$^{11}$, wherein n is an integer ranging from 0 to 2;

each $R^{10}$, $R^{11}$ and Z is independently H or $C_1$–$C_{10}$ alkyl; wherein one or two carbons of said alkyl are optionally replaced by a heteroatom selected from O, S and N, and are optionally substituted by 1 to 3 substituents selected from the group consisting of —C(O)OR$^{13}$, —OR$^{13}$, —C(O)R$^{13}$, halo, nitro, cyano, 4–10 membered heterocyclic, —R$^{13}$, —NR$^{13}$R$^{14}$, —NHC(O)R$^{13}$, —NHC(O)NR$^{13}$R$^{14}$, $C_6$–$C_{10}$ aryl, 4–10 membered heterocyclic, —S(O)$_n$R$^{13}$ wherein n is an integer ranging from 0 to 2, and —SO$_2$NR$^{13}$R$^{14}$;

$R^{12}$ is a 4–10 membered heterocycyl or $C_6$–$C_{10}$ aryl, wherein said heterocycyl and aryl groups are optionally substituted by 1 to 3 substituents independently selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, $C_6$–$C_{10}$ aryl, 4–10 membered heterocyclic, —S(O)$_n$R$^{10}$, and —SO$_2$NR$^{10}$R$^{11}$, wherein n is an integer ranging from 0 to 2;

each $R^{13}$ and $R^{14}$ is independently H or $C_1$–$C_6$ alkyl optionally substituted by 1 to 3 halo groups;

Y is $R^7$ or —(CR$^5$R$^6$)$_m$R$^{12}$, wherein m is an interger ranging from 0 to 6; and $R^5$ and $R^6$ may each independently vary when m is greater than 1.

This invention further relates to a compound of the formula 7

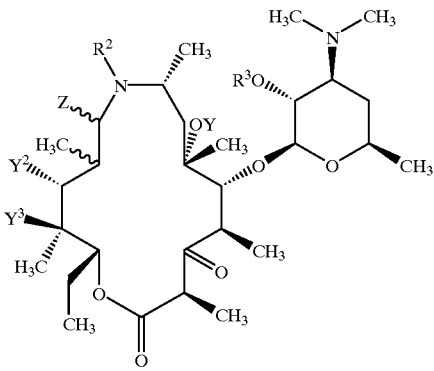

7 and pharmaceutically acceptable salts thereof, wherein:

X is —O—, —NR$^5$—, or (CR$^5$R$^6$)$_g$, wherein g is 0 or 1; or X is taken together with $R^1$ to form —N=CR$^7$R$^8$; or X and $R^1$ are taken together to form a heterocyclic ring of the formula XI

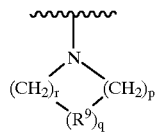

XI wherein in said ring of formula XI, r and p are each independently an integer ranging from 1 to 3, q is 0 or 1, and $R^9$ is —CH$_2$—, O, S, —C(O)—, C(S)—, —SO$_2$—, —CH=CH—, —CH(OH)CH(OH)—, or —NH—; and wherein the (CH$_2$)$_r$ and (CH$_2$)$_p$ portions of said ring of formula XI are optionally substituted by 1 to 4 substituents and wherein each hydrogen atom of $R^9$ when $R^9$ is —CH$_2$—, —CH=CH—, —CH(OH)CH(OH)—, or —NH is optionally substituted by one substituent, said optional substituents being independently selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, $C_6$–$C_{10}$ aryl, 4–10 membered heterocyclic, —S(O)$_n$R$^{10}$, and —SO$_2$NR$^{10}$R$^{11}$, wherein n is an integer ranging from 0 to 2;

$R^1$ is H, $R^7$, —C(O)R$^7$, —C(O)R$^{12}$, —C(O)OR$^7$, —C(O)OR$^{12}$, or —(CR$^5$R$^6$)$_m$R$^{12}$, wherein m is an interger ranging from 0 to 6;

$R^2$ is H or $C_1$–$C_{16}$ alkyl, wherein one or two carbons of said alkyl are optionally replaced by a heteroatom selected from O, S and N, and are optionally substituted by 1 to 3 substituents selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, $C_6$–$C_{10}$ aryl, 4–10 membered heterocyclic, —S(O)$_n$ R$^{10}$, and —SO$_2$NR$^{10}$R$^{11}$, wherein n is an integer ranging from 0 to 2;

each $R^3$ is independently selected from H, —C(O)R$^{12}$ or $C_1$–$C_{18}$ alkanoyl, wherein in the alkyl portion of said alkanoyl one or two carbons optionally may be replaced by a heteroatom selected from O, S and N;

each $R^5$ and $R^6$ is independently H, halo, or $C_1$–$C_{10}$ alkyl and $R^5$ and $R^6$ may each independently vary when m is greater than 1;

each $R^7$ and $R^8$ is independently selected from H and $C_1$–$C_{18}$ alkyl, wherein one or two carbons of said alkyl are optionally replaced by a heteroatom selected from O, S and N, and are optionally substituted by 1 to 3 substituents selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, $C_8$–$C_{10}$ aryl, 4–10 membered heterocyclic, —S(O)nR10 and —SO$_2$NR$^{10}$R$^{11}$, wherein n is an integer ranging from 0 to 2;

each $R^{10}$, $R^{11}$ and Z is independently H or $C_1$–$C_{10}$ alkyl; wherein one or two carbons of said alkyl are optionally replaced by a heteroatom selected from O, S and N, and are optionally substituted by 1 to 3 substituents selected from the group consisting of —C(O)OR$^{13}$, —OR$^{13}$, —C(O)R$^{13}$, halo, nitro, cyano, 4–10 membered heterocyclic, —R$^{13}$, —NR$^{13}$R$^{14}$, —NHC(O)R$^{13}$, —NHC(O)NR$^3$R$^{14}$, $C_6$–$C_{10}$ aryl, 4–10 membered heterocyclic, —S(O)$_n$R$^{13}$ wherein n is an integer ranging from 0 to 2, and —SO$_2$NR$^{13}$R$^{14}$;

$R^{12}$ is a 4–10 membered heterocycyl or $C_6$–$C_{10}$ aryl, wherein said heterocycyl and aryl groups are optionally substituted by 1 to 3 substituents independently selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, C$_6$–C$_{10}$ aryl, 4–10 membered heterocyclic, —S(O)$_n$R$^{10}$, and —SO$_2$NR$^{10}$R$^{11}$, wherein n is an integer ranging from 0 to 2;

each R$^{13}$ and R$^{14}$ is independently H or C$_1$–C$_6$ alkyl optionally substituted by 1 to 3 halo groups;

Y is R$^7$ or —(CR$^5$R$^6$)$_m$R$^{12}$, wherein m is an interger ranging from 0 to 6; and R$^5$ and R$^6$ may each independently vary when m is greater than 1;

Y$^2$ is C$_1$–C$_{18}$ alkoxy, —C(O)NH(C$_1$–C$_{16}$ alkyl), or —OC(O)NH(C$_1$–C$_{16}$ alkyl), wherein the alkyl moieties of the foregoing Y$^2$ groups are optionally substituted by an R$^{12}$ group or 1 to 3 halo groups;

Y$^3$ is hydroxy;

or Y$^2$ and Y$^3$ are taken together to form:

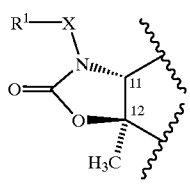

This invention further relates to a compound of the formula 8

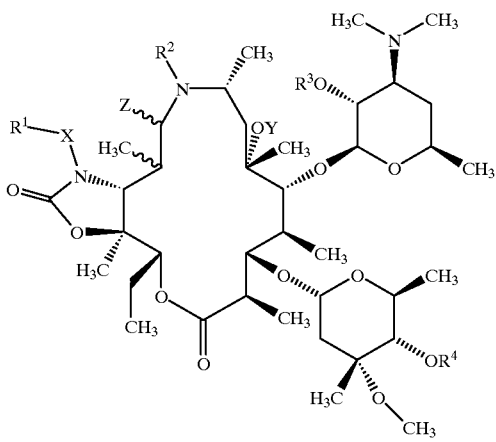

and pharmaceutically acceptable salts thereof, wherein;

X is —O—, —NR$^5$—, or (CR$^5$R$^6$)$_g$, wherein g is 0 or 1;

or X is taken together with R$^1$ to form —N=CR$^7$R$^8$;

or X and R$^1$ are taken together to formn a heterocyclic ring of the formula XI

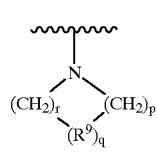

wherein in said ring of formula XI, r and p are each independently an integer ranging from 1 to 3, q is 0 or 1, and R$^9$ is —CH$_2$—, O, S, —C(O)—, —C(S)—, —SO$_2$—, —CH=CH—, —CH(OH)CH(OH)—, or —NH—; and wherein the (CH$_2$)$_r$ and (CH$_2$)$_p$ portions of said ring of formula XI are optionally substiituted by 1 to 4 substituents and wherein each hydrogen atom of R$^9$ when R$^9$ is —CH$_2$—, —CH=CH—, —CH(OH)CH(OH)—, or —NH is optionally substituted by one substituent, said optional substituents being independently selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, C$_6$–C$_{10}$ aryl, 4–10 membered heterocyclic, —S(O)$_n$R$^{10}$, and —SO$_2$NR$^{10}$R$^{11}$, wherein n is an integer ranging from 0 to 2;

R$^1$ is H, R$^7$, —C(O)R$^7$, —C(O)R$^{12}$, —C(O)OR$^7$, —C(O)OR$^{12}$, or —(CR$^5$R$^6$)$_m$R$^{12}$, wherein m is a interger ranging from 0 to 6;

R$^2$ is H or C$_1$–C$_{12}$ alkyl, wherein one or two carbons of said alkyl are optionally replaced by a heteroatom selected from O, S and N, and are optionally substituted by 1 to 3 substituents selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, C$_6$–C$_{10}$ aryl, 4–10 membered heterocyclic, —S(O)$_n$R$^{10}$, and —SO$_2$NR$^{10}$R$^{11}$, wherein n is an integer ranging from 0 to 2;

each R$^3$ and R$^4$ is independently selected from H, —C(O)R$^{12}$ or C$_1$–C$_{18}$ alkanoyl, wherein in the alkyl portion of said alkanoyl one or two carbons optionally may be replaced by a heteroatom selected from O, S and N;

each R$^5$ and R$^6$ is independently H, halo, or C$_1$–C$_{10}$ alkyl and R$^5$ and R$^6$ may each independently vary when m is greater than 1;

each R$^7$ and R$^8$ is independently selected from H and C$_1$–C$_{18}$ alkyl, wherein one or two carbons of said alkyl are optionally replaced by a heteroatom selected from O, S and N, and are optionally substituted by 1 to 3 substituents selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, C$_6$–C$_{10}$ aryl, 4–10 membered heterocyclic, —S(O)nR10 and —SO$_2$NR$^{10}$R$^{11}$, wherein n is an integer ranging from 0 to 2;

each R$^{10}$, R$^{11}$ and Z is independently H or C$_1$–C$_{10}$ alkyl; wherein one or two carbons of said alkyl are optionally replaced by a heteroatom selected from O, S and N, and are optionally substituted by 1 to 3 substituents selected from the group consisting of —C(O)OR$^{13}$, —OR$^{13}$, —C(O)R$^{13}$, halo, nitro, cyano, 4–10 membered heterocyclic, —R$^{13}$, —NR$^{13}$R$^{14}$, —NHC(O)R$^{13}$, —NHC(O)NR$^{13}$R$^{14}$, C$_6$–C$_{10}$ aryl, 4–10 membered heterocyclic, —S(O)$_n$R$^{13}$ wherein n is an integer ranging from 0 to 2, and —SO$_2$NR$^{13}$R$^{14}$;

R$^{12}$ is a 4–10 membered heterocycyl or C$_6$–C$_{10}$ aryl, wherein said heterocycyl and aryl groups are optionally substituted by 1 to 3 substituents independently selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, C$_6$–C$_{10}$ aryl, 4–10 membered heterocyclic, —S(O)$_n$R$^{10}$, and —SO$_2$NR$^{10}$R$^{11}$, wherein n is an integer ranging from 0 to 2;

each R$^{13}$ and R$^{14}$ is independently H or C$_1$–C6 alkyl optionally substituted by 1 to 3 halo groups;

Y is R$^7$ or —(CR$^5$R$^6$)$_m$R$^{12}$, wherein m is an interger ranging from 0 to 6; and R$^5$ and R$^6$ may each independently vary when m is greater than 1.

Specific preferred embodiments of this invention include the compounds of formula 1 wherein:

$R^2$ is H, $R^3$ is H, X is NH, Y is Me and $R^1$ is 3-(imidazo(4,5-b)pyridin-3-yl)-propyl;

$R^2$ is H, $R^3$ is H, X is NH, Y is Me and $R^1$ is 3-(4-pyridin-3-yl-imidazol-1-yl)-propyl;

$R^2$ is H, $R^3$ is H, X is NH, Y is Me and $R^1$ is 3-quinolin-4-yl-propyl;

$R^2$ is H, $R^3$ is H, X is NH, Y is Me and $R^1$ is 3-(7-methoxy-quinolin-4-yl)-propyl;

$R^2$ is H, $R^3$ is H, X is NH, Y is Me and $R^1$ is 3-benzoimidazol-1-yl-propyl;

$R^2$ is H, $R^3$ is H, X is NH, Y is Me and $R^1$ is 3-indol-1-yl-propyl;

$R^2$ is H, $R^3$ is H, X is NH, Y is Me and $R^1$ is 3-indazol-1-yl-propyl;

$R^2$ is H, $R^3$ is H, X is NH, Y is Me and $R^1$ is 3-carbazol-1-yl-propyl;

$R^2$ is H, $R^3$ is H, X is NH, Y is Me and $R^1$ is 3-(5-phenyl-1H-pyrrol-2-yl)-propyl;

$R^2$ is H, $R^3$ is H, X is NH, Y is Me and $R^1$ is 3-(4-phenyl-imidazol-1-yl)-propyl);

$R^2$ is H, $R^3$ is H, X is NH, Y is Me and $R^1$ is 3-(3-(4-chlorophenyl)-(1,2,4)oxadizol-5-yl)-propyl;

$R^2$ is H, $R^3$ is H, X is NH, Y is Me and $R^1$ is 3-(3-(4-methoxyphenyl)-(1,2,4)oxadizol-5-yl)-propyl;

$R^2$ is H, $R^3$ is H, X is NH, Y is Me and $R^1$ is 3-(3-(4-pyridin-4-yl)-(1,2,4)oxadizol-5-yl)-propyl;

$R^2$ is H, $R^3$ is H, X is NH, Y is Me and $R^1$ is 3-benzotrizol-1-yl-propyl;

$R^2$ is H, $R^3$ is H, X is NH, Y is Me and $R^1$ is 3-pyridin-4-yl-propyl;

$R^2$ is H, $R^3$ is H, X is NH, Y is Me and $R^1$ is 3-(2-pyridin-3-yl-thiazol-4-yl)-propyl;

$R^2$ is H, $R^3$ is H, X is NH, Y is Me and $R^1$ is 3-(2-phenyl-thiazol-5-yl)-propyl;

$R^2$ is H, $R^3$ is H, X is NH, Y is Me and $R^1$ is 3-(4-phenyl-1H-imidazol-2-yl)-propyl.

Other specific preferred embodiments of this invention include the compounds of formula 2 wherein:

$R^2$ is H, $R^3$ is H, $R^4$ is H, X is NH, Y is Me and $R^1$ is 3-(imidazo(4,5-b)pyridin-3-yl)-propyl;

$R^2$ is H, $R^3$ is H, $R^4$ is H, X is NH, Y is Me and $R^1$ is 3-(4-pyridin-3-yl-imidazol-1-yl)-propyl;

$R^2$ is H, $R^3$ is H, $R^4$ is H, X is NH, Y is Me and $R^1$ is 3-quinolin-4-yl-propyl;

$R^2$ is H, $R^3$ is H, $R^4$ is H, X is NH, Y is Me and $R^1$ is 3-(7-methoxy-quinolin-4-yl)-propyl;

$R^2$ is H, $R^3$ is H, $R^4$ is H, X is NH, Y is Me and $R^1$ is 3-benzoimidazol-1-yl-propyl;

$R^2$ is H, $R^3$ is H, $R^4$ is H, X is NH, Y is Me and $R^1$ is 3-indol-1-yl-propyl;

$R^2$ is H, $R^3$ is H, $R^4$ is H, X is NH, Y is Me and $R^1$ is 3-indazol-1-yl-propyl;

$R^2$ is H, $R^3$ is H, $R^4$ is H, X is NH, Y is Me and $R^1$ is 3-carbazol-1-yl-propyl;

$R^2$ is H, $R^3$ is H, $R^4$ is H, X is NH, Y is Me and $R^1$ is 3-(5-phenyl-1H-pyrrol-2-yl)-propyl;

$R^2$ is H, $R^3$ is H, $R^4$ is H, X is NH, Y is Me and R is 3-(4-phenyl-imidazol-1-yl)-propyl);

$R^2$ is H, $R^3$ is H, $R^4$ is H, X is NH, Y is Me and $R^1$ is 3-(3-(4-chlorophenyl)-(1,2,4)oxadizol-5-yl)-propyl;

$R^2$ is H, $R^3$ is H, $R^4$ is H, X is NH, Y is Me and $R^1$ is 3-(3-(4-methoxyphenyl)-(1,2,4)oxadizol-5-yl)-propyl;

$R^2$ is H, $R^3$ is H, $R^4$ is H, X is NH, Y is Me and $R^1$ is 3-(3-(4-pyridin-4-yl)-(1,2,4)oxadizol-5-yl)-propyl;

$R^2$ is H, $R^3$ is H, $R^4$ is H, X is NH, Y is Me and $R^1$ is 3-benzotrizol-1-yl-propyl;

$R^2$ is H, $R^3$ is H, $R^4$ is H, X is NH, Y is Me and $R^1$ is 3-pyridin-4-yl-propyl;

$R^2$ is H, $R^3$ is H, $R^4$ is H, X is NH, Y is Me and $R^1$ is 3-(2-pyridin-3-yl-thiazol-4-yl)-propyl;

$R^2$ is H, $R^3$ is H, $R^4$ is H, X is NH, Y is Me and $R^1$ is 3-(2-phenyl-thiazol-5-yl)-propyl; or $^2$ is H, $R^3$ is H, $R^4$ is H, X is NH, Y is Me and $R^1$ is 3-(4-phenyl-1H-imidazol-2-yl)-propyl.

Still other specific preferred embodiments of this invention include the compounds of formula 3 wherein:

$R^2$ is H, $R^3$ is H, X is NH, Y is Me and $R^1$ is 3-(imidazo(4,5-b)pyridin-3-yl)-propyl;

$R^2$ is H, $R^3$ is H, X is NH, Y is Me and $R^1$ is 3-(4-pyridin-3-yl-imidazol-1-yl)-propyl;

$R^2$ is H, $R^3$ is H, X is NH, Y is Me and $R^1$ is 3-quinolin-4-yl-propyl;

$R^2$ is H, $R^3$ is H, X is NH, Y is Me and $R^1$ is 3-(7-methoxy-quinolin-4-yl)-propyl;

$R^2$ is H, $R^3$ is H, X is NH, Y is Me and $R^1$ is 3-benzoimidazol-1-yl-propyl;

$R^2$ is H, $R^3$ is H, X is NH, Y is Me and $R^1$ is 3-indol-1-yl-propyl;

$R^2$ is H, $R^3$ is H, X is NH, Y is Me and $R^1$ is 3-indazol-1-yl-propyl;

$R^2$ is H, $R^3$ is H, X is NH, Y is Me and $R^1$ is 3-(5-phenyl-1H-pyrrol-2-yl)-propyl;

$R^2$ is H, $R^3$ is H, X is NH, Y is Me and $R^1$ is 3-(4-phenyl-imidazol-1-yl)-propyl);

$R^2$ is H, $R^3$ is H, X is NH, Y is Me and $R^1$ is 3-(3-(4-chlorophenyl)—(1,2,4)oxadizol-5-yl)-propyl;

$R^2$ is H, $R^3$ is H, X is NH, Y is Me and $R^1$ is 3-(3-(4-methoxyphenyl)-(1,2,4)oxadizol-5-yl)-propyl;

$R^2$ is H, $R^3$ is H, X is NH, Y is Me and $R^1$ is 3-(3-(4-pyridin-4-yl)-(1,2,4)oxadizol-5-yl)-propyl;

$R^2$ is H, $R^3$ is H, X is NH, Y is Me and $R^1$ is 3-benzotrizol-1-yl-propyl;

$R^2$ is H, $R^3$ is H, X is NH, Y is Me and $R^1$ is 3-pyridin-4-yl-propyl;

$R^2$ is H, $R^3$ is H, X is NH, Y is Me and $R^1$ is 3-(2-pyridin-3-yl-thiazol-4-yl)-propyl;

$R^2$ is H, $R^3$ is H, X is NH, Y is Me and $R^1$ is 3-(2-phenyl-thiazol-5-yl)-propyl; or $R^2$ is H, $R^3$ is H, X is NH, Y is Me and $R^1$ is 3-(4-phenyl-1H-imidazol-2-yl)-propyl.

Yet other specific preferred embodiments of this invention include the compounds of formula 4 wherein:

$R^2$ is H, $R^3$ is H, $R^4$ is H, X is NH, Y is Me and $R^1$ is 3-(imidazo(4,5-b)pyridin-3-yl)-propyl;

$R^2$ is H, $R^3$ is H, $R^4$ is H, X is NH, Y is Me and $R^1$ is 3-(4-pyridin-3-yl-imidazol-1-yl)-propyl;

$R^2$ is H, $R^3$ is H, $R^4$ is H, X is NH, Y is Me and $R^1$ is 3-(7-methoxy-quinolin-4-yl)-propyl;

$R^2$ is H, $R^3$ is H, $R^4$ is H, X is NH, Y is Me and $R^1$ is 3-benzoimidazol-1-yl-propyl;

$R^2$ is H, $R^3$ is H, $R^4$ is H, X is NH, Y is Me and $R^1$ is 3-indol-1-yl- propyl;

$R^2$ is H, $R^3$ is H, H, $R^4$ is H, X is NH, Y is Me and $R^1$ is 3-indazol-1-yl-propyl;

$R^2$ is H, $R^3$ is H, $R^4$ is H, X is NH, Y isY is Me and $R^1$ is 3-(5-phenyl-1H-pyrrol-2-yl)-propyl;

$R^1$ is H, $R^3$ is H, $R^4$ is H, X is NH, Y is Me and $R^1$ is 3-(4-phenyl-imidazol-1-yl)-propyl);

$R^2$ is H, $R^3$ is H, $R^4$ is H, X is NH, Y is Me and $R^1$ is 3-(3-(4chlorophenyl)-(1,2,4)oxadizol-5-yl)-propyl;

$R^2$ is H, $R^3$ is H, $R^4$ is H, X is NH, Y is Me and $R^1$ is 3-(3-(4-methoxyphenyl)-(1,2,4)oxadizol-5-yl)-propyl;

$R^2$ is H, $R^3$ is H, $R^4$ is H, X is NH, Y is Me and $R^1$ is 3-(3-(4-pyridin-4-yl)-(1,2,4)oxadizol-5-yl)-propyl;

$R^2$ is H, $R^3$ is H, $R^4$ is H, X is NH, Y is Me and $R^1$ is 3-benzotrizol-1-yl-propyl;

$R^2$ is H, $R^3$ is H, $R^4$ is H, X is NH, Y is Me and $R^1$ is 3-pyridin-4-yl-propyl;

$R^2$ is H, $R^3$ is H, $R^4$ is H, X is NH, Y is Me and $R^1$ is 3-(2-pyridin-3-yl-thiazol-4-yl)-propyl;

$R^2$ is H, $R^3$ is H, $R^4$ is H, X is NH, Y is Me and $R^1$ is 3-(2-phenyl-thiazol-5-yl)-propyl; or $R^2$ is H, $R^3$ is H, $R^4$ is H, X is NH, Y is Me and $R^1$ is 3-(4-phenyl-1H-imidazol-2-yl)-propyl.

Still other specific preferred embodiments of the present invention include those wherein:

Z is H, $R^3$ is H, X is NH, $R^2$ is H or Me, Y is Me and $R^1$ is 3-(imidazol4,5-b)pyridin-3-yl)-propyl;

Z is H, $R^3$ is H, X is NH, $R^2$ is H or Me, Y is Me, $R^2$ is H or Me and $R^1$ is 3-(4-pyridin-3-yl-imidazol-1-yl)-propyl;

Z is H, $R^3$ is H, X is NH, $R^2$ is H or Me, Y is Me, $R^2$ is H or Me and $R^1$ is 3-quinolin-4-yl-propyl;

Z is H, $R^3$ is H, X is NH, $R^2$ is H or Me, Y is Me, $R^2$ is H or Me and $R^1$ is 3-(7-methoxy-quinolin-4-yl)-propyl;

Z is H, $R^3$ is H, X is NH, Y is Me, $R^2$ is H or Me and $R^1$ is 3-benzoimidazol-1-yl-propyl;

Z is H, $R^3$ is H, X is NH, Y is Me, $R^2$ is H or Me and $R^1$ is 3-indol-1-yl-propyl;

Z is H, $R^3$ is H, X is NH, Y is Me, $R^2$ is H or Me and $R^1$ is 3-indazol-1-yl-propyl;

Z is H, $R^3$ is H, X is NH, Y is Me, $R^2$ is H or Me and $R^1$ is 3-carbazol-1-yl-propyl;

Z is H, $R^3$ is H, X is NH, Y is Me, $R^2$ is H or Me and $R^1$ is 3-(5-phenyl-1H-pyrrol-2-yl)-propyl;

Z is H, $R^3$ is H, X is NH, Y is Me, $R^2$ is H or Me and $R^1$ is 3-(4-phenyl-imidazol-1-yl)-propyl);

Z is H, $R^3$ is H, X is NH, Y is Me, $R^2$ is H or Me and $R^1$ is 3-(3-(4-chlorophenyl)-(1 ,2,4)oxadizol-5-yl)-propyl;

$R^2$ is H, $R^3$ is H, X is NH, Y is Me, $R^2$ is H or Me and $R^1$ is 3-(3-(4-methoxyphenyl)-(1,2,4)oxadizol-5-yl)-propyl;

$R^2$ is H, $R^3$ is H, X is NH, Y is Me, $R^2$ is H or Me and $R^1$ is 3-(3-(4-pyridin-4-yl)-(1,2,4)oxadizol-5-yl)-propyl;

$R^2$ is H, $R^3$ is H, X is NH, Y is Me, $R^2$ is H or Me and $R^1$ is 3-benzotrizol-1-yl-propyl;

Z is H, $R^3$ is H, X is NH, Y is Me, $R^2$ is H or Me and $R^1$ is 3-pyridin-4-yl-propyl;

Z is H, $R^3$ is H, X is NH, Y is Me, $R^2$ is H or Me and $R^1$ is 3-(2-pyridin-3-yl-thiazol-4-yl)-propyl;

Z is H, $R^3$ is H, X is NH, Y is Me, $R^2$ is H or Me and $R^1$ is 3-(2-phenyl-thiazol-5-yl)-propyl; or Z is H, $R^3$ is H, X is NH, $R^2$ is H or Me, Y is Me and $R^1$ is 3-(4-phenyl-1H-imidazol-2-yl)-propyl.

Still other specific preferred embodiments of this invention include the compounds of formula 6 wherein:

Z is H, $R^3$ is H, $R^4$ is H, X is NH, $R^2$ is H or Me, Y is Me and $R^1$ is 3-(imidazo(4,5-b)pyridin-3-yl)-propyl;

Z is H, $R^3$ is H, $R^4$ is H, X is NH, $R^2$ is H or Me, Y is Me, $R^2$ is H or Me and $R^1$ is 3-(4-pyridin-3-yl-imidazol-1-yl)-propyl;

Z is H, $R^3$ is H, $R^4$ is H, X is NH, $R^2$ is H or Me, Y is Me, $R^2$ is H or Me and $R^1$ is 3-quinolin-4-yl-propyl;

Z is H, $R^3$ is H, $R^4$ is H, X is NH, $R^2$ is H or Me, Y is Me, $R^2$ is H or Me and $R^1$ is 3-(7-methoxy-quinolin-4-yl)-propyl;

Z is H, $R^3$ is H, $R^4$ is H, X is NH, Y is Me, $R^2$ is H or Me and $R^1$ is 3-benzoimidazol-1-yl-propyl;

Z is H, $R^3$ is H, $R^4$ is H, X is NH, Y is Me, $R^2$ is H or Me and $R^1$ is 3-indol-1-yl-propyl;

Z is H, $R^3$ is H, $R^4$ is H, X is NH, Y is Me, $R^2$ is H or Me and $R^1$ is 3-indazol-1-yl-propyl;

Z is H, $R^3$ is H, $R^4$ is H, X is NH, Y is Me, $R^2$ is H or Me and $R^1$ is 3-carbazol-1-yl-propyl;

Z is H, $R^3$ is H, $R^4$ is H, X is NH, Y is Me, $R^2$ is H or Me and $R^1$ is 3-(5-phenyl-1H-pyrrol-2-yl)-propyl;

Z is H, $R^3$ is H, $R^4$ is H, X is NH, Y is Me, $R^2$ is H or Me and $R^1$ is 3-(4-phenyl-imidazol-1-yl)-propyl);

Z is H, $R^3$ is H, $R^4$ is H, X is NH, Y is Me, $R^2$ is H or Me and $R^1$ is 3-(3-(4-chlorophenyl)-(1,2,4)oxadizol-5-yl)-propyl;

$R^2$ is H, $R^3$ is H, $R^4$ is H, X is NH, Y is Me, $R^2$ is H or Me and $R^1$ is 3-(3-(4-methoxyphenyl)-(1,2,4)oxadizol-5-yl)-propyl;

$R^2$ is H, $R^3$ is H, $R^4$ is H, X is NH, Y is Me, $R^2$ is H or Me and $R^1$ is 3-(3-(4-pyrdin-4-yl)-(1,2,4)oxadizol-5-yl)-propyl;

$R^2$ is H, $R^3$ is H, $R^4$ is H, X is NH, Y is Me, $R^2$ is H or Me and $R^1$ is 3-benzotrizol-1-yl-propyl;

Z is H, $R^3$ is H, $R^4$ is H, X is NH, Y is Me, $R^2$ is H or Me and $R^1$ is 3-pyridin-4-yl-propyl;

Z is H, $R^3$ is H, $R^4$ is H, X is NH, Y is Me, $R^2$ is H or Me and $R^1$ is 3-(2-pyridin-3-yl-thiazol-4-yl)-propyl;

Z is H, $R^3$ is H, $R^4$ is H, X is NH, Y is Me, $R^2$ is H or Me and $R^1$ is 3-(2-phenyl-thiazol-5-yl)-propyl; or Z is H, $R^3$ is H, $R^4$ is H, X is NH, $R^2$ is H or Me, Y is Me and $R^1$ is 3-(4-phenyl-1H-imidazol-2-yl)-propyl.

Still other specific preferred embodiments of this invention include the compounds of formula 7 wherein:

Z is H, $R^3$ is H, X is NH, $R^2$ is H or Me, Y is Me and $R^1$ is 3-(imidazo(4,5-b)pyridin-3-yl)-propyl;

Z is H, $R^3$ is H, X is NH, $R^2$ is H or Me, Y is Me, $R^2$ is H or Me and R $^1$ is 3-(4-pyridin-3-yl-imidazol-1-yl)-propyl;

Z is H, $R^3$ is H, X is NH, $R^2$ is H or Me, Y is Me, $R^2$ is H or Me and $R^1$ is 3-quinolin-4-yl-propyl;

Z is H, $R^3$ is H, X is NH, $R^2$ is H or Me, Y is Me, $R^2$ is H or Me and $R^1$ is 3-(7-methoxy-quinolin-4-yl)-propyl;

Z is $R^3$ is H, X is NH, Y is Me, $R^2$ is H or Me and $R^1$ is 3-benzoimidazol-1-yl-propyl;

Z is $R^3$ is H, X is NH, Y is Me, $R^2$ is H or Me and $R^1$ is 3-indol-1-yl-propyl;

Z is $R^3$ is H, X is NH, Y is Me, $R^2$ is H or Me and $R^1$ is 3-indazol-1-yl-propyl;

Z is $R^3$ is H, X is NH, Y is Me, $R^2$ is H or Me and $R^1$ is 3carbazol-1-yl-propyl;

Z is R³ is H, X is NH, Y is Me, R² is H or Me and R¹ is 3-(5-phenyl-1H-pyrrol-2-yl)-propyl;

Z is R³ is H, X is NH, Y is Me, R² is H or Me and R¹ is 3-(4-phenyl-imidazol-1-yl)-propyl);

Z is R³ is H, X is NH, Y is Me, R² is H or Me and R¹ is 3-(3-(4-chlorophenyl)-(1,2,4)oxadizol-5-yl)-propyl;

R² is H, R³ is H, X is NH, Y is Me, R² is H or Me and R¹ is 3-(3-(4-methoxyphenyl)-(1,2,4)oxadizol-5-yl)-propyl;

R² is is H, R³ is H, X is NH, Y is Me, R² is H or Me and R¹ is 3-(3-(4-pyridin-4-yl)-(1,2,4)oxadizol-5-yl)-propyl;

R² is R³ is H, X is NH, Y is Me, R is H or Me and R¹ is 3-benzotrizol-1-yl-propyl;

Z is R³ is H, X is NH, Y is Me, R² is H or Me and R¹ is 3-pyridin-4-yl-propyl;

Z is R³ is H, X is NH, Y is Me, R² is H or Me and R¹ is 3-(2-pyridin-3-yl-thiazol-4yl)-propyl;

Z is R³ is H, X is NH, Y is Me, R² is H or Me and R¹ is 3-(2-phenyl-thiazol-5-yl)-propyl; or Z is R³ is H, X is NH, R² is H or Me, Y is Me and R¹ is 3-(4-phenyl-1H-imidazol-2-yl)-propyl.

Still other specific preferred embodiments of this invention include the compounds of formula 8 wherein:

Z is H, R³ is H, R⁴ is H, X is NH, R² is H or Me, Y is Me and R¹ is 3-(imidazo(4,5-b)pyridin-3-yl)-propyl;

Z is H, R³ is H, R⁴ is H, X is NH, R² is H or Me, Y is Me, R² is H or Me and R¹ is 3-(4-pyridin-3-yl-imidazol-1-yl)-propyl;

Z is H, R³ is H, R⁴ is H, X is NH, R² is H or Me, Y is Me, R² is H or Me and R is 3-quinolin-4-yl-propyl;

Z is H, R³is H, R⁴ is H, X is NH, R² is H or Me, Y is Me, R² is H or Me and R¹ is 3-(7-methoxy-quinolin-4-yl)-propyl;

Z is H, R³ is H, R⁴ is H, X is NH, Y is Me, R² is H or Me and R¹ is 3-benzoimidazol-1-yl-propyl;

Z is H, R³ is H, R⁴ is H, X is NH, Y is Me, R² is H or Me and R¹ is 3-indol-1-yl-propyl;

Z is H, R³ is H, R⁴ is H, X is NH, Y is Me, R² is H or Me and R¹ is 3-indazol-1-yl-propyl;

Z is H, R³ is H, R⁴ is H, X is NH, Y is Me, R² is H or Me and R¹ is 3-carbazol-1-yl-propyl;

Z is R³ is H, R⁴ is H, X is NH, Y is Me, R² is H or Me and R¹ is 3-(5-phenyl-1H-pyrrol-2-yl)-propyl;

Z is R³ is H, R⁴ is H, X is NH, Y is Me, R² is H or Me and R¹ is 3-(4-phenyl-imidazol-1-yl)-propyl);

Z is R³ is H, R⁴ is H, X is NH, Y is Me, R² is H or Me and R¹ is 3-(3-(4-chlorophenyl)-(1,2,4)oxadizol-5-yl)-propyl;

R² is H, R³ is H, R⁴ is H, X is NH, Y is Me, R² is H or Me and R¹ is 3-(3-(4-methoxyphenyl)-(1,2,4)oxadizol-5-yl)-propyl;

R² is H, R³ is H, R⁴ is H, X is NH, Y is Me, R² is H or Me and R¹ is 3-(3-(4-pyridin-4-yl)-(1,2,4)oxadizol-5-yl)-propyl;

R² is H, R³ is H, R⁴ is H,X is NH, Y is Me, R² is H or Me and R¹ is 3-benzotrizol-1-yl-propyl;

Z is H, R³ is H, R⁴ is H, X is NH, Y is Me, R² is H or Me and R¹ is 3-pyridin-4-yl-propyl Z is H, R³ is H, R⁴ is H, X is NH, Y is Me, R² is H or Me and R¹ is 3-(2-pyridin-3-yl-thiazol-4-yl)-propyl;

Z is H, R³ is H, R⁴ is H, X is NH, Y is Me, R² is H or Me and R¹ is 3-(2-phenyl-thiazol-5-yl)-propyl; or Z is H, R³ is H, R⁴ is H, X is NH, R² is H or Me, Y is Me and R¹ is 3-(4-phenyl-1H-imidazol-2-yl)-propyl.

The present invention further relates to a pharmaceutical composition for the treatment of an infection in a mammal, fish or bird which comprises a therapeutically effective amount of a the compound of claims 1, 2, 3, 4, 5, 6, 7 or 8 and a pharmaceutically acceptable carrier.

The present invention further relates to a method of treating an infection in a mammal, fish, or bird which comprises administering to said mammal, fish, or bird a therapeutically effective amount of a the compound of claims 1, 2, 3, 4, 5, 6, 7 or 8.

In addition, the present invention relates to a method of preparing a compound of the formula 1

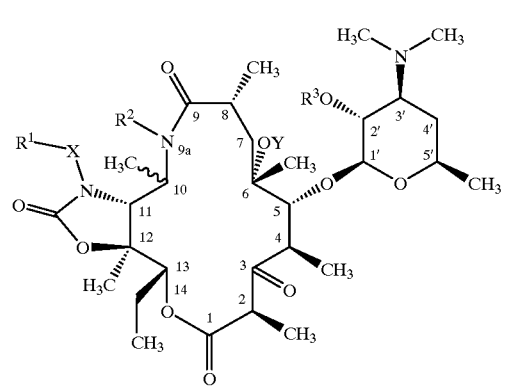

and pharmaceutically acceptable salts thereof, wherein:
X is —O—, —NR⁵—, or $(CR^5R^6)_g$, wherein g is 0 or 1 and wherein, when X is —NR⁵—, R⁵ and R² are taken together to form —(CR⁷R⁸)—;
or X is taken together with R¹ to form —N=CR⁷R⁸;
or X and R¹ are taken together to form a heterocyclic ring of the formula XI

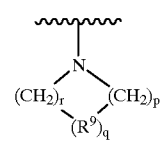

wherein in said ring of formula XI, r and p are each independently an integer ranging from 1 to 3, q is 0 or 1, and R⁹ is —CH₂—, O, S, —C(O)—, —C(S)—, —SO₂—, —CH=CH—, —CH(OH)CH(OH)—, or —NH—; and wherein the $(CH_2)_r$ and $(CH_2)_p$ portions of said ring of formula XI are optionally substituted by 1 to 4 substituents and wherein each hydrogen atom of R⁹ when R⁹ is —CH₂—, —CH=CH—, —CH(OH)CH(OH)—, or —NH is optionally substituted by one substituent, said optional substituents being independently selected from the group consisting of —C(O)OR¹⁰, —OR¹⁰, —C(O)R¹⁰, halo, nitro, cyano, 4–10 membered heterocyclic, —R¹⁰, —NR¹⁰R¹¹, —NHC(O)R¹⁰, —NHC(O)NR¹⁰R¹¹, $C_6$–$C_{10}$ aryl, 4–10 membered heterocyclic, $—S(O)_nR^{10}$, and —SO₂NR¹⁰R¹¹, wherein n is an integer ranging from 0 to 2;

R¹ is H, R⁷, —C(O)R⁷, —C(O)R¹², —C(O)OR⁷, —C(O)OR¹², or $—(CR^5R^6)_mR^{12}$, wherein m is an interger ranging from 0 to 6;

R² is H or $C_1$–$C_{12}$ alkyl, wherein one or two carbons of said alkyl are optionally replaced by a heteroatom selected from O, S and N, and are optionally substituted by 1 to 3 substituents selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, C$_6$–C$_{10}$ aryl, 4–10 membered heterocyclic, —S(O)$_n$R$^{10}$, and —SO$_2$NR$^{10}$R$^{11}$, wherein n is an integer ranging from 0 to 2;

each R$^3$ is independently selected from H, —C(O)R$^{12}$ or C$_1$–C$_{18}$ alkanoyl, wherein in the alkyl portion of said alkanoyl one or two carbons optionally may be replaced by a heteroatom selected from O, S and N;

each R$^5$ and R$^6$ is independently H, halo, or C$_1$–C$_{10}$ alkyl and R$^5$ and R$^6$ may each independently vary when m is greater than 1;

each R$^7$ and R$^8$ is independently selected from H and C$_1$–C$_{18}$ alkyl, wherein one or two carbons of said alkyl are optionally replaced by a heteroatom selected from O, S and N, and are optionally substituted by 1 to 3 substituents selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, C$_6$–C$_{10}$ aryl, 4–10 membered heterocyclic, —S(O)nR10 and —SO$_2$NR$^{10}$R$^{11}$, wherein n is an integer ranging from 0 to 2;

each R$^{10}$ and R$^{11}$is independently H or C$_1$–C$_{10}$ alkyl;

R$^{12}$ is a 4–10 membered heterocycyl or C$_6$–C$_{10}$ aryl, wherein said heterocycyl and aryl groups are optionally substituted by 1 to 3 subsfituents independently selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, C$_6$–C$_{10}$ aryl, 4–10 membered heterocyclic, —S(O)$_n$R$^{10}$, and —SO$_2$NR$^{10}$R$^{11}$, wherein n is an integer ranging from 0 to 2; and Y is R$^7$ or —(CR$^5$R$^6$)$_m$R$^{12}$, wherein m is an interger ranging from 0 to 6; and R$^5$ and R$^6$ may each independently vary when m is greater than 1, which comprises treating a compound of the formula 9

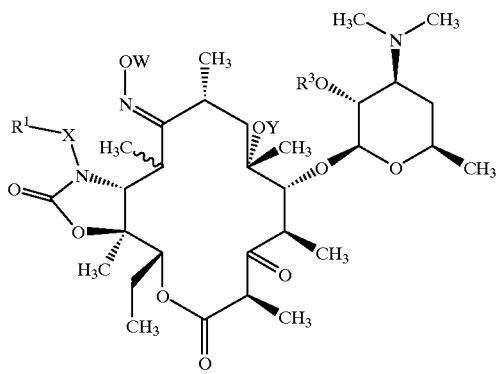

wherein X, Y, R$^1$ and R$^3$ are as defined for the compound of formula 1 and wherein W is a tosyl or a mesyl group, with PCl$_5$ or an acid, to form the compound of formula 1. The acid can be any acid suitable for use in the reaction and can, for example, be selected from the group consisting of H$_2$SO$_4$, formic acid, hydrochloric acid and methanesulfonic acid. An example of a tosyl group is the group ptoluene-shofonyl. An example of a mesyl group is the group methanesulfonyl The present invention further relates to a method of preparing a compound of the formula 2

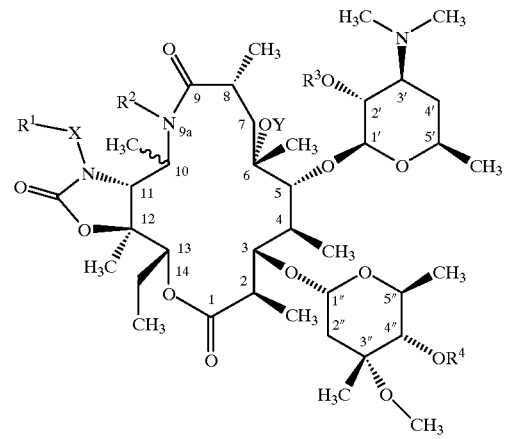

and pharmaceutically acceptable salts thereof, wherein:

X is —O—, —NR$^5$—, or (CR$^5$R$^6$)$_g$, wherein g is 0 or 1 and wherein, when X is —NR$^5$—, R$^5$ and R$^2$ are taken together to form —(CR$^7$R$^8$)—;

or X is taken together with R$^1$ to form —N=CR$^7$R$^8$;

or X and R$^1$ are taken together to form a heterocyclic ring of the formula XI

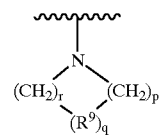

XI wherein in said ring of formula XI, r and p are each independently an integer ranging from 1 to 3, q is 0 or 1, and R$^9$ is —CH$_2$—, O, S, —C(O)—, —C(S)—, —SO$_2$—, —CH=CH—, —CH(OH)CH(OH)—, or —NH—; and wherein the (CH$_2$)$_r$ and (CH$_2$)$_p$ portions of said ring of formula XI are optionally substituted by 1 to 4 substituents and wherein each hydrogen atom of R$^9$ when R$^9$ is —CH$_2$—, —CH=CH—, —CH(OH)CH(OH)—, or —NH is optionally substituted by one subsbtuent, said optional substituents being independently selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)NR$^{10}$, —NHC(O)NR$^{10}$R$^{11}$, C$_6$–C$_{10}$ aryl, 4–10 membered heterocyclic, —S(O)$_n$R$^{10}$, and —SO$_2$NR$^{10}$R$^{11}$, wherein n is an integer ranging from 0 to 2;

R$^1$ is H, R$^7$, —C(O)R$^7$, —C(O)R$^{12}$, —C(O)OR$^7$, —C(O)OR$^{12}$, or —(CR$^5$R$^6$)$_m$R$^{12}$, wherein m is an interger ranging from 0 to 6;

R$^2$ is H or C$_1$–C$_{12}$ alkyl, wherein one or two carbons of said alkyl are optionally replaced by a heteroatom selected from O, S and N, and are optionally substituted by 1 to 3 substituents selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, C$_6$–C$_{10}$ aryl, 4–10 membered heterocyclic, —S(O)$_n$R$^{10}$, and —SO$_2$NR$^{10}$R$^{11}$, wherein n is an integer ranging from 0 to 2;

each R$^3$ and R$^4$ is independently selected from H, —C(O)R$^{12}$ or C$_1$–C$_{18}$ alkanoyl, wherein in the alkyl portion of said alkanoyl one or two carbons optionally may be replaced by a heteroatom selected from O, S and N;

each $R^5$ and $R^6$ is independently H, halo, or $C_1$–$C_{10}$ alkyl and $R^5$ and $R^6$ may each independently vary when m is greater than 1;

each $R^7$ and $R^8$ is independently selected from H and $C_1$–$C_{18}$ alkyl, wherein one or two carbons of said alkyl are optionally replaced by a heteroatom selected from O, S and N, and are optionally substituted by 1 to 3 substituents selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, $C_6$–$C_{10}$ aryl, 4–10 membered heterocyclic, —S(O)nR10 and —SO$_2$NR$^{10}$R$^{11}$, wherein n is an integer ranging from 0 to 2;

each $R^{10}$, and $R^{11}$ is independently H or $C_1$–$C_{10}$ alkyl;

$R^{12}$ is a 4–10 membered heterocycyl or $C_6$–$C_{10}$ aryl, wherein said heterocycyl and aryl groups are optionally substituted by 1 to 3 substituents independently selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, $C_6$–$C_{10}$ aryl, 4–10 membered heterocyclic, —S(O)$_n$R$^{10}$, and —SO$_2$NR$^{10}$R$^{11}$, wherein n is an integer ranging from 0 to 2; and Y is $R^7$ or —(CR$^5$R$^6$)$_m$R$^{12}$, wherein m is an interger ranging from 0 to 6; and $R^5$ and $R^6$ may each independently vary when m is greater than 1, which comprises treating a compound of the formula 10

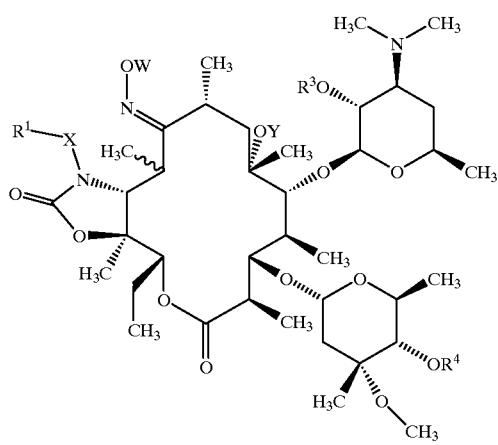

wherein X, Y, $R^1$, $R^3$ and $R^4$ are as defined for the Compound of formula 2 and wherein W is a tosyl or a mesyl group, with PCl$_5$ or an acid, to form the compound of formula 2. The acid can be any acid suitable for use in the reaction and can be for example, selected from the group consisting of H$_2$SO$_4$, formic acid, hydrochloric acid and-methanesulfonic acid.

The present invention further relates to a method of preparing a compound of the formula 3

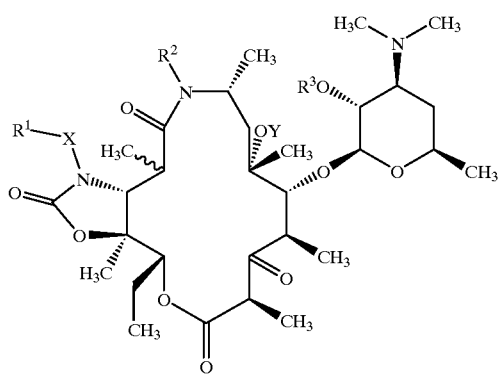

and pharmaceutically acceptable salts thereof, wherein:

X is —O—, —NR$^5$—, or (CR$^5$R$^6$)$_g$, wherein g is 0 or 1;

or X is taken together with $R^1$ to form —N=CR$^7$R$^8$;

or X and $R^1$ are taken together to form a heterocyclic ring of the formula XI

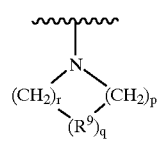

XI wherein in said ring of formula XI, r and p are each independently an integer ranging from 1 to 3, q is 0 or 1, and $R^9$ is —CH$_2$—, O, S, —C(O)—, —C(S)—, —SO$_2$—, —CH=CH—, —CH(OH)CH(OH)—, or —NH—; and wherein the (CH$_2$)$_r$ and (CH$_2$)$_p$ portions of said ring of formula XI are optionally substituted by 1 to 4 substituents and wherein each hydrogen atom of $R^9$ when $R^9$ is —CH$_2$—, —CH=CH—, —CH(OH)CH(OH)—, or —NH is optionally substituted by one substituent, said optional substituents being independently selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, $C_6$–$C_{10}$ aryl, 4–10 membered heterocyclic, —S(O)$_n$R$^{10}$, and —SO$_2$NR$^{10}$R$^{11}$, wherein n is an integer ranging from 0 to 2;

$R^1$ is H, $R^7$, —C(O)R$^7$, —C(O)R$^{12}$, —C(O)OR$^7$, —C(O)OR$^{12}$, or —(CR$^5$R$^6$)$_m$R$^{12}$, wherein m is an interger ranging from 0 to 6;

$R^2$ is H or $C_1$–$C_{12}$ alkyl, wherein one or two carbons of said alkyl are optionally replaced by a heteroatom selected from O, S and N, and are optionally substituted by 1 to 3 substituents selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{11}$, —NHC(O)NR$^{10}$, R$^{11}$, $C_6$–$C_{10}$ aryl, 4–10 membered heterocyclic, —S(O)$_n$R$^{10}$, and —SO$_2$NR$^{10}$R$^{11}$, wherein n is an integer ranging from 0 to 2;

each $R^3$ is independently selected from H, —C(O)R$^{12}$ or $C_1$–$C_{18}$ alkanoyl, wherein in the alkyl portion of said alkanoyl one or two carbons optionally may be replaced by a heteroatom selected from O, S and N;

each $R^5$ and $R^6$ is independently H, halo, or $C_1$–$C_{10}$ alkyl and $R^5$ and $R^6$ may each independently vary when m is greater than 1;

each $R^7$ and $R^8$ is independently selected from H and $C_1$–$C_{18}$ alkyl, wherein one or two carbons of said alkyl are optionally replaced by a heteroatom selected from O, S and N, and are optionally substituted by 1 to 3 substituents selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$, R$^{11}$, $C_6$–$C_{10}$ aryl, 4–10 membered heterocyclic, —S(O)nR10 and —SO$_2$NR$^{10}$R$^{11}$, wherein n is an integer ranging from 0 to 2;

each $R^{10}$ and $R^{11}$ is independently H or $C_1$–$C_{10}$ alkyl;

$R^{12}$ is a 4–10 membered heterocycyl or $C_6$–$C_{10}$ aryl, wherein said heterocycyl and aryl groups are optionally substituted by 1 to 3 subsftuents independently selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, $C_6$–$C_{10}$ aryl, 4–10 membered heterocyclic, —S(O)$_n$R$^{10}$, and —SO$_2$NR$^{10}$, R$^{11}$, wherein n is an integer ranging from 0 to 2; and Y is $R^7$ or —(CR$^5$R$^6$)$_m$R$^{12}$, wherein m is an interger ranging from 0 to 6; and $R^5$ and $R^6$ may each independently vary when m is greater than 1, which comprises treating a compound of the formula 11

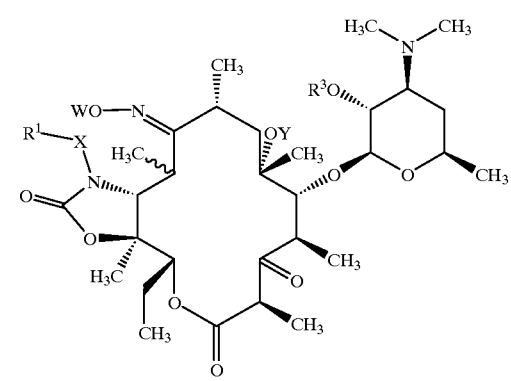

11 wherein X, Y, $R^1$ and $R^3$ are as defined for the compound of formula 3, and wherein W is a tosyl or a mesyl group, with PCl$_5$ or an acid to form the compound of formula 3. The acid can be any acid suitable for use in the reacton and can be, for example, selected from the group consisting of H$_2$SO$_4$, formic acid, hydrochloric acid and methanesulfonic acid.

The present invention further relates to a method of preparing a compound of the formula 4

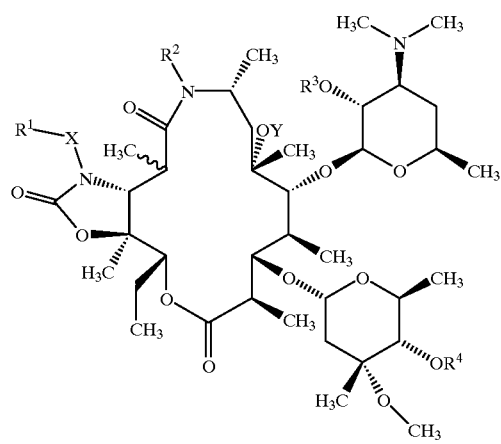

4 and pharmaceutically acceptable salts thereof, wherein:

X is —O—, —NR$^5$—or (CR$^5$R$^6$)$_g$, wherein g is 0 or 1; or X is taken together with $R^1$ to form —N=CR$^7$R$^8$; or X and $R^1$ are taken together to form a heterocyclic ring of the formula XI

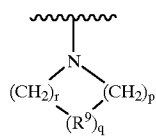

XI wherein in said ring of formula XI, r and p are each independently an integer ranging from 1 to 3, q is 0 or 1, and $R^9$ is —CH$_2$—, O, S, —C(O)—, —C(S)—, —SO$_2$—, —CH=CH—, —CH(OH)CH(OH)—, or —NH—; and wherein the (CH$_2$)$_r$ and (CH$_2$)$_p$ portions of said ring of formula XI are optionally substituted by 1 to 4 substituents and wherein each hydrogen atom of $R^9$ when $R^9$ is —CH$_2$—, —CH=CH—, —CH(OH)CH(OH)—or —NH is optionally substituted by one substituent, said optional substituents being independently selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, $C_6$–$C_{10}$ aryl, 4–10 membered heterocyclic, —S(O)$_n$R$^{10}$, and —SO$_2$NR$^{10}$R$^{11}$, wherein n is an integer ranging from 0 to 2;

$R^1$ is H, $R^7$, —C(O)R$^7$, —C(O)R$^{12}$, C(O)OR$^7$, C(O)OR$^{12}$, or (CR$^5$R$^6$)$_m$R$^{12}$, wherein m is an interger ranging from 0 to 6;

$R^2$ is H or $C_1$–$C_{12}$ alkyld wherein one or two carbons of said alkyl are optionally replaced by a heteroatom selected from O, S and N, and are optionally substituted by 1 to 3 substituents selected from the group consisting of —C(O)OR$^{10}$, —OR$^{10}$, —C(O)R$^{10}$, halo, nitro, cyano, 4–10 membered heterocyclic, —$R^{10}$, —$NR^{10}R^{11}$, —$NHC(O)R^{10}$, —$NHC(O)NR^{10}R^{11}$, $C_6$–$C_{10}$ aryl, 4–10 membered heterocyclic, —$S(O)_n R^{10}$, and —$SO_2NR^{10}R^{11}$, wherein n is an integer ranging from 0 to 2;

each $R^3$ and $R^4$ is independently selected from H, —$C(O)R^{12}$ or $C_1$–$C_{18}$ alkanoyl, wherein in the alkyl portion of said alkanoyl one or two carbons optionally may be replaced by a heteroatom selected from O, S and N;

each $R^5$ and $R^6$ is independently H, halo, or $C_1$–$C_{10}$ alkyl and $R^5$ and $R^6$ may each independently vary when m is greater than 1;

each $R^7$ and $R^8$ is independently selected from H and $C_1$–$C_{18}$ alkyl, wherein one or two carbons of said alkyl are optionally replaced by a heteroatom selected from O, S and N, and are optionally substituted by 1 to 3 substituents selected from the group consisting of —$C(O)OR^{10}$, —$OR^{10}$, —$C(O)R^{10}$, halo, nitro, cyano, 4–10 membered heterocyclic, —$R^{10}$, —$NR^{10}R^{11}$, —$NHC(O)R^{10}$, —$NHC(O)NR^{10}R^{11}$, $C_6$–$C_{10}$ aryl, 4–10 membered heterocyclic, —$S(O)nR10$ and —$SO_2NR^{10}R^{11}$, wherein n is an integer ranging from 0 to 2;

each $R^{10}$ and $R^{11}$ is independently H or $C_1$–$C_{10}$ alkyl;

$R^{12}$ is a 4–10 membered heterocycyl or $C_6$–$C_{10}$ aryl, wherein said heterocycyl and aryl groups are optionally substituted by 1 to 3 substituents independently selected from the group consisting of —$C(O)OR^{10}$, —$OR^{10}$, —$C(O)R^{10}$, halo, nitro, cyano, 4–10 membered heterocyclic, —$R^{10}$, —$NR^{10}R^{11}$, —$NHC(O)R^{10}$, —$NHC(O)NR^{10}R^{11}$, $C_6$–$C_{10}$ aryl, 4–10 membered heterocyclic, —$S(O)_n R^{10}$, and —$SO_2NR^{10}R^{11}$, wherein n is an integer ranging from 0 to 2; and Y is $R^7$ or —$(CR^5R^6)_m R^{12}$, wherein m is an interger ranging from 0 to 6; and $R^5$ and $R^6$ may each independently vary when m is greater than 1, which comprises treating a compound of the formula 12

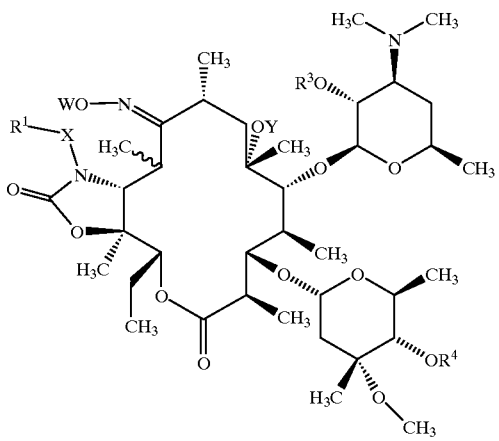

12 wherein X, Y, $R^1$, $R^3$ and $R^4$ are as defined for the compound of formula 4 and wherein W is a tosyl or a mesyl group, with $PCl_5$ or an acid to form the compound of formula 4. The acid can be any acid suitable for use in the reaction and can be, for example, selected from the group consisting of: $H_2SO_4$, formic acid, hydrochloric acid and methanesulfonic.

The present invention further relates to a method of preparing a compound of the formula 5

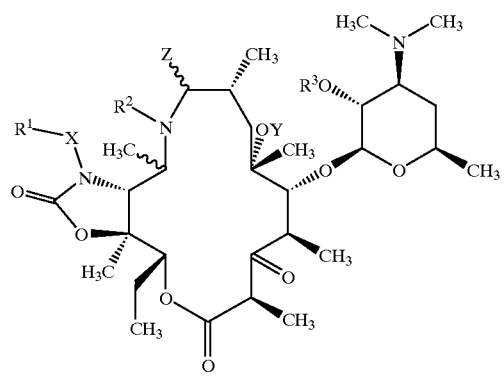

5 and pharmaceutically acceptable salts thereof, wherein:

X is —O—, —$NR^5$—, or $(CR^5R^6)_g$, wherein g is 0 or 1 and wherein, when X is —$NR^5$—, $R^5$ and $R^2$ are taken together to form —$(CR^7R^8)$—;

or X is taken together with $R^1$ to form —$N=C^7R^8$;

or X and $R^1$ are taken together to form a heterocyclic ring of the formula XI

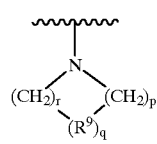

XI wherein in said ring of formula XI, r and p are each independently an integer ranging from 1 to 3, q is 0 or 1, and $R^9$ is —$CH_2$—, O, S, —$C(O)$—, —$C(S)$—, —$SO_2$—, —$CH=CH$—, —$CH(OH)CH(OH)$—, or —$NH$—; and wherein the $(CH_2)_r$ and $(CH_2)_p$ portions of said ring of formula XI are optionally substituted by 1 to 4 substituents and wherein each hydrogen atom of $R^9$ when $R^9$ is —$CH_2$—, —$CH=CH$—, —$CH(OH)CH(OH)$—, or —NH is optionally substituted by one substituent, said optional substituents being independently selected from the group consisting of —$C(O)OR^{10}$, —$OR^{10}$, —$C(O)R^{10}$, halo, nitro, cyano, 4–10 membered heterocyclic, —$R^{10}$, —$NR^{10}R^{11}$, —$NHC(O)R^{10}$, —$NHC(O)NR^{10}R^{11}$, $C_6$–$C_{10}$ aryl, 4–10 membered heterocyclic, —$S(O)_n R^{10}$, and —$SO_2NR^{10}R^{11}$, wherein n is an integer ranging from 0 to 2;

$R^1$ is H, $R^7$, —$C(O)R^7$, —$C(O)R^{12}$, —$C(O)OR^7$, —$C(O)OR^{12}$, or —$(CR^5R^6)_m R^{12}$, wherein m is an interger ranging from 0 to 6;

$R^2$ is H or $C_1$–$C_{12}$ alkyl, wherein one or two carbons of said alkyl are optionally replaced by a heteroatom selected from O, S and N, and are optionally substituted by 1 to 3 substituents selected from the group consisting of —$C(O)OR^{10}$, —$OR^{10}$, —$C(O)R^{10}$, halo, nitro, cyano, 4–10 membered heterocyclic, —$R^{10}$, —$NR^{10}R^{11}$, —$NHC(O)R^{10}$, —$NHC(O)NR^{10}R^{11}$, $C_6$–$C_{10}$ aryl, 4–10 membered heterocyclic, —$S(O)_n R^{10}$, and —$SO_2NR^{10}R^{11}$, wherein n is an integer ranging from 0 to 2;

each $R^3$ is independently selected from H, —$C(O)R^{12}$ or $C_1$–$C_{18}$ alkanoyl, wherein in the alkyl portion of said alkanoyl one or two carbons optionally may be replaced by a heteroatom selected from O, S and N;

each $R^5$ and $R^6$ is independently H, halo, or $C_1$–$C_{10}$ alkyl and $R^5$ and $R^6$ may each independently vary when m is greater than 1;

each $R^7$ and $R^8$ is independently selected from H and $C_1$–$C_{18}$ alkyl, wherein one or two carbons of said alkyl are optionally replaced by a heteroatom selected from O, S and N, and are optionally substituted by 1 to 3 substituents selected from the group consisting of —C(O)OR$^{10}$, —OR$^{10}$, —C(O)R$^{10}$, halo, nitro, cyano, 4–10 membered heterocyclic, —R$^{10}$, —NR$^{10}$, R$^{11}$, —NHC(O)R$^{10}$, —NHC(O)NR$^{10}$R$^{11}$, $C_6$–$C_{10}$ aryl, 4–10 membered heterocyclic, —S(O)nR$^{10}$ and —SO$_2$NR$^{10}$R$^{11}$, wherein n is an integer ranging from 0 to 2;

each $R^{10}$, $R^{11}$ and Z is independently H, or $C_1$–$C_{10}$ alkyl; wherein one or two carbons of said alkyl are optionally replaced by a heteroatom selected from O, S and N, and are optionally substituted by 1 to 3 substituents selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, $C_6$–$C_{10}$ aryl, 4–10 membered heterocyclic, —S(O)$_n$R$^{10}$ wherein n is an integer ranging from 0 to 2, and —SO$_2$NR$^{11}$R$^{11}$;

$R^{12}$ is a 4–10 membered heterocycyl or $C_6$–$C_{10}$ aryl, wherein said heterocycyl and aryl groups are optionally substituted by 1 to 3 substituents independently selected from the group consisting of —C(O)OR$^{10}$, —OR$^{10}$, —C(O)R$^{10}$, halo, nitro, cyano, 4–10 membered heterocyclic, —R$^{10}$, —NR$^{10}$, R$^{11}$, —NHC(O)R$^{10}$, —NHC(O)NR$^{10}$R$^{11}$, $C_6$–$C_{10}$ aryl, 4–10 membered heterocyclic, —S(O)$_n$R$^{10}$, and —SO$_2$NR$^{10}$R$^{11}$, wherein n is an integer ranging from 0 to 2; and Y is $R^7$ or —(CR$^5$R$^6$)$_m$R$^{12}$, wherein m is an interger ranging from 0 to 6; and $R^5$ and $R^6$ may each independently vary when m is greater than 1, which comprises treating a compound of the formula 9

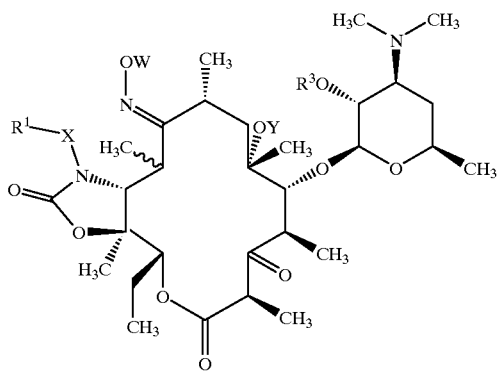

wherein X, Y, $R^1$ and $R^3$ are as defined for the compound of formula 5 and wherein W is a tosyl or a mesyl group, with a compound of the formula Z$_3$Al, wherein Z is defined for the compound of formula 5 to form the compound of formula 5.

The present invention further relates to a method of preparing a compound of the formula 6

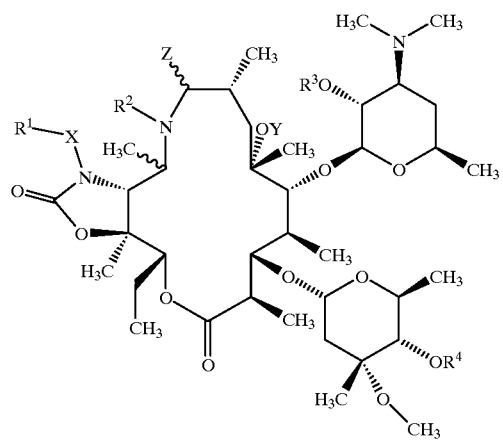

and pharmaceutically acceptable salts thereof, wherein:
X is —O—, —NR$^5$—, or (CR$^5$R$^6$)$_g$, wherein g is 0 or 1 and wherein, when X is —NR$^5$—, $R^5$ and $R^2$ are taken together to form —(CR$^7$R$^8$)—;
or X is taken together with $R^1$ to form —N=CR$^7$R$^8$;
or X and $R^1$ are taken together to form a heterocyclic ring of the formula XI

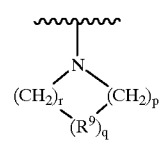

XI wherein in said ring of formula XI, r and p are each independently an integer ranging from 1 to 3, q is 0 or 1, and $R^9$ is —CH$_2$—, O, S, —C(O)—, —C(S)—, —SO$_2$—, —CH=CH—, —CH(OH)CH(OH)—, or —NH—; and wherein the (CH$_2$)$_r$ and (CH$_2$)$_p$ portions of said ring of formula XI are optionally substituted by 1 to 4 substituents and wherein each hydrogen atom of $R^9$ when $R^9$ is —CH$_2$—, —CH=CH—, —CH(OH)CH(OH)—, or —NH is optionally substituted by one substituent, said optional substituents being independently selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, $C_6$–$C_{10}$ aryl, 4–10 membered heterocyclic, —S(O)$_n$R$^{10}$, and —SO$_2$NR$^{10}$R$^{11}$, wherein n is an integer ranging from 0 to 2;
$R^1$ is H, $R^7$, —C(O)R$^7$, —C(O)R$^{12}$, —C(O)OR$^7$, —C(O)OR$^{12}$, or —(CR$^5$R$^6$)$_m$R$^{12}$, wherein m is an interger ranging from 0 to 6;
$R^2$ is H or $C_1$–$C_{12}$ alkyl, wherein one or two carbons of said alkyl are optionally replaced by a heteroatom selected from O, S and N, and are optionally substituted by 1 to 3 substituents selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, $C_6$–$C_{10}$ aryl, 4–10 membered heterocyclic, —S(O)$_n$R$^{10}$, and —SO$_2$NR$^{10}$R$^{11}$, wherein n is an integer ranging from 0 to 2;
each $R^3$ and $R^4$ is independently selected from H, —C(O)R$^{12}$ or $C_1$–$C_{18}$ alkanoyl, wherein in the alkyl portion of said alkanoyl one or two carbons optionally may be replaced by a heteroatom selected from O, S and N;

each $R^5$ and $R^6$ is independently H, halo, or $C_1$–$C_{10}$ alkyl and $R^5$ and $R^6$ may each independently vary when m is greater than 1;

each $R^7$ and $R^8$ is independently selected from H and $C_1$–$C_{18}$ alkyl, wherein one or two carbons of said alkyl are optionally replaced by a heteroatom selected from O, S and N, and are optionally substituted by 1 to 3 substituents selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$, R$^{11}$, $C_6$–$C_{10}$ aryl, 4–10 membered heterocyclic, —S(O)nR10 and —SO$_2$NR$^{10}$R$^{11}$, wherein n is an integer ranging from 0 to 2;

each $R^{10}$, $R^{11}$ and Z is independently H, or $C_1$–$C_{10}$ alkyl; wherein one or two carbons of said alkyl are optionally replaced by a heteroatom selected from O, S and N, and are optionally substituted by 1 to 3 substituents selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, $C_6$–$C_{10}$ aryl, 4–10 membered heterocyclic, —S(O)$_n$R$^{10}$ wherein n is an integer ranging from 0 to 2, and —SO$_2$NR$^{10}$R$^{11}$;

$R^{12}$ is a 4–10 membered heterocycyl or $C_6$–$C_{10}$ aryl, wherein said heterocycyl and aryl groups are optionally substituted by 1 to 3 substituents independently selected from the group consisting of —C(O)OR$^{10}$, —OR$^{10}$, —(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, $C_6$–$C_{10}$ aryl, 4–10 membered heterocyclic, —S(O)$_n$R$^{10}$, and —SO$_2$NR$^{10}$R$^{11}$, wherein n is an integer ranging from 0 to 2; and Y is $R^7$ or —(CR$^5$R$^6$)$_m$R$^{12}$, wherein m is an interger ranging from 0 to 6; and $R^5$ and $R^6$ may each independently vary when m is greater than 1, which comprises treating a the compound of the formula 10

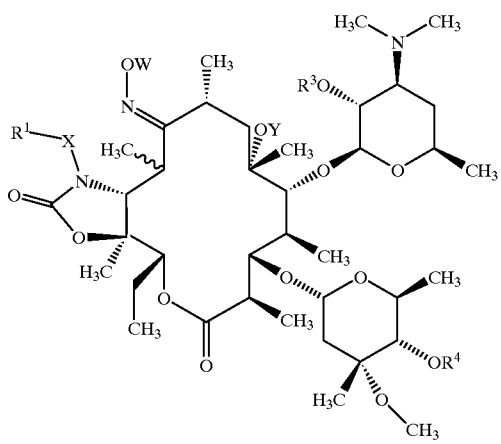

wherein X, Y, $R^1$, $R^3$ and $R^4$ are as defined for the compound of formula 6 and wherein W is a tosyl or a mesyl group, with a compound of the formula Z$_3$Al, wherein Z is defined for the compound of formula 6 to form the compound of formula 6.

The present invention relates to a method of preparing a compound of the formula 7

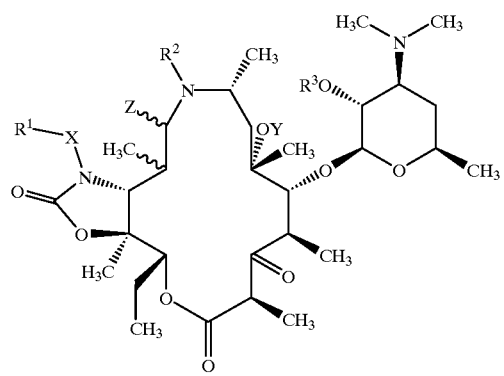

and pharmaceutically acceptable salts thereof, wherein:

X is —O—, —NR$^5$—, or (CR$^5$R$^6$)$_g$, wherein g is 0 or 1; or X is taken together with $R^1$ to form —N=CR$^7$R$^8$; or X and $R^1$ are taken together to form a heterocyclic ring of the formula XI

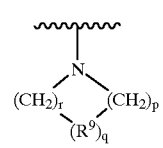

wherein in said ring of formula XI, r and p are each independently an integer ranging from 1 to 3, q is 0 or 1, and $R^9$ is —CH$_2$—, O, S, —C(O)—, —C(S)—, —SO$_2$—, —CH=CH—, —CH(OH)CH(OH)—, or —NH—; and wherein the (CH$_2$)$_r$ and (CH$_2$)$_p$ portions of said ring of formula XI are optionally substituted by 1 to 4 subsfituents and wherein each hydrogen atom of $R^9$ when $R^9$ is —CH$_2$—, —CH=CH—, —CH(OH)CH(OH)—, or —NH is optionally substituted by one substituent, said optional substituents being independently selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, $C_6$–$C_{10}$ aryl, 4–10 membered heterocyclic, —S(O)$_n$R$^{10}$, and SO$_2$NR$^{10}$R$^{11}$, wherein n is an integer ranging from 0 to 2;

$R^1$ is H, $R^7$, —C(O)R$^7$, —C(O)R$^{12}$, —C(O)OR$^7$, —C(O)OR$^{12}$, or —(CR$^5$R$^6$)$_m$R$^{12}$, wherein interger ranging from 0 to 6;

$R^2$ is H or $C_1$–$C_{12}$ alkyl, wherein one or two carbons of said alkyl are optionally replaced by a heteroatom selected from O, S and N, and are optionally substituted by 1 to 3 substituents selected from the group consisting of —C(O)OR$^{10}$, —OR$^1$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, $C_6$–$C_{10}$ aryl, 4–10 membered heterocyclic, —S(O)$_n$R$^{10}$, and —SO$_2$NR$^{10}$R$^{11}$, wherein n is an integer ranging from 0 to 2;

each $R^3$ is independently selected from H, —C(O)R$^{12}$ or $C_1$–$C_{18}$ alkanoyl, wherein in the alkyl portion of said alkanoyl one or two carbons optionally may be replaced by a heteroatom selected from O, S and N;

each $R^5$ and $R^6$ is independently H, halo, or $C_1$–$C_{10}$ alkyl and $R^5$ and $R^6$ may each independently vary when m is greater than 1;

each $R^7$ and $R^8$ is independently selected from H and $C_1$–$C_{18}$ alkyl, wherein one or two carbons of said alkyl are optionally replaced by a heteroatom selected from O, S and N, and are optionally substituted by 1 to 3 substituents selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, $C_6$–$C_{10}$ aryl, 4–10 membered heterocyclic, —S(O)nR10 and —SO$_2$NR$^{10}$R$^{11}$, wherein n is an integer ranging from 0 to 2;

each $R^{10}$, $R^{11}$ and Z is independently H, or $C_1$–$C_{10}$ alkyl; wherein one or two carbons of said alkyl are optionally replaced by a heteroatom selected from O, S and N, and are optionally substituted by 1 to 3 substituents selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, $C_6$–$C_{10}$ aryl, 4–10 membered heterocyclic, —S(O)$_n$R$^{10}$ wherein n is an integer ranging from 0 to 2, and —SO$_2$NR$^{10}$R$^{11}$;

$R^{12}$ is a 4–10 membered heterocycyl or $C_6$–$C_{10}$ aryl, wherein said heterocycyl and aryl groups are optionally substituted by 1 to 3 substituents independently selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, $C_6$–$C_{10}$ aryl, 4–10 membered heterocyclic, —S(O)$_n$R$^{10}$, and —SO$_2$NR$^{10}$R$^{11}$, wherein n is an integer ranging from 0 to 2; and Y is $R^7$ or —(CR$^5$R$^6$)$_m$R$^{12}$, wherein m is an interger ranging from 0 to 6; and $R^5$ and $R^6$ may each independently vary when m is greater than 1, which comprises treating a the compound of the formula 11

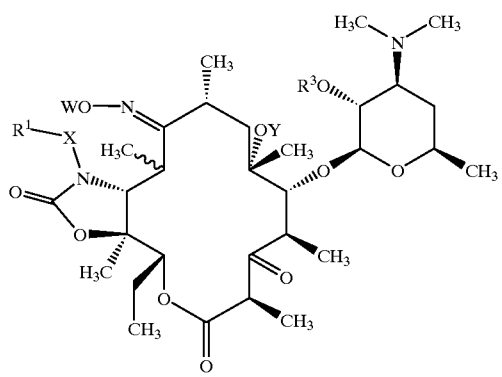

11 wherein X, Y, $R^1$ and $R^3$ are as defined for the compound of formula 7 and wherein W is a tosyl or a mesyl group, with a compound of the formula Z$_3$Al, where Z is defined for the compound of 7 to form the compound of formula 7, The present invention relates to a method of preparing of the formula 8

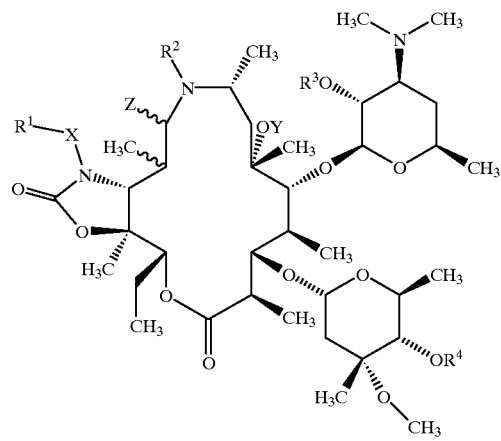

8 and pharmaceutically acceptable salts thereof, wherein:

X is —O—, —NR$^5$—, or (CR$^5$R$^6$)$_g$, wherein 9 is 0 or 1;
or X is taken together with $R^1$ to form —N=CR$^7$R$^8$;
or X and $R^1$ are taken together to form a heterocyclic ring of the formula XI

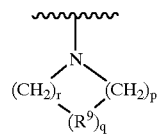

XI wherein in said ring of formula XI, r and p are each independently an integer ranging from 1 to 3, q is 0 or 1, and $R^9$ is —CH$_2$—, O, S, —C(O)—, —C(S)—, —SO$_2$—, —CH=CH—, —CH(OH)CH(OH)—, or —NH—; and wherein the (CH$_2$)$_r$ and (CH$_2$)$_p$ portions of said ring of formula XI are optionally substituted by 1 to 4 substituents and wherein each hydrogen atom of $R^9$ when $R^9$ is —CH$_2$—, —CH=CH—, —CH(OH)CH(OH)—, or —NH is optionally substituted by one substituent, said optional substituents being independently selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, $C_6$–$C_{10}$ aryl, 4–10 membered heterocyclic, —S(O)$_n$R$^{10}$, and —SO$_2$NR$^{10}$R$^{11}$, wherein n is an integer ranging from 0 to 2;

$R^1$ is H, $R^7$, —C(O)R$^7$, —C(O)R$^{12}$, —C(O)OR$^7$, —C(O)OR$^{12}$, or —(CR$^5$R$^6$)$_m$R$^{12}$, wherein m is an interger ranging from 0 to 6;

$R^2$ is H or $C_1$–$C_{12}$ alkyl, wherein one or two carbons of said alkyl are optionally replaced by a heteroatom selected from O, S and N, and are optionally substituted by 1 to 3 substituents selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, $C_6$–$C_{10}$ aryl, 4–10 membered heterocyclic, —S(O)$_n$R$^{10}$, and SO$_2$NR$^{10}$R$^{11}$, wherein n is an integer ranging from 0 to 2;

each $R^3$ and $R^4$ is independently selected from H, —C(O)R$^{12}$ or $C_1$–$C_{18}$ alkanoyl, wherein in the alkyl portion of said alkanoyl one or two carbons optionally may be replaced by a heteroatom selected from O, S and N;

each $R^5$ and $R^6$ is independently H, halo, or $C_1$–$C_{10}$ alkyl and $R^5$ and $R^6$ may each independently vary when m is greater than 1;

each $R^7$ and $R^8$ is independently selected from H and $C_1$–$C_{18}$ alkyl, wherein one or two carbons of said alkyl are optionally replaced by a heteroatom selected from O, S and N, and are optionally substituted by 1 to 3 substituents selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, $C_6$–$C_{10}$ aryl, 4–10 membered heterocyclic, —S(O)nR10 and —SO$_2$NR$^{10}$R$^{11}$, wherein n is an integer ranging from 0 to 2;

each $R^{10}$, $R^{11}$ and Z is independently H, or $C_1$–$C_{10}$ alkyl; wherein one or two carbons of said alkyl are optionally replaced by a heteroatom selected from O, S and N, and are optionally substituted by 1 to 3 substituents selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, $C_6$–$C_{10}$ aryl, 4–10 membered heterocyclic, —S(O)$_n$R$^{10}$ wherein n is an integer ranging from 0 to 2, and —SO$_2$NR$^{10}$R$^{11}$;

$R^{12}$ is a 4–10 membered heterocycyl or $C_6$–$C_{10}$ aryl, wherein said heterocycyl and aryl groups are optionally substituted by 1 to 3 substituents independently selected from the group consisting of —C(O)OR$^{10}$, —OR$^{10}$, C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, $C_8$–$C_{10}$ aryl, 4–10 membered heterocyclic, —S(O)$_n$R$^{10}$, and —SO$_2$NR$^{10}$R$^{11}$, wherein n is an integer ranging from 0 to 2; and Y is $R^7$ or —(CR$^5$R$^6$)$_m$R$^{12}$, wherein m is an interger ranging from 0 to 6; and $R^5$ and $R^6$ may each independently vary when m is greater than 1, which comprises treating a compound of the formula 12

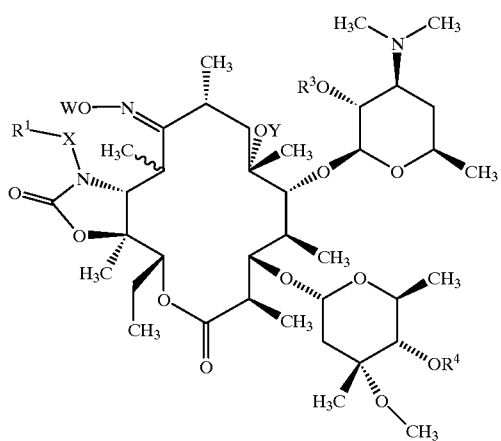

12 wherein X, Y, $R^1$, $R^3$ and $R^4$ are as defined for the compound of formula 8 and wherein W is a tosyl or a mesyl group, with a compound of the formula Z$_3$Al, wherein Z is as defined for the compound of formula 8, to form the compound of formula 8.

Patients that can be treated with the compounds of formulae 1–8, and the pharmaceutically acceptable salts thereof, include mammals (particularly humans), fish, and birds suffering from infections caused by various microorganisms including Gram positive and Gram negative bacteria.

As used herein, unless otherwise indicated, the term "bacterial infection(s)" or "protozoa infections; includes bacterial infections and protozoa infections that occur in mammals, fish and birds as well as disorders related to bacterial infections and patozoa infections that may be treated or prevented by administering antibiotics such as the compounds of the present invention. Such bacterial infections and protozoa infections and disorders related to such infections include the following: pneumonia, otitis media, sinusitus, bronchitis, tonsillitis, and mastoiditis related to infection by *Streptococcus pneumoniae, Haemophilus influenzae, Moraxella catarrhalis, Staphylococcus aureus*, or *Peptostreptococcus* spp.; pharynigitis, rheumatic fever, and glomerulonephritis related to infection by *Streptococcus pyogenes*, Groups C and G streptococci, *Closttidium dipthenae*, or *Actinobacillus haemolyticum*; respiratory tract infections related to infection by *Mycoplasma pneumoniae, Legionella pneumophila, Streptococcus pneumoniae, Haemophilus influenzae*, or *Chlamydia pneumoniae*; uncomplicated skin and soft tissue infections, abscesses and osteomyelitis, and puerperal fever related to infection by *Staphylococcus aureus*, coagulase-positive staphylococci (i.e., *S. epidermidis, S. hemolyticus*, etc.), *Streptococcus pyogenes, Streptococcus agalactiae*, Streptococcal groups C–F (minute-colony streptococci), viridans streptococci, *Corynebacterium minutissimum*, Clostridium spp., or *Bartonella henselae*; uncomplicated acute urinary tract infections related to infection by *Staphylococcus saprophyticus* or Enterococcus spp.; urethritis and cervicitis; and sexually transmitted diseases related to infection by *Chlamydia trachomatis, Haemophilus ducreyi, Treponema pallidum, Ureaplasma urealyticum*, or *Neisema gonorrheae*; toxin diseases related to infection by *S. aureus* (food poisoning and Toxic shock syndrome), or Groups A, B, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *Chlamydia trachomatis, Neisseria gonorrhoeae, S. aureus, S. pneumoniae, S. pyogenes, H. influenzae*, or *Listeria* spp.; disseminated *Mycobactetium avium* complex (MAC) disease related to infection by *Mycobacterium avium*, or *Mycobactedum intracellulare*; gastroenteritis related to infection by *Campylobacter jejuni*; intestinal protozoa related to infection by Cryptosporidium spp.; odontogenic infection related to infection by viridans streptococci; persistent cough related to infection by *Bordetella pertussis*; gas gangrene related to infection by *Clostridium perfringens* or Bacteroides spp.; and atherosclerosis related to infection by *Helicobacter pylori* or *Chlamydia pneumoniae*. Bacterial infections and protozoa infections and disorders related to such infections that may be treated or prevented in animals include the following: bovine respiratory disease related to infection by *P. haem., P. multocida, Mycoplasma bovis*, or Bordetella spp.; cow enteric disease related to infection by *E. coli* or protozoa (i.e., coccidia, cryptosporidia, etc.); dairy cow mastitis related to infection by *Staph. aureus, Strep. uberis, Strep. agalactiae, Strep. dysgalactiae*, Klebsiella spp., Corynebacterium, or Enterococcus spp.; swine respiratory disease related to infection by *A. pleuro., P. multocida*, or Mycoplasma spp.; swine enteric disease related to infection by *E. coli, Lawsonia intracellularis*, Salmonella, or *Serpulina hyodyisinteriae*; cow footrot related to infection by Fusobacterium spp.; cow metritis related to infection by *E. coli*; cow hairy warts related to infection by *Fusobacterium necrophorum* or *Bacteroides nodosus*; cow pink-eye related to infection by

*Moraxella bovis*; cow premature abortion related to infection by protozoa (i.e. neosporium); urinary tract infection in dogs and cats related to infection by *E. coli*; skin and soft tissue infections in dogs and cats related to infection by *Staph. epidennidis, Staph. intermedius*, coagulase neg. Staph. or *P. multocida*; and dental or mouth infections in dogs and cats related to infection by Alcaligenes spp., Bacteroides spp., Clostridium spp., Enterobacter spp., Eubacterium, Peptostreptococcus, Porphyromonas, or Prevotella. Other bacterial infections and protozoa infections and disorders related to such infections that may be treated or prevented in accord with the method of the present invention are referred to in J. P. Sanford et al., "The Sanford Guide To Antimicrobial Therapy," 26th Edition, (Antimicrobial Therapy, Inc., 1996).

In the chemical structures depicted herein, a wavy line indicates that the stereochemistry at the chiral center to which the wavy line is connected is either an R or S configuration where the wavy line is connected to a carbon atom. In the compounds of formulae 1–8, the wavy line at position 10 of the macrolide ring indicates that the methyl group can be either R or S configuration at that position. In the compound of formulae 1–8, the wavy line connected to the oxime nitrogen at position 9 of the macrolide ring indicates that the —$OR^1$ moiety is in an E or $R^9$ configuration.

The term "halo", as used herein, unless otherwise indicated, means fluoro, chloro, bromo or iodo. Preferred halo groups are fluoro, chloro and bromo.

The term "alkyl", as used herein, unless otherwise indicated, includes saturated monovalent hydrocarbon radicals having straight, cyclic or branched moieties. Said alkyl group may include one or two double or triple bonds. It is understood that for cyclic moieties at least three carbon atoms are required in said alkyl group.

The term "alkanoyl", as used herein, unless otherwise indicated, includes —C(O)-alkyl groups wherein "alkyl" is as defined above.

The term "aryl", as used herein, unless otherwise indicated, includes an organic radical derived from an aromatic hydrocarbon by removal of one hydrogen, such as phenyl or naphthyl.

The term "4–10 membered heterocyclic", as used herein, unless otherwise indicated, includes aromatic and non-aromatic heterocyclic groups containing one or more heteroatoms each selected from O, S and N, wherein each heterocyclic group has from 4–10 atoms in its ring system. Non-aromatic heterocyclic groups include groups having only 4 atoms in their ring system, but aromatic heterocyclic groups must have at least 5 atoms in their ring system. The heterocyclic groups include benzo-fused ring systems and ring systems substituted with one or more oxo moieties. An example of a 4 membered heterocyclic group is azetidinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3—azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the compounds listed above, may be C-attached or N-attached where such is possible. For instance, a group derived from pyrrole may be pyrrol-1-yl (N-attached) or pyrrol-3-yl (C-attached).

As used herein, unless otherwise indicated, "Ac" indicates an acetyl group.

As used herein, unless otherwise indicated, "Me" indicates a methyl group.

As used herein, unless otherwise indicated, "Et" indicates an ethyl group.

As used herein, unless otherwise indicated, "Pr" indicates a propyl group.

The phrase "pharmaceutically acceptable salt(s)", as used herein, unless otherwise indicated, includes salts of acidic or basic groups which may be present in the compounds of formulae 1–8. The compounds of formulae 1–8 that are basic in nature are capable of forming a wide variety of salts with various inorganic and organic acids. The acids that may be used to prepare pharmaceutically acceptable acid addition salts of such basic compounds of formulae 1–8 are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid dtrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts.

Those compounds of the formulae 1–8 that are acidic in nature, are capable of forming base salts with various pharmacologically acceptable cations. Examples of such salts include the alkali metal or alkaline earth metal salts and particularly, the sodium and potassium salts.

The present invention also includes all radiolabelled forms of the compounds of formulae 1–8, and pharmaceutically acceptable salts thereof, wherein the radiolabel is selected from $^3H$, $^{11}C$ and $^{14}C$. Such radiolabelled compounds are useful as research or diagnostic tools.

The certain compounds of formulae 1–8 may have asymmetric centers and therefore exist in different enantiomeric forms. This invention relates to the use of all optical isomers and stereoisomers of the compounds of formulae 1–8 and mixtures thereof. In particular, the invention includes both the R and S configurations of the methyl group at C-10 of the macrolide ring of formulae 1–8, and both the E and Z configurations of the —$OR^2$ group connected to the nitrogen of the oxime moiety at C-9 of the macrolide ring of formulae 1–8. The compounds of formulae 1–8 may also exist as tautomers. This invention relates to the use of all such tautomers and mixtures thereof.

DETAILED DESCRIPTION OF THE INVENTION

The preparation of the compounds of the present invention is illustrated in the following Schemes 1 to 8.

Scheme 1 illustrates the general synthesis of the compounds of formula 1. In Scheme 1, the starting compound of formula 13 can be prepared as described in International Patent Appln. PCT/IB98/00741, filed May 15, 1998 (Yong-Jin Wu) and U.S. application Ser. No. 60/049,349 filed Jun. 11, 1997 (Yong-Jin Wu), both of which are incorporated by reference herein in their entirety. In step 1 of Scheme 1, the compounds of formula 9, wherein W is a tosyl or a mesyl group, can be prepared by treating the compounds of formula 13 with tosyl chloride or mesyl chloride in the presence of a base, in a solvent such as dichloromethane, or tetrahydrofuran (THF). The preferred bases are triethylamine, pyridine, DBU, diisopropylethylamine. In step 2 of Scheme 1, the compounds of formula 9 can undergo a Beckmann rearrangement under the conditions as described in March (J. March, Advanced Org. Chem., 4$^{th}$ edition, pp. 1095–1097, John Wiley and Sons, 1992), to provide the compounds of formula 14. The preferred reagents for this Beckmann rearrangement reaction are $PCl_5$, pyridine-HCl, methanesulfonic acid, polyphosphoric acid. In step 3 of Scheme 1, the conversion of the compounds of formula 14 to those of formula 1 can be achieved via alkylation using procedures known to those of skill in the art. Examples of alkylating agents are described in March (J. March, Advanced Org. Chem., 4$^{th}$ edition, pp. 1095–1097, John Wiley and Sons, 1992).

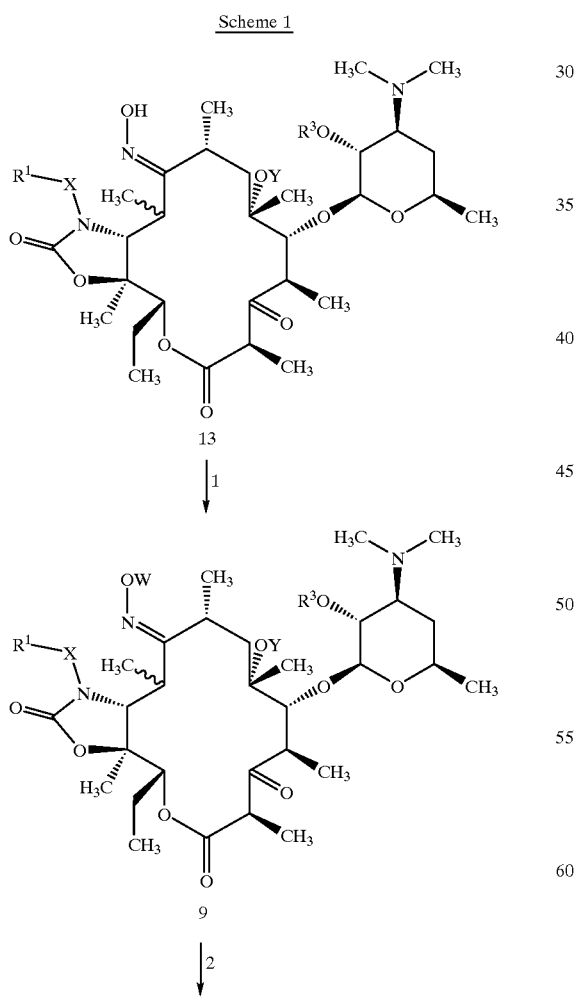

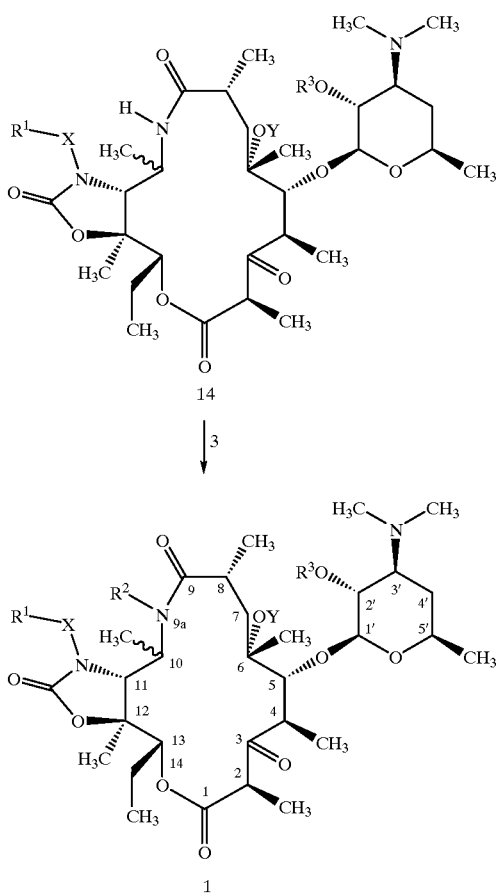

Scheme 2 illustrates the general synthesis of the compounds of formula 2. In Scheme 2, the starting compound of formula 15 can be prepared as described in U.S. application Ser. No. 60/106,798, filed Nov. 3, 1998 (PC10205) (Yong-Jin Wu). In step 1 of Scheme 2, the compounds of formula 10, wherein W is a tosyl or a mesyl group, can be prepared by treating the compounds of formula 15 with tosyl chloride or mesyl chloride in the presence of a base in a solvent such as dichloromethane or THF. The preferred bases are triethylamine, pyridine, DBU, diisopropylethylamine. In step 2 of Scheme 2, the compounds of formula 10 can undergo a Beckmann rearrangement under the conditions described in March (J. March, Advanced Org. Chem., 4$^{th}$ edition, pp. 1095–1097) to provide the compounds of formula 16. The preferred reagents for this Beckmann rearrangement reaction are $PCl_5$, pyridine-HCl, methanesulfonic acid and polyphosphoric acid. In step 3 of Scheme 2, the conversion of the compounds of formula 16 to those of formula 2 can be achieved via alkylation.

Scheme 2

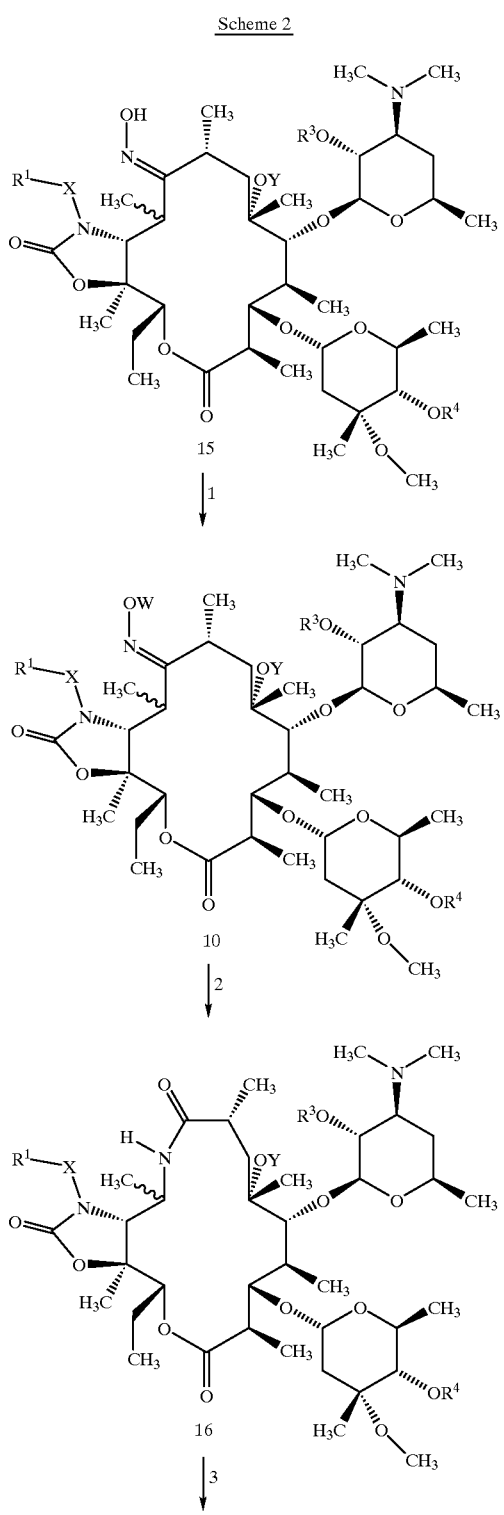

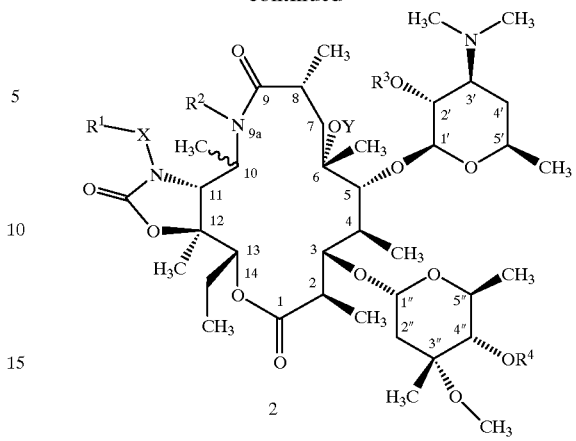

Scheme 3 illustrates the general synthesis of the compounds of formula 3. In Scheme 3, the starting compound of formula 17 can be prepared as described in International Patent Appln. PCT/IB98/00741, filed May 15, 1998 (Yong-Jin Wu) and U.S. application Ser. No. 60/049349 filed Jun. 11, 1997 (Yong-Jin Wu), both of which are incorporated by reference herein in their entirety. In step 1 of Scheme 3, the compounds of formula 11, wherien W is a tosyl or a mesyl group, can be prepared by treating the compounds of formula 17 with tosyl chloride or mesyl chloride in the presence of a base in a solvent such as dichloromethane or THF. The preferred bases are triethylamine, pyridine, DBU, diisopropylethylamine. In step 2 of Scheme 3, the compounds of formula 11 can undergo a Beckmann rearrangement under the conditions described by March (J. March, Advanced Org. Chem., $4^{th}$ edition, pp. 1095–1097) to provide the compounds of formula 18. The preferred reagents for this Beckmann rearrangement reaction are $PCl_5$, pyridine-HCl, methanesulfonic acid and polyphosphoric acid. In step 3 of Scheme 3, the conversion of the compounds of formula 18 to those of formula 3 can be achieved via alkylation.

Scheme 3

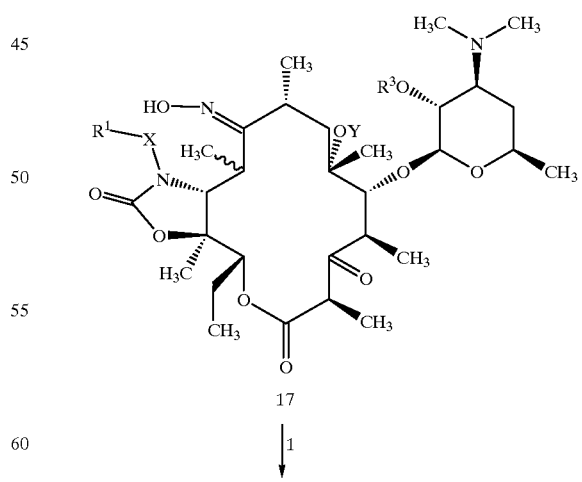

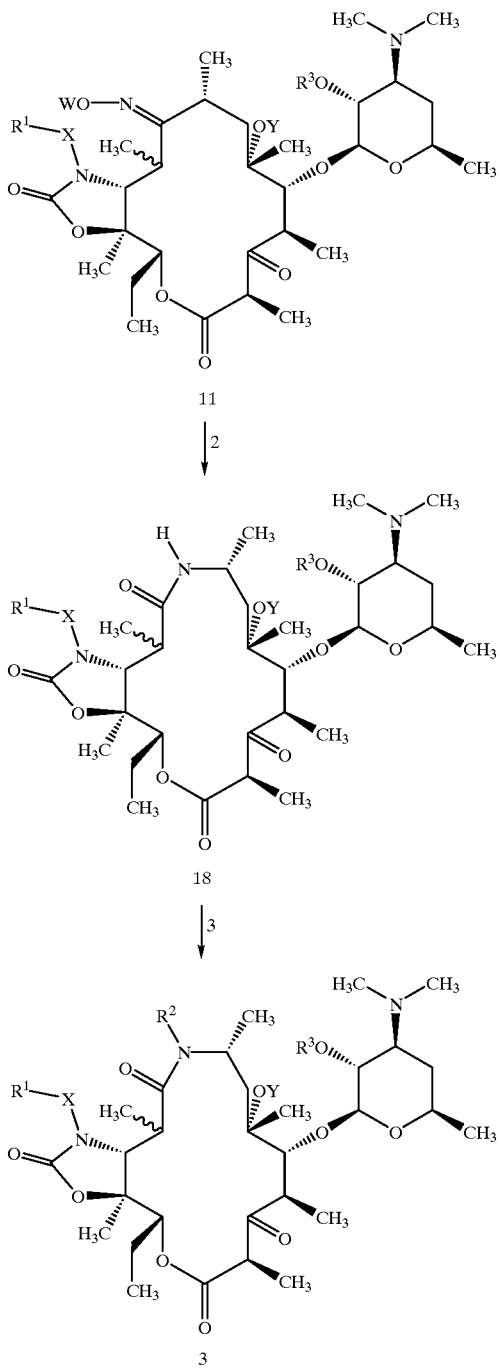

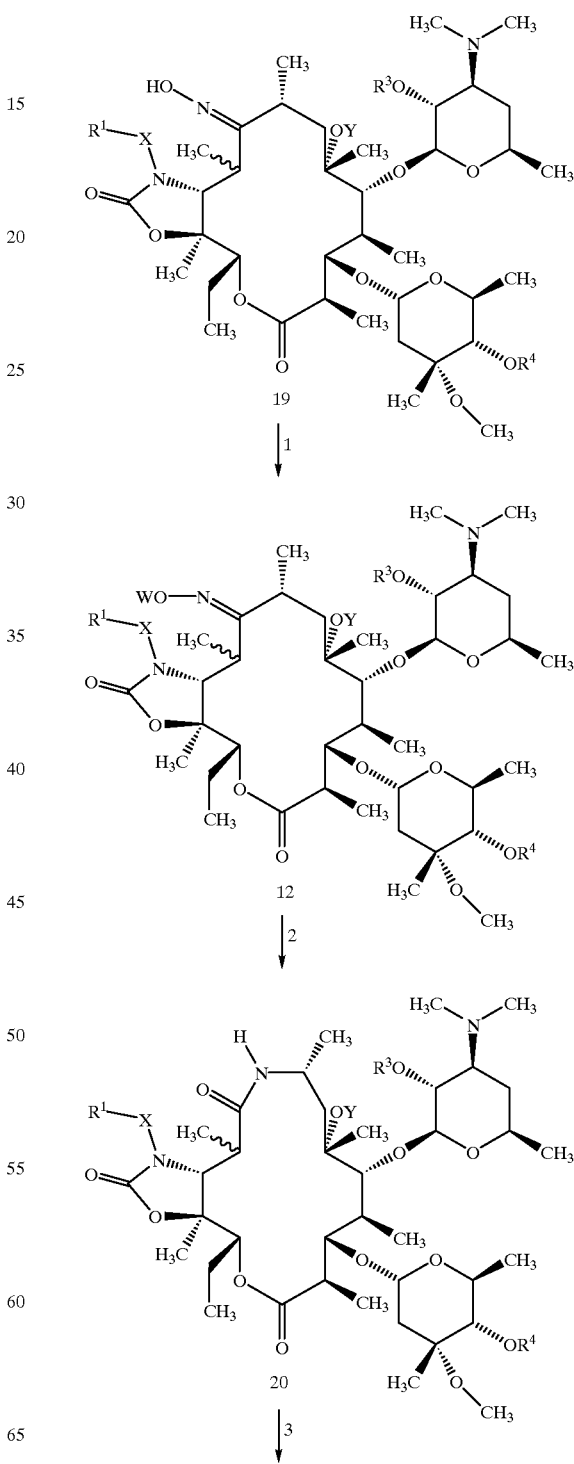

March, Advanced Org. Chem., 4th edition, pp. 1095–1097) to provide the compounds of formula 20. The preferred reagents for this Beckmann rearrangement reaction are $PCl_5$, pyridine-HCl, methanesulfonic acid and polyphosphoric acid. In step 3 of Scheme 4 the conversion of the compounds of formula 20 to those of formula 4 can be achieved via alkylation.

Scheme 4 illustrates the general synthesis of the compounds of formula 4. In Scheme 4, the starting compound of formula 19 can be prepared as described in U.S. Application Ser. No. 60/106,798, filed Nov. 3, 1998 (PC10205) (Yong-Jin Wu). In step 1 of Scheme 4, the compounds of formula 12, wheren W is a tosyl or a mesyl group, can be prepared by treating the compounds of formula 19 with tosyl chloride or mesyl chloride in the presence of a base in a solvent such as dichloromethane or THF. The preferred bases are triethylamine, pyridine, 1,8-Diazabicyclo 95.4.0)undec-7-ene (DBU), diisopropylethylamine. In step 2 of Scheme 4, the compounds of formula 12 can undergo a Beckmann rearrangement under the conditions described by March (J.

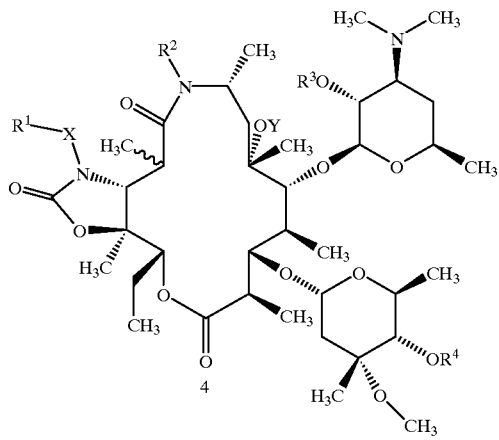

4

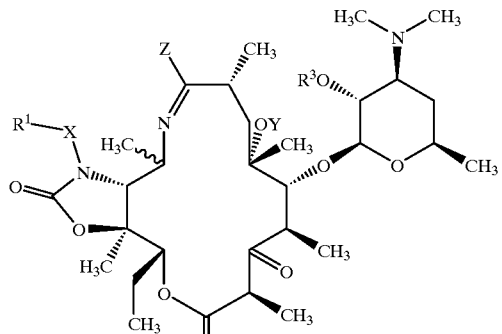

21

↓2

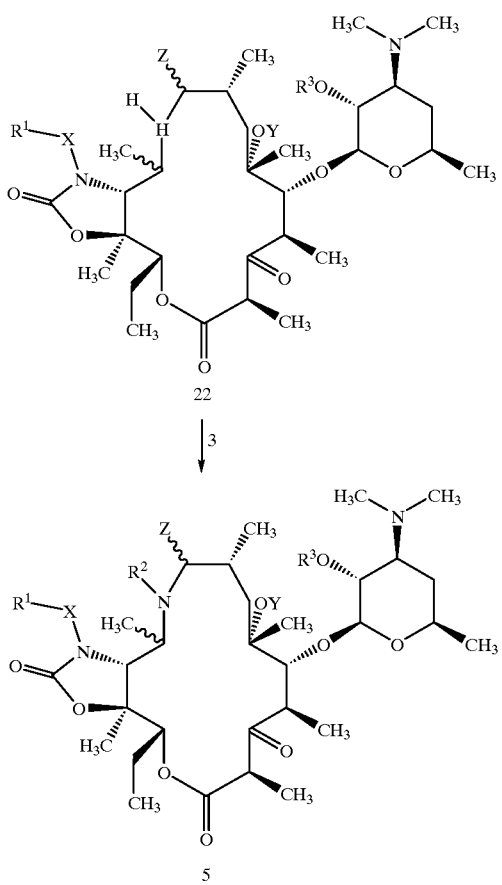

Scheme 5 illustrates the general synthesis of the compounds of formula 5. In Scheme 5, the starting compound of formula 9 can be prepared as described in Scheme 1. In step 1 of Scheme 5, the compounds of formula 9 can be converted to those of formula 22 via Beckmann rearrangement as described in Yamamoto et al (B. M. Trost, Comprehensive Organic Transformations, Volume 4, pp. 763–793). The compounds of formula 22, wherein Z is H, can be prepared directly by treating the compounds of formula 9 with metal hydride reagents in a solvent such as $CH_2Cl_2$ following substantially the same procedures of Yamamoto et al (Tetrahedron Letters, 1983, 24, 4711). The preferred metal hydride reagent is diisobutylaluminium hydride. The compounds of formula 21, wherein Z is not H, can be obtained by treating the compounds of formula 9 with organometallic reagents such as $Z_3Al$, wherein Z is as defined as above, for the compound of formula 5, following substantially the same procedures of Yamamoto et al (J. Amer. Chem. Soc., 1981, 7368). In step 2 of Scheme 5, the transformation of the compound of formula 2 to the compounds of formula 22 can be achieved either by catalytic hydrogenation or metal hydride reduction using, for example, diisobutylaluminium hydride. In step 3 of Scheme 5, the conversion of the compounds of formula 22 to the compounds of formula 5 can be effected by alkylation.

Scheme 5

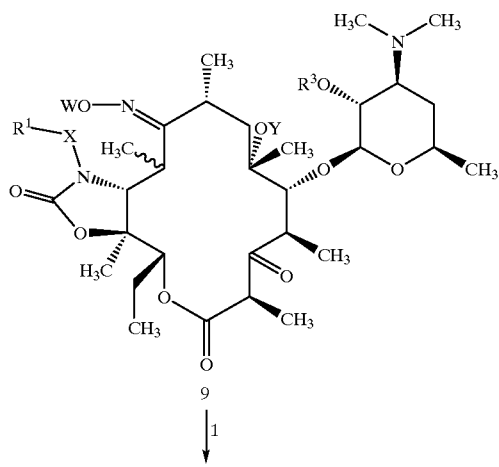

9

↓1

Scheme 6 illustrates the general synthesis of the compounds of formula 6. In Scheme 6, the starting compound of formula 10 can be prepared as described in Scheme 2. In step 1 of Scheme 6, the compounds of formula 10 can be converted to those of formula 24 via Beckmann rearrangement as described by Yamamoto et al (B. M. Trost, Comprehensive Organic Transformations, Volume 4, pp. 763–793). The compounds of formula 24, wherein Z is H, can be prepared directly by treating the compounds of formula 10 with metal hydride reagents, in a solvent such as $CH_2Cl_2$, following substantially the same procedures of Yamamoto et al (Tetrahedron Letters, 1983, 24, 4711). The preferred metal hydride reagent is diisobutylaluminium hydride. The compounds of formula 23, wherein Z is not H, can be obtained by treating the compounds of formula 10 with organometallic reagents such as Z₃Al, wherein Z is defined as above, following substantially the same procedures of Yamamoto et al (J. Amer. Chem. Soc., 1981, 7368). In step 2 of Scheme 6, the transformation of 23 to 24 can be achieved either by catalytic hydrogenation or metal hydride reduction such as diisobutylaluminium hydride. In step 3 of Scheme 6, the conversion of the compound of formula 24 to the compounds of formula 6 can be effected by alkylation.

Scheme 6

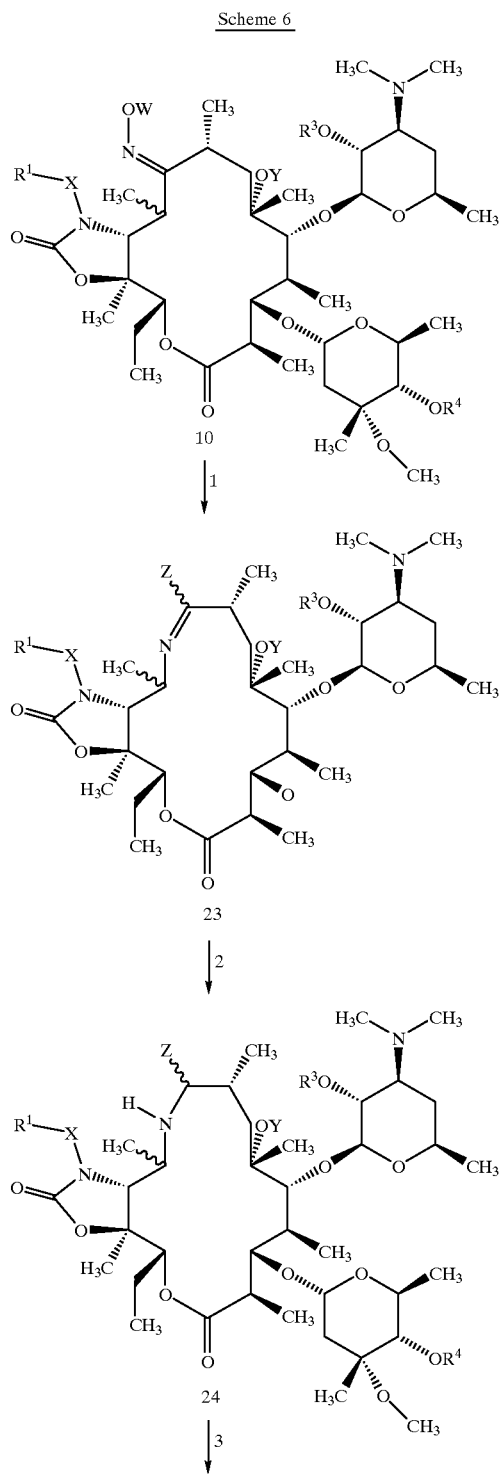

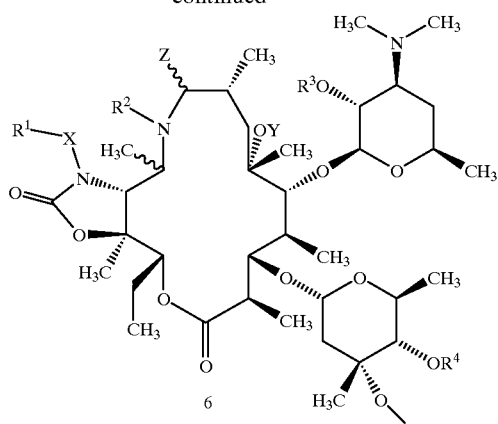

Scheme 7 illustrates the general synthesis of the compounds of formula 7. In Scheme 7, the starting compound of formula 11 can be prepared as described in Scheme 3. In step 1 of Scheme 7, the compounds of formula 11 can be converted to those of formula 26 via Beckmann rearrangement as described by Yamamoto et al (B. M. Trost, Comprehensive Organic Transformations, Volume 4, pp. 763–793). The compounds of formula 26, wherein Z is H, can be prepared directly by treating the compounds of formula 11 with metal hydride reagents in a solvent such as CH₂Cl₂ following substantially the same procedures of Yamamoto et al (Tetrahedron Letters, 1983, 24, 4711). The preferred metal hydride reagent is diisobutylaluminium hydride. The compounds of formula 25, wherein Z is not H, can be obtained by treating the compounds of formula 11 with organometallic reagents such as Z₃Al, wherein Z is defined as above, following substantially the same procedures of Yamamoto et al (J. Amer. Chem. Soc., 1981, 7368). In step 2 of Scheme 7, the transformation of 25 to 26 can be achieved either by catalytic hydrogenation or metal hydride reduction such as diisobutylaluminium hydride. In step 3 of Scheme 7, the conversion of 24 to the compounds of formula 6 can be effected by alkylation.

Scheme 7

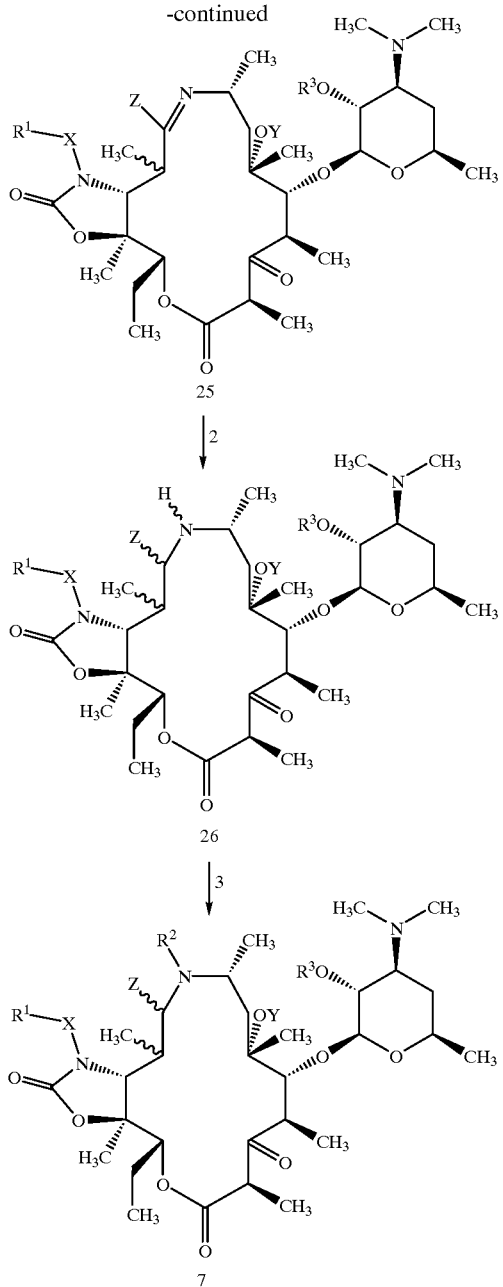

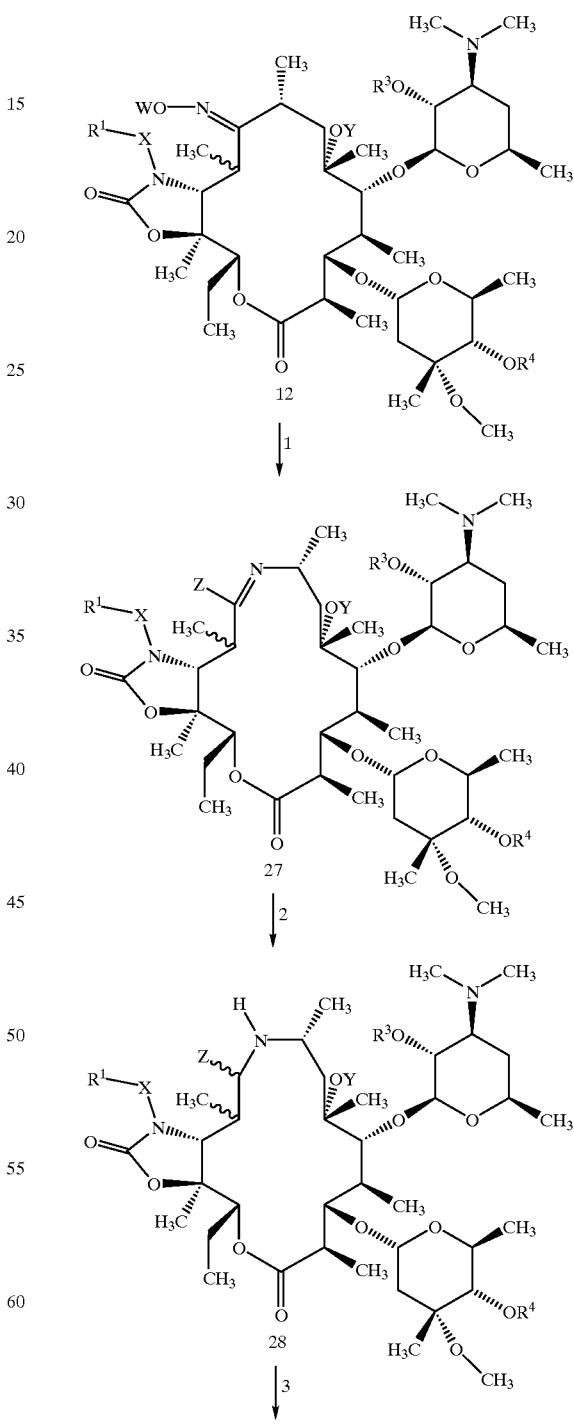

defined as above, following substantially the same procedures of Yamamoto et al (J. Amer. Chem. Soc., 1981, 7368). In step 2 of Scheme 8, the transformation of the compounds of formula 27 to the compounds of formula 28 can be achieved either by catalytic hydrogenation or metal hydride reduction such as diisobutylaluminium hydride. In step 3 of Scheme 8, the conversion of the compound of formula 28 to the compounds of formula 8 can be effected by alkylation.

Scheme 8

Scheme 8 illustrates the general synthesis of the compounds of formula 8. In Scheme 8, the starting compound of formula 12 can be prepared as described in Scheme 4. In step 1 of Scheme 8, the compounds of formula 12 can be converted to those of formula 28 via Beckmann rearrangement as described by Yamamoto et al (B. M. Trost, Comprehensive Organic Transformations, Volume 4, pp763–793). The compounds of formula 28, wherein Z is H, can be prepared directly by treating the compounds of formula 12 with metal hydride reagents in a solvent such as $CH_2Cl_2$ following substantially the same procedures of Yamamoto et al (Tetrahedron Letters, 1983, 24, 4711). The preferred metal hydride reagent is diisobutylaluminium hydride. The compounds of formula 27, wherein Z is not H, can be obtained by treating the compounds of formula 12 with organometallic reagents such as $Z_3Al$, wherein Z is

51

-continued

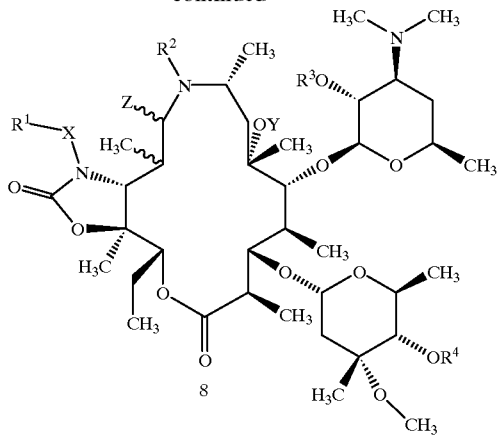

8

52

Schemes 9, 10, 11 and 12 describe the preparation of 6-O-methyl derivatives of 3-keto-azalides and 3-keto-isoazalides. In the Schemes, "Ac" means acetyl, "Et" means ethyl, "EDC" means 1-(3-dimethylaminopropyl)-3-ethyl-carbodiimide hydrochloride, "DMSO" means dimethyl sulfoxide, and "PTFA" means pyridinium trifluoroacetate. The N9-methyl-6-O-methyl9-deoxy-9a-aza-erythromycin A (6-O-methyl-azithromycin) has been prepared before via a direct methylation method familiar to those skilled in the art. The reactions illustrated in schemes 9 through 11 are described in the Experimentals provided below, in particular examples 1 through 13.

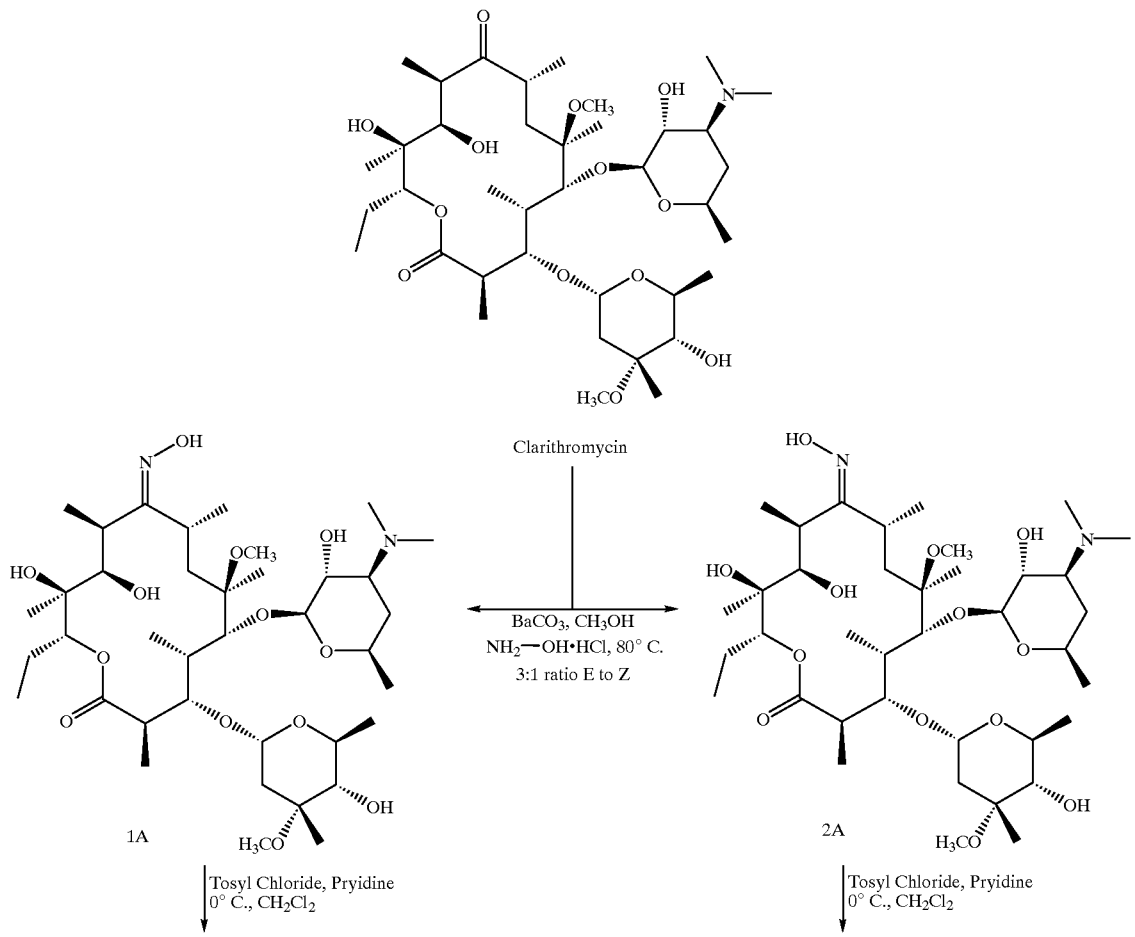

Scheme 9

53                                54
-continued
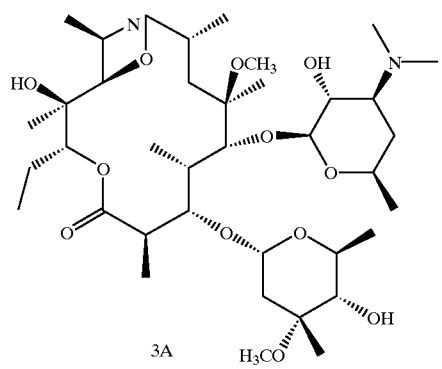
3A
HOAc, PtO2
50 PSI H2
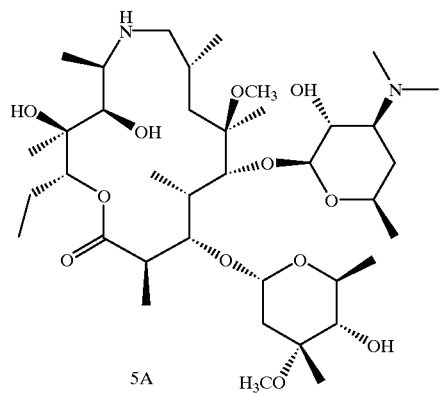
5A
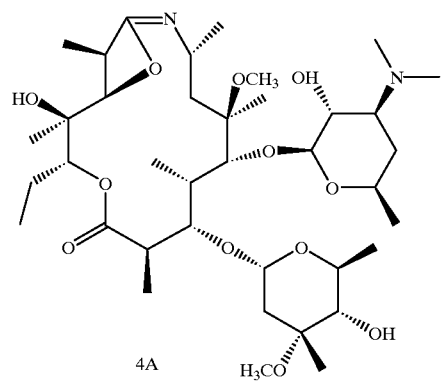
4A
NaBH4, 0° C.
CH3OH
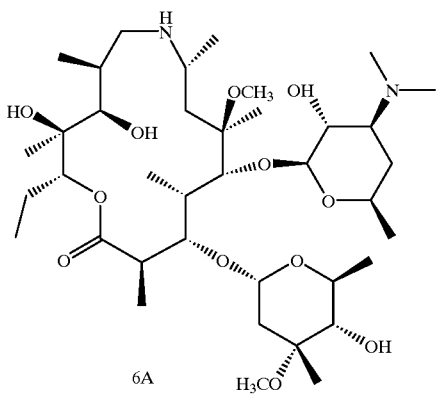
6A
Scheme 10
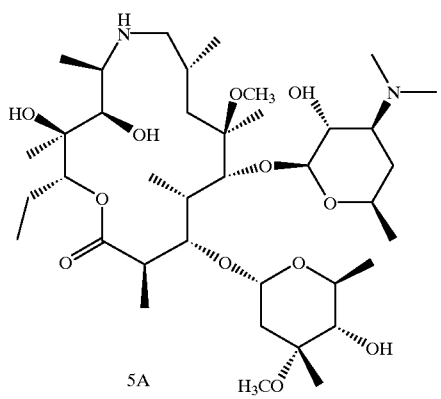
5A
HCHO, NaOAc
CH2Cl2, NaB(OAc)3H
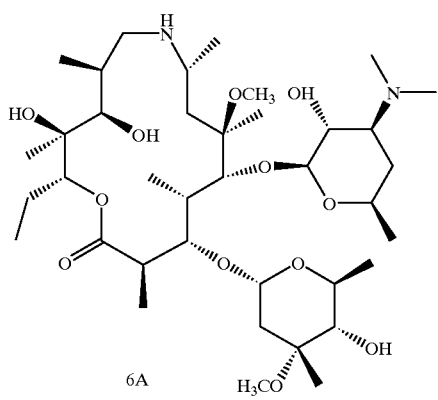
6A
HCHO, NaB(OAc)3H
ClCH2CH2Cl -continued
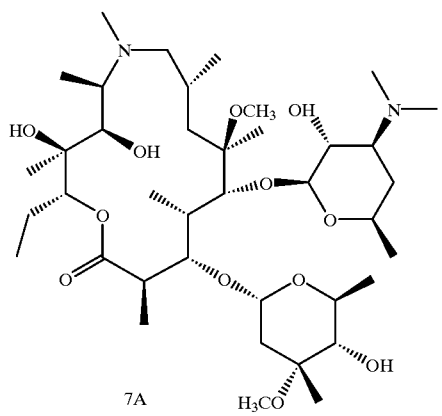
7A
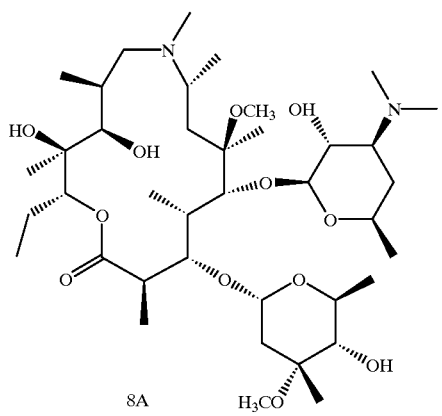
8A
Scheme 11
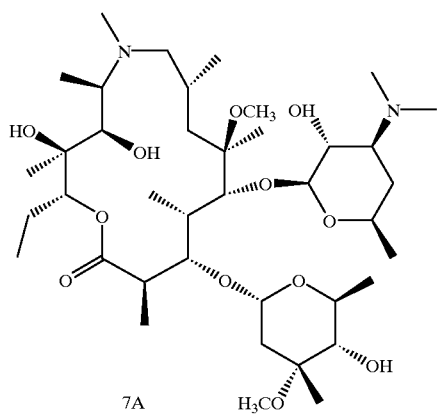
7A
1) 2M HCl, CH₃OH
2) Ac₂O, CH₂Cl₂
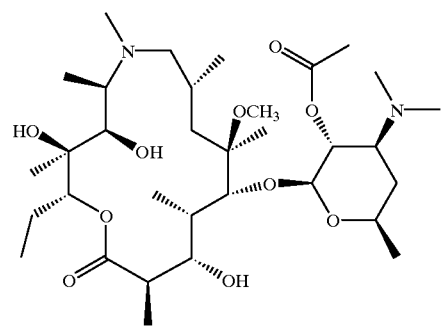
12A
EDC, DMSO,
PTFA, CH₂Cl₂
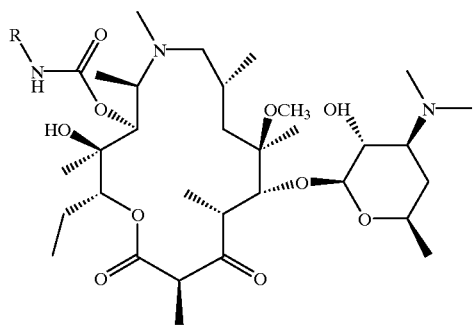
14A, 15A
R = Benzyl
1) R—NCO, Et₃N
   Toluene, 80° C.
2) CH₃OH, 23° C.
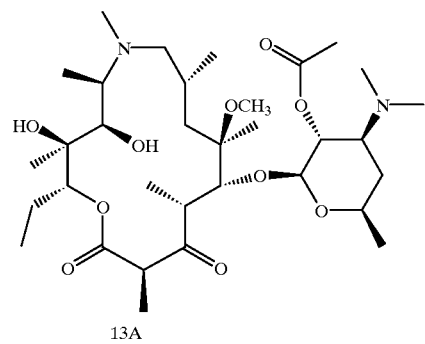
13A Scheme 12

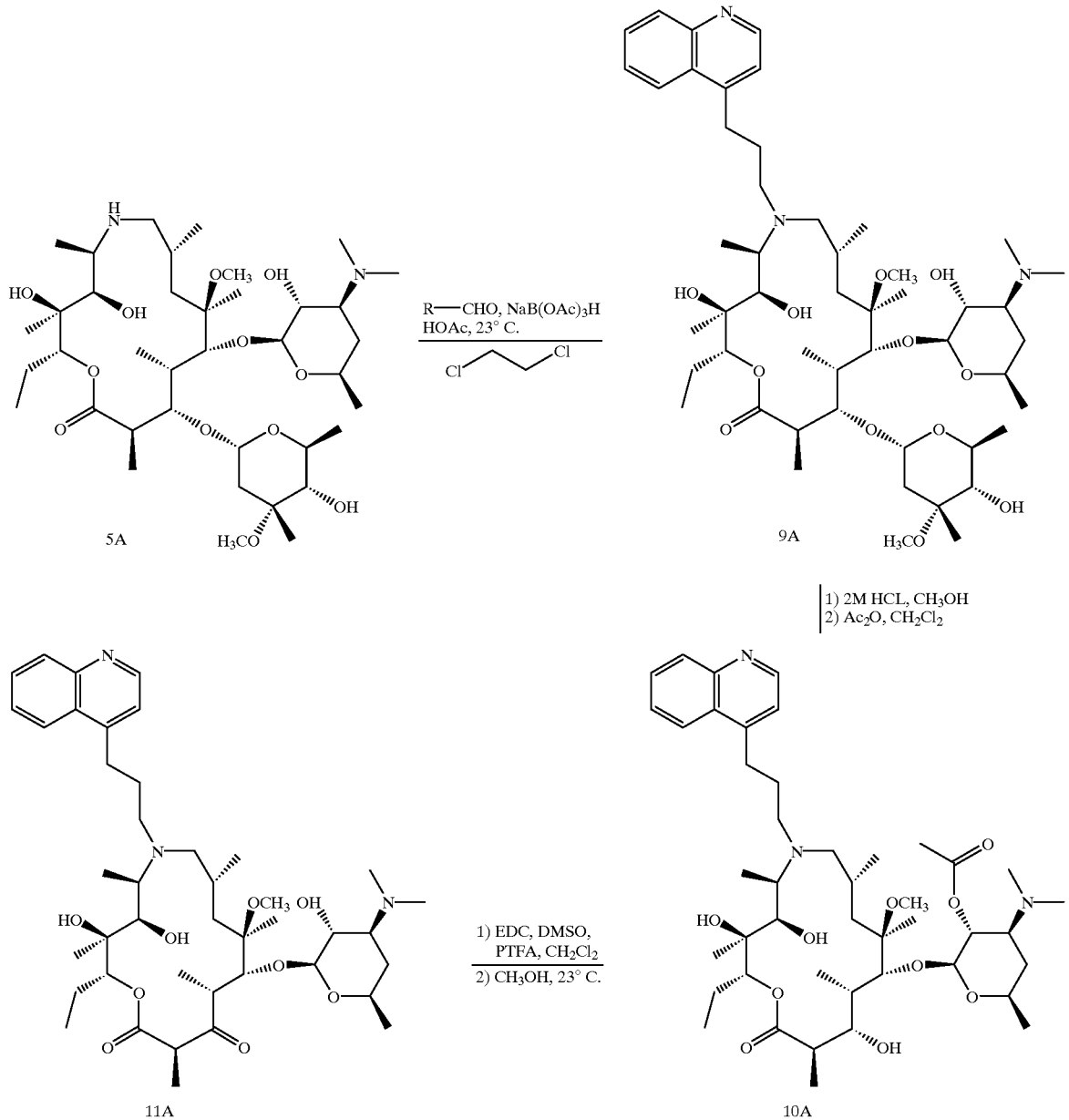

EXPERIMENTALS

EXAMPLE 1

PREPARATION OF 1A AND 2A FROM CLARITHROMYCIN 60.11 mmol of Clarithromycin are dissolved in 350 ml of absolute $CH_3OH$ and treated with 10 equivalents of $BaCO_3$ and N-hydroxlyamine hydrochloride. The resulting mixture is heated to reflux for a period of 10 days. The mixture is cooled to room temperature and filtered to remove inorganics. The filtrate is concentrated by reduced pressure to a yellow foam. The foam is partitioned between $EtOAct/H_2O$ and the pH is adjusted to 10 with 5M NaOH, After a 30 minute stir, the layers are separated and the aqueous is further extracted with 3×300 ml EtOAc. The combined organics are dried over $MgSO_4$, filtered and concentrated to a foam.

Separation of 1A from 2A:

The mixture of isomers are taken up in 500 ml of $CH_2Cl_2$ and stirred at 23° C. for 30 minutes. The formed precipitate is filtered off and washed with $CH_2Cl_2$ then dried under high vacuum to give the title compound 2A (13.72 g). The filtrate is concentrated by reduced pressure to a white solid and dried under high vacuum to give the title compound 1A (30.32 g). Overall combined yield of 44.04 g in 96%.

EXAMPLE 2

Preparation of 3A from E-oxime 1A 30.99 mmol of E-oxime 1A are dissolved in 300 ml of anhydrous $CH_2Cl_2$ and cooled to 0° C. Added are 1 equivalent of anhydrous pyridine and toluene-4-sulfonylchloride. After 5 hours, the reaction is poured into 300 ml of 5%

$Na_2CO_3$ solution; the layers are separated and the aqueous is further extracted with 2×200 ml $CH_2Cl_2$. The combined organics are washed with 300 ml of saturated NaCl and dried over anhydrous $K_2CO_3$. Silica gel chromatography in 5–10% $CH_3OH/CH_2Cl_2$ 0.5–1.0% $NH_4OH$ gives the title compound 3A as a white foam 19.50 g in 85% yield.

EXAMPLE 3

Preparation of 4A from Z-oxime 2A 1.32 mmol of Z-oxime 2A are dissolved 15 ml of anhydrous $CH_2Cl_2$ and cooled to 0° C. Added are 1 equivalent of anhydrous pyridine and toluene-4-sulfonylchloride. After 4 hours, the reaction is poured into 15 ml of 5% $Na_2CO_3$ solution; the layers are separated and the aqueous is further extracted with 2×20 ml $CH_2Cl_2$. The combined organics are washed with 50 ml of saturated NaCl and dried over anhydrous $K_2CO_3$. Silica gel chromatography in 3.5–6% $CH_3OH/CH_2Cl_2$ 0.3–0.5% $NH_4OH$ gives the title compound 4A as a white foam 0.340 mg in 35% yield.

EXAMPLE 4

Reduction of Cyclic Iminoether 3 to Azalide 5A 28.86 mmol of 3A are dissolved in 150 ml of glacial acetic acid and treated with 30% (w/w) $PtO_2$. The resulting mixture is placed on a Parr shaker apparatus under 50 PSI hydrogen for 24 hours. The reaction mixture is filtered through a plug of celite and rinsed through with 500 ml of absolute $CH_3OH$, The filtrate is concentrated by reduced pressure and the remaining residue is partitioned between $CH_2Cl_2/H_2O$ and the pH is adjusted to 10 with 5M NaOH, The layers are separated and the aqueous is further extracted with 3×300 ml $CH_2Cl_2$. The combined organics are dried over anhydrous $K_2CO_3$Silica gel chromatography in 8–10% $CH_3OH/CH_2Cl_2$ 0.8–1.0% $NH_4OH$ gives the title compound 5A as a white foam 14.0 g in 65% yield.

EXAMPLE 5

Reduction of Cyclic Iminoether 4 to Isoazalide 6A 0.514 mmol of 4A are dissolved in 5 ml of absolute $CH_3OH$ and cooled to 0° C. Added are 3 equivalents of sodium borohydride. After 15 ml nutes, the reaction is diluted by 1 volume with $H_2O$ and the pH adjusted to 3 with 1N HCl. The reaction is stirred for 20 minutes then poured into 25 ml of 5% $Na_2CO_3$ solution, extracted with 3×25 ml $CH_2Cl_2$ and dried over anhydrous $K_2CO_3$. Silica gel chromatography in 8–10% $CH_3OH/CH_2Cl_2$ 0.3–0.5% $NH_4OH$ gives the title compound 6A as a white foam 0.374 g in 97% yield.

EXAMPLE 6

N-methylation of Azaude 5A 0.149 mmol of SA are dissolved in 3 ml of anhydrous $CH_2Cl_2$ and treated with 1.1 equivalents of 37% aqueous formaldehyde, sodium triacetoxyborohydride and sodium acetate trihydrate. After 1 hour at 23° C., the reaction is concentrated. The residue is taken into 1:1 $CH_3OH/H_2O$ and the pH is adjusted to 4 with 1N HCl. The reaction is stirred for 20 minutes then poured into 10 ml of 5% $Na_2CO_3$ solution, extracted with 3×10 ml $CH_2Cl_2$ and dried over anhydrous $K_2CO_3$. Silica gel chromatography in 6–10% $CH_3OH/CH_2Cl_2$ 0.5–1.0% $NH_4OH$ gives the title compound as a colorless film 0.043 g in 38% yield.

EXAMPLE 7

N-methylation of Isoazalide 6A 0.446 mmol of 5A are dissolved in 4 ml of dichloroethane and treated with 3 equivalents of 37% aqueous formaldehyde and 4 equivalents of sodium triacetoxyborohydride. After 1 hour at 23° C., the reaction is concentrated. The residue is taken into 1:1 $CH_3OH/H_2O$ and the pH is adjusted to 4 with 1N HCl. The reaction is stirred for 20 ml nutes then poured into 10 ml of 5% $Na_2CO_3$ solution, extracted with 3×10 ml $CH_2Cl_2$ and dried over anhydrous $K_2CO_3$. Filtered, concentrated to a foam and triturated with $H_2O$. Upon filtration, the title compound is obtained as a white solid 0.328 g in 96% yield.

EXAMPLE 8

Preparation of 9 from Azalide 5A 0.667 mmol of 5A are dissolved in 10 ml of dichloroethane and treated with 3 equivalents of the appropriate aldehyde, 4 equivalents of sodium triacetoxyborohydride and 4 equivalents of acetic acid. After stirring at 23° C. for 24 hours, the reaction is concentrated. The residue is taken into $CH_3OH/H_2O$ and the pH is adjusted to 4 with 1N HCl. The reaction is stirred for 20 minutes then poured into 25 ml of 5% $Na_2CO_3$ solution, extracted with 3×25 ml $CH_2Cl_2$ and dried anhydrous $K_2CO_3$. Silica gel chromatography in 6–10% $CH_3OH/CH_2Cl_2$ 0.6–1.0% $NH_4OH$ gives the title compound as a foam 0.097 g in 16% yield.

EXAMPLE 9

Preparation of 10A from 9A:

0.105 mmol of 9A are taken into 3 ml of $CH_3OH$ and treated with 4 equivalents of 2N HCl. After 5 hours at 23° C., the pH is adjusted to 10 with 5M NaOH extracted with 3×5 ml $CH_2Cl_2$ and dried over anhydrous $K_2CO_3$. Silica gel chromatography in 8% $CH_3OH/CH_2Cl2$ 0.8% $NH_4OH$ gives the desired hydrolyzed intermediate 0.080 g in 100% yield. 0.105 mmol of the above intermediateare dissolved is 3 ml of anhydrous $CH_2Cl_2$ and treated with 1 equivalent of acetic anhydride. After 2 hours at 23° C., the reaction is poured into 5% $Na_2CO_3$ solution. The layers are separated and the aqueous is further extracted with 2×3 ml $CH_2Cl_2$ and the combined organics are dried, over ahydrous $K_2CO_3$. Silica gel chromatography in 4% $CH_3OH/CH_2Cl_2$ 0.4% $NH_4OH$ gives the title compound 10A as a foam 0.053 g in 62% yield.

EXAMPLE 10

Preparation of N-alkylated Aza-ketolide 11A from 1A 0.066 mmol of 10A are dissolved in 2 ml of anhydrous $CH_2Cl_2$ and treated with 10 equivalents of anhydrous methyl sulfoxide, 4 equivalents of 1-(3-dimethylaminopropyl)-3-ethylcarbodiimide hydrochloride and 4 equivalents of pyridinium trifluoracetate. After 2 hours at 23° C., the reaction is diluted by 1 volume with $H_2O$ and the pH is adjusted to 10 with 1M NaOH, The reaction is stirred for 20 minutes. The layers are separated and the aqueous is further extracted with 2×5 ml $CH_2Cl_2$ and the combined organics are dried over anhydrous $K_2CO_3$. Silica gel chromatography in 3% $CH_3OH/CH_2Cl_2$ 0.3% $NH_4OH$ and deacetylation in absolute $CH_3OH$ gives the title compound 11A as a colorless film 0.023 g in 46% yield.

EXAMPLE 11

Preparation of 12A from N-methyl Azalide 7A 2.62 mmol of 7A are dissolved in 30 ml of $CH_3OH$ and the pH is adjusted to 1 with 2N HCl. After stirring 20 hours at 23° C., the reaction is diluted by 1 volume with $H_2O$ and the pH is adjusted to 10 with 5M NaOH, The solution is extracted with 3×50 ml $CH_2Cl_2$ and dried over anhdrous $K_2CO_3$. Silica gel chromatography in 8–10% $CH_3OH/CH_2Cl_2$ 0.8–1.5% $NH_4OH$ gives t hydrolyzed intermediate as a white foam 1.40 g in 88% yield. 4.6 mmol of the above intermediate are dissolved in 50 ml of anhydrous $CH_2Cl_2$ and treated with 1 equivalent of acetic anhydride. After stirring 20 hours at 23° C., the reaction is diluted by 1 volume with $H_2O$ and the pH is adjusted to 10 with 1M NaOH, Separated the layers. The aqueous is further extracted with 2×50 ml of $CH_2Cl_2$ and the combined organics are dried on $K_2CO_3$. Silica gel chromatography in 3% $CH_3OH/CH_2Cl_2$ 0.3% $NH_4OH$ gives the title compound 12A as a white foam 2.29 in 74% yield.

EXAMPLE 12

Oxidation of 12A TO Aza-ketolide 13A 2.21 mmol of 12A are dissolved in 20 ml of anhydrous $CH_2Cl_2$ and treated with 10 equivalents of anhydrous methyl sulfoxide, 4 equivalents of 1-(3-dimethylaminopropyl)-3-ethylcarbodiimide hydrochloride and 4 equivalents of pyridinium trifluoracetate. After 2 hours at 23° C., the reaction is diluted by 1 volume with $H_2O$ and the pH is adjusted to 10 with 1M NaOH, The reaction is stirred for 20 minutes. The layers are separated and the aqueous is further extracted with 2×25 ml $CH_2Cl_2$ and the combined organics are dried over anhydrous $K_2CO_3$. Silica gel chromatography in 8% $CH_3OH/CH_2Cl_2$ 0.8% $NH_4OH$ gives the title compound 13A as a white foam 0.761 g in 53% yield.

EXAMPLE 13

Preparation of Carbamate 14 from Aza-ketilide 13

0.161 mmol of 13A are dissolved in 3 ml of anhydrous toluene and treated with 2 equivalents of anhydrous triethylamine and 2 equivalents of benzyl isocyanate. After 30 hours at 85° C., the reaction is cooled to 23° C. and poured into 5% $Na_2CO_3$ solution. The resulting solution is extracted with 3×5 ml EtOAc and the combined organics are dried over anhydrous $MgSO_4$. Concentration gives the desired acetate protected intermediate as a white foam. The above intermediate is dissolved in 25 ml of absolute $CH_3OH$, After 20 hours at 23° C., the reaction is concentrated to a film. Silica gel chromatography in 2% $CH_3OH/CH_2Cl_2$ 0.1% $NH_4OH$ gives the title compound 14A as a colorless film 0.077 g in 65% yield.

The examples provided below refer to compound formulas illustrated in the Summary of the Invention and in Schemes 1 through 8.

EXAMPLE 14

Compound of Formula 1: $R^2=R^3=H$, Y=Me, X is Taken Together with $R^1$ to form N=CH—Ph To a solution of the compound of formula 12 (1.0 g), wherein $R^3=H$, Y=Me, X is taken together with $R^1$ to form N=CH—Ph, in $CH_2Cl_2$ (15 mL) and pyridine (7 mL) at room temperature was added p-tosyl chloride (892 mg) and the resulting solution was stirred at room temperature for 16 hours. Saturated $NaHCO_3$ was added followed by $CH_2Cl_2$, and the aqueous layer was extracted with $CH_2Cl_2$ and the combined organic layers were washed with brine, dried over $MgSO_4$, and concentrated. The crude product was purified by silica gel flash chromatography (95.5% $CH_2Cl_2$/4% MeOH/0.5% $NH_3.H_2O$) to afford the title compound as a white solid.

MS: m/z 731 (M+H).

EXAMPLE 15

Compound of Formula 1: $R^2=R^3=R^1=H$, Y=Me, X=NH

To a solution of the compound of formula 1 (150 mg), wherein $R^2=R^3=H$, Y=Me, X is taken together with $R^1$ to form N=CH—Ph, in MeOH/$H_2O$/HOAc (21/2/0.25) (23 mL) was added $Pd(OH)_2$ (150 mg) and the resulting suspension was hydrogenated at 40 psi for 15 hours. The reaction mixture was filtered through a pad of Celite, MeOH was evaporated in vacuo, and saturated $NaHCO_3$ was added followed by $CH_2Cl_2$. The organic layer was separated, the aqueous layer was extracted with $CH_2Cl_2$ and the combined organic layers were washed with brine, dried over $MgSO_4$, and concentratedto give the title compound as a white solid (125 mg).

MS: m/z 643 (M+H).

EXAMPLE 16

Compound of Formula 1: $R^2=R^3=H$, Y=Me, X is taken together with $R^1$ to form —N=CH($CH_2$)$_2$—(3-qulnolin-4-yl)

To a solution of the compound of formula 1 (30 mg), wherein, $R^2=R^3=R^1=H$, Y=Me, X=NH, in toluene (0.5 mL) was added 3-(4-quinolinyl)propionaldehyde (13 mg) and the resulting solution was heated at 90° C. for 17 hours. Toluene was removed in vacuo to give the title compound as a white solid.

MS: m/z 810 (M+H).

EXAMPLE 17

Compound of Formula 1: $R^2=R^3=H$, Y=Me, X=NH, $R^1$=3-quinolin-4-yl-propyl To a solution of the compound of formula 1 (30 mg), $R^2=R^3=H$, Y=Me, X is taken together with $R^1$ to form —N=CH($CH_2$)$_2$—3(quinolin-4-yl), in MeOH (0.5 mL) were added HOAc (40 uL) and $NaBH_3CN$ (44 mg), and the resulting solution was stirred at room temperature for 17 hours. Methanol was removed in vacuo, sat. $NaHCO_3$ was added followed by $CH_2Cl_2$, the organic layer was separated, and the aqueous layer was extracted with $CH_2Cl_2$. The combined organic layers were washed with brine, dried over $MgSO_4$, and concentrated. The residue was purified by preparative TLC (89% $CH_2Cl_2$-9% MeOH-1% $NH_3.H_2O$) to afford the title compound as a white solid.

MS: m/z 812 (M+H).

EXAMPLE 18

Compound of Formula 2: $R^2=R^3=H$, $R^4=Ac$, Y=Me, X is taken together with $R^1$ to form N=CH—h To a solution of the compound of formula 15 (0.5 g), wherein $R^3=H$, Y=Me, $R^4=Ac$, X is taken together with $R^1$ to form N=CH—Ph, in $CH_2Cl_2$ (15 mL) and pyridine (3 mL) at room temperature was added p-tosyl chloride (309 mg) and the resulting solution was stirred at room temperature for 16 hours. Saturated $NaHCO_3$ was added followed by $CH_2Cl_2$, and the aqueous layer was extracted with $CH_2Cl_2$ and the combined organic layers were washed with brine, dried over $MgSO_4$, and concentrated. The crude product was purified by silica gel flash chromatography (95.5% $CH_2Cl_2$/ 4% MeOH/0.5% $NH_3.H_2O$) to afford the title compound as a white solid (314 mg).

MS: m/z 933 (M+H).

EXAMPLE 19

Compound of formula 2: $R^2=R^3=R^1\odot H$, $R^4=Ac$, Y=Me, X=NH

To a solution of the compound of formula 2 (30 mg), wherein $R^2=R^3=H$, $R^4=Ac$, Y=Me, X is taken together with $R^1$ to form N=CH—P, in $MeOH/H_2O/HOAc$ (21/2/ 0.25) (1.5 mL) was added $Pd(OH)_2$ (150 mg) and the resulting suspension was hydrogenated at 40 psi for 15 hours. The reaction mixture was filtered through a pad of Celite, MeOH was evaporated in vacuo, and saturated $NaHCO_3$ was added followed by $CH_2Cl_2$. The organic layer was separated, the aqueous layer was extracted with $CH_2Cl_2$ and the combined organic layers were washed with brine, dried over $MgSO_4$, and concentratedto give the title compound as a white solid (125 mg).

MS: m/z 845 (M+H).

The compounds of the present invention may have asymmetric carbon atoms. Such diasteromeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereomric mixture by reaction with an appropriate optically active compound (e.g., alcohol), separating the diastereomers and converting (e.g., hydrolyzing) the individual diastereomers to the corresponding pure enantiomers. All such isomers, including diastereomer mixtures and pure enantiomers are considered as part of the invention. The compounds of formulae 1–8 that are basic in nature are capable of forming a wide variety of different salts with various inorganic and organic acids. Although such salts must be pharmaceutically acceptable for administration to animals, it is often desirable in practice to initially isolate the compound of formulae 1–8 from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of the formulae 1–8 that are acidic in nature, are capable of forming base salts with various pharmacologically acceptable cations. Examples of such salts include the alkali metal or alkaline-earth metal salts and particularly, the sodium and potassium salts. These salts may be prepared by conventional techniques. The chemical bases which are used as reagents to prepare the pharmaceutically acceptable base salts of this invention are those which form non-toxic base salts with the acidic compounds of formulae 1–8. Such non-toxic base salts include those derived from such pharmacologically acceptable cations as sodium, potassium calcium and magnesium, etc. These salts can be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The activity of the compounds of the present invention against bacterial and protozoa pathogens is demonstrated by the compound's ability to inhibit growth of defined strains of human (Assay I) or animal (Assays II to VII) pathogens.

Assay I

Assay I, described below, employs conventional methodology and interpretation criteria and is designed to provide direction for chemical modifications that may lead to compounds that circumvent defined mechanisms of macrolide resistance. In Assay I, a panel of bacterial strains is assembled to include a variety of target pathogenic species, including representatives of macrolide resistance mechanisms that have been characterized. Use of this panel enables the chemical structure/activity relationship to be determined with respect to potency, spectrum of activity, and structural elements or modifications that may be necessary to obviate resistance mechanisms. Bacterial pathogens that comprise the screening panel are shown in the table below. In many cases, both the macrolide-susceptible parent strain and the macrolide-resistant strain derived from it are available to provide a more accurate assessment of the compound's ability to circumvent the resistance mechanism. Strains that contain the gene with the designation of ermA/ermB/ermC are resistant to macrolides, lincosamides, and streptogramin B antibiotics due to modifications (methylation) of 23S rRNA molecules by an Erm methylase, thereby generally prevent the binding of all three structural classes. Two types of macrolide efflux have been described; msrA encodes a component of an efflux system in staphylococci that prevents the entry of macrolides and streptogramins while mefA/E encodes a transmembrane protein that appears to efflux only macrolides. Inactivation of macrolide antibiotics can occur and can be mediated by either a phosphorylation of the 2'-hydroxyl (mph) or by cleavage of the macrocyclic lactone (esterase). The strains may be characterized using conventional polymerase chain reaction (PCR) technology and/or by sequencing the resistance determinant. The use of PCR technology in this application is described in J. Sutcliffe et al., "Detection Of Erythromycin-Resistant Determinants By PCR", Antimicrobial Agents and Chemotherapy, 40(11), 2562–2566 (1996). The antibacterial assay is performed in microtiter trays and interpreted according to *Performance Standards for Antimicrobial Disk Susceptibility Tests—Sixth Edition; Approved Standard*, published by The National Committee for Clinical Laboratory Standards (NCCLS) guidelines; the minimum inhibitory concentration (MIC) is used to compare strains. acr AB or acr AB-like indicates that an intrinsia multidrug efflux pump exists in the strain. Compounds are initially dissolved in dimethylsulfoxide (DMSO) as 40 mg/ml stock solutions.

| Strain Designation | Macrolide Resistance Mechanism(s) |
| --- | --- |
| Staphylococcus aureus 1116 | susceptible parent |
| Staphylococcus aureus 1117 | ermB |
| Staphylococcus aureus 0052 | susceptible parent |
| Staphylococcus aureus 1120 | ermC |
| Staphylococcus aureus 1032 | msrA, mph, esterase |
| Staphylococcus hemolyticus 1006 | msrA, mph |
| Streptococcus pyogenes 0203 | susceptible parent |
| Streptococcus pyogenes 1079 | ermB |
| Streptococcus pyogenes 1062 | susceptible parent |
| Streptococcus pyogenes 1061 | ermB |
| Streptococcus pyogenes 1064 | mefA |
| Streptococcus agalactiae 1024 | susceptible parent |
| Streptococcus agalactiae 1023 | ermB |
| Streptococcus pneumoniae 1016 | susceptible |
| Streptococcus pneumoniae 1046 | ermB |
| Streptococcus pneumoniae 1095 | ermB |
| Streptococcus pneumoniae 1175 | mefE |
| Haemophilus influenzae 0085 | susceptible; acr AB-like |
| Haemophilus influenzae 0131 | susceptible; acr AB-like |
| Moraxella catarrhalis 0040 | susceptible |
| Moraxella catarrhalis 1055 | erythromycin intermediate resistance |
| Escherichia coli 0266 | susceptible; acr AB |
| Haemophilus influenzae 1100 | susceptible; acr AB-like |

Assay II is utilized to test for activity against *Pasteurella multocida* and Assay III is utilized to test for activity against *Pasteurella haemolytica*.

Assay II

This assay is based on the liquid dilution method in microliter format A single colony of *P. multocida* (strain 59A067) is inoculated into 5 ml of brain heart infusion (BHI) broth. The test compounds are prepared by solubilizing 1 mg of the compound in 125 $\mu$l of dimethylsulfoxide (DMSO). Dilutions of the test compound are prepared using uninoculated BHI broth. The concentrations of the test compound used range from 200 $\mu$g/ml to 0.098 $\mu$g/ml by two-fold serial dilutions. The *P. multocida* inoculated BHI is diluted with uninoculated BHI broth to make a $10^4$ cell suspension per 200 $\mu$l. The BHI cell suspensions are mixed with respective serial dilutions of the test compound, and incubated at 37° C. for 18 hours. The minimum inhibitory concentration (MIC) is equal to the concentration of the compound exhibiting 100% inhibition of growth of *P. multocida* as determined by comparison with an uninoculated control.

Assay III

This assay is based on the agar dilution method using a Steers Replicator. Two to five colonies isolated from an agar plate are inoculated into BHI broth and incubated overnight at 37° C. with shaking (200 rpm). The next morning, 300 $\mu$l of the fully grown *P. haemolytica* preculture is inoculated into 3 ml of fresh BHI broth and is incubated at 37° C. with shaking (200 rpm). The appropriate amounts of the test compounds are dissolved in ethanol and a series of two-fold serial dilutions are prepared. Two ml of the respective serial dilution is mixed with 18 ml of molten BHI agar and solidified. When the inoculated *P. haemolytca* culture reaches 0.5 McFarland standard density, about 5 $\mu$l of the *P. haemolytica* culture is inoculated onto BHI agar plates containing the various concentrations of the test compound using a Steers Replicator and incubated for 18 hours at 37° C. Initial concentrations of the test compound range from 100–200 $\mu$g/ml. The MIC is equal to the concentration of the test compound exhibiting 100% inhibition of growth of *P. haemolytica* as determined by comparison with an uninoculated control.

The in vivo activity of the compounds of formula (I) can be determined by conventional animal protection studies well known to those skilled in the art, usually carried out in mice. Mice are allotted to cages (10 per cage) upon their arrival, and allowed to acclimate for a minimum of 48 hours before being used. Animals are inoculated with 0.5 ml of a $3\times10^3$ CFU/ml bacterial suspension (*P. multocida* strain 59A006) intraperitoneally. Each experiment has at least 3 non-medicated control groups including one infected with 0.1×challenge dose and two infected with 1×challenge dose; a 10×challenge data group may also be used. Generally, all mice in a given study can be challenged within 30–90 ml nutes, especially if a repeating syringe (such as a Cornwall® syringe) is used to administer the challenge. Thirty minutes after challenging has begun, the first compound treatment is given. It may be necessary for a second person to begin compound dosing if all of the animals have not been challenged at the end of 30 ml nutes. The routes of administration are subcutaneous or oral doses. Subcutaneous doses are administered into the loose skin in the back of the neck whereas oral doses are given by means of a feeding needle. In both cases, a volume of 0.2 ml is used per mouse. Compounds are administered 30 minutes, 4 hours, and 24 hours after challenge. A control compound of known efficacy administered by the same route is included in each test Animals are observed daily, and the number of survivors in each group is recorded. The *P. multocida* model monitoring continues for 96 hours (four days) post challenge. The $PD_{50}$ is a calculated dose at which the compound tested protects 50% of a group of mice from mortality due to the bacterial infection which would be lethal in the absence of drug treatment Assay IV The in vivo activity of the compounds of formulae 1–8 can be determined by conventional animal protection studies well known to those skilled in the art, usually carried out in mice. Mice are allotted to cages (10 per cage) upon their arrival, and allowed to acclimate for a minimum of 48 hours before being used. Animals are inoculated with 0.5 ml of a $3\times10^3$ CFU/ml bacterial suspension (*P. multocida* strain 59A006) intraperitoneally. Each experiment has at least 3 non-medicated control groups including one infected with 0.1×challenge dose and two infected with 1×challenge dose; a 10×challenge data group may also be used. Generally, all mice in a given study can be challenged within 30–90 ml nutes, especially if a repeating syringe (such as a Cornwall® syringe) is used to administer the challenge. Thirty minutes after challenging has begun, the first compound treatment is given. It may be necessary for a second person to begin compound dosing if all of the animals have not been challenged at the end of 30 minutes. The routes of administration are subcutaneous or oral doses. Subcutaneous doses are administered into the loose skin in the back of the neck whereas oral doses are given by means of a feeding needle. In both cases, a volume of 0.2 ml is used per mouse. Compounds are administered 30 minutes, 4 hours, and 24 hours after challenge. A control compound of known efficacy administered by the same route is included in each test Animals are observed daily, and the number of survivors in each group is recorded. The *P. multocida* model monitoring continues for 96 hours (four days) post challenge.

The $PD_{50}$ is a calculated dose at which the compound tested protects 50% of a group of mice from mortality due to the bacterial infection which would be lethal in the absence of drug treatment Assay V Murine *Staphylococcus aureus* Intraperitoneal Infection Model Mice (female CF-1) are allotted to cages (10 per cage) upon their arrival, and allowed to acclimate for a minimum of 48 hours before being used. Mice are infected intraperitoneally with 0.5 ml of a 3 to 5×105 colony forming units (CFU)/ml log phase culture of *Staphylococcus aureus* strain UC 6097 in 5% hog gastric mucin. Each experiment has one infected, non-medicated control group. Generally, all mice in a given study can be challenged within 30 to 90 minutes, especially if a repeating syringe (such as a Cornwall® syringe) is used to administer the challenge culture. Thirty minutes after infection has begun, compound treatment is given. It may be necessary for a second person to begin compound dosing if all of the animals have not been challenged at the end of thirty minutes. Subcutaneous doses are administered into the loose skin in the back of the neck whereas oral doses are given by means of a feeding needle. In both cases, a volume of 0.2 ml is used per mouse. A control compound of known efficacy administered by the same route is included in each test. Animals are observed daily, and the number of survivors in each group is recorded for 72 hours (three days) post challenge. The PD50 is a calculated dose at which the compound tested protects 50% of a group of mice from mortality due to the bacterial infection which would be lethal in the absence of drug treatment.

Assay VI

Murine *Staphylococcus aureus* Intramammary Infection Model

Lactating mice (female CF-1 that gave birth 2 to 5 days prior to the day of infection) (female CF-1) are allotted to cages (I per cage) upon their arrival, and allowed to acclimate for 24–48 hours before being used. Mice are infected in the L4 mammary gland with 0.1 ml of a 300 to 450 colony forming units (CFU)Iml log phase culture of Staphylococcus aureus strain UC 6097. Each experiment has one infected, non-medicated control group. Thirty minutes after infection has begun, compound treatment is given. Subcutaneous doses are administered into the loose skin in the back of the neck whereas oral doses are given by means of a feeding needle. In both cases, a volume of 0.2 ml is used per mouse. The endpoint is the presence or absence of clinical mastitis symptoms and quantitation of bacterial numbers in the mammary glands five days after infection. Bacteria are quantitated by homogenizing the infected gland with 4 volumes of phosphate buffered saline for 30 seconds (Omni International, model TH). The homogenate and dilutions of the homogenate are plated on Brain Heart Infusion Agar, incubated at 37° C. overnight, and the colonies counted. The lower limit of detection is 50 CFU/gland. Infected, non-medicated mice have ~5×109 CFU/gland at the time of necropsy.

Assay VII

Determination Of MIC Of Fusobacterium necrophorum Isolated Using Anaerobic Plate Dilution Techniques Minimum inhibitory concentration (MIC) data may be collected from isolates of Fusobacterium necrophorum of cattle and sheep origin. The MIC values for Fusobacterium necrophorum are determined using plate dilution techniques and inoculation with a Steer's replicator. The procedures are those outlined in "Methods For Antimicrobial Susceptibility Testing Of Anaerobic Bacteria-Third Edition; Approved Standard" (vol. 13, no. 26, 1993) by the National Committee on Clinical Laboratory Standards (NCCLS). A total of 10 dilutions of the antimicrobials are tested as doubling dilutions of the drug (32 to 0.063 mcg/ml). Control strains of anaerobic bacteria (Clostridium perfringens ATCC 13124 and Bacteroides fragilis ATCC 25285) are used as controls on each inoculated plate.

The in vivo activity of the compounds of the present invention can be determined by conventional animal protection studies well known to those skilled in the art, usually carried out in rodents.

The compounds of formulae 1–8, and the pharmaceutically acceptable salts thereof (hereinafter "the active compounds"), may be adminstered through oral, parenteral, topical, or rectal routes in the treatment or prevention of bacterial or protozoa infections. In general, these compounds are most desirably administered in dosages ranging from about 0.2 mg per kg body weight per day (mg/kg/day) to about 200 mg/kg/day in single or divided doses (i.e., from 1 to 4 doses per day), although variations will necessarily occur depending upon the species, weight and condition of the subject being treated and the particular route of administration chosen. However, a dosage level that is in the range of about 4 mg/kg/day to about 50 mg/kg/day is most desirably employed. Variations may nevertheless occur depending upon the species of mammal, fish or bird being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects, provided that such larger doses are first divided into several small doses for administration throughout the day.

The active compounds may be administered alone or in combination with pharmaceutically acceptable carriers or diluents by the routes previously indicated, and such administration may be carried out in single or multiple doses. More particularly, the active compounds may be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the active compounds are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral adinistration, the active compound may be combined with various sweetening or flavoring agents, coloring matter or dyes, and, if so desired, emulsifying andlor suspending agents as well, together with such diluents as water, ethanol, propylene glycol, glycerin and various like combinations thereof.

For parenteral administration, solutions of an active compound in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques will known to those skilled in the art.

Additionally, it is also possible to administer the active compounds of the present invention topically and this may be done by way of creams, jellies, gels, pastes, patches, ointments and the like, in accordance with standard pharmaceutical practice.

For administration to animals other than humans, such as cattle or domestic animals, the active compounds may be administered in the feed of the animals or orally as a drench composition.

The active compounds may also be adminstered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The active compounds may also be coupled with soluble polymers as targetable drug carriers. Such polymers can indude polyvinylpyrrolidone, pyran copolymer, polyhydroxypropylmethacrylamide phenyl, polyhydroxyethylaspartamide-phenol, or polyethyleneoxide-polylysine substituted with palmitoyl-residues. Furthermore, the active compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross-linked or amphipathic block copolymers of hydrogels.

What is claimed is:

1. A compound of the formula 1

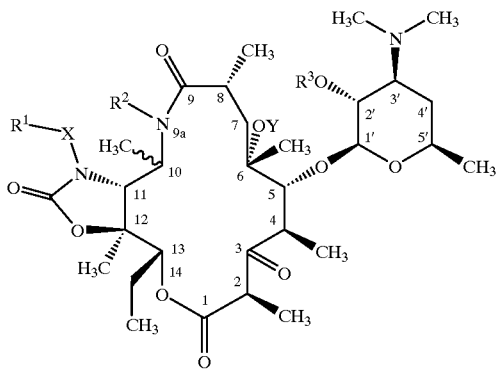

or a pharmaceutically acceptable salt thereof, wherein:

X is —O—, —$NR^5$—, or $(CR^5R^6)_g$, wherein g is 0 or 1 and wherein, when X is —$NR^5$—, $R^5$ and $R^2$ are taken together to form —$(CR^7R^8)$—;

or X is taken together with $R^1$ to form —N=$CR^7R^8$;

or X and $R^1$ are taken together to form a heterocyclic ring of the formula XI

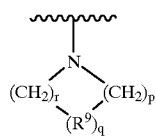

wherein in said ring of formula XI, r and p are each independently an integer ranging from 1 to 3, q is 0 or 1, and $R^9$ is —$CH_2$—, O, S, —C(O)—, —C(S)—, —$SO_2$—, —CH=CH—, —CH(OH)CH(OH)—, or —NH—; and wherein the $(CH_2)_r$ and $(CH_2)_p$ portions of said ring of formula XI are optionally substituted by 1 to 4 substituents and wherein each hydrogen atom of $R^9$ when $R^9$ is —$CH_2$—, —CH=CH—, —CH(OH)CH(OH)—, or —NH is optionally substituted by one substituent, said optional substituents being independently selected from the group consisting of —$C(O)OR^{10}$, —$OR^{10}$, —$C(O)R^{10}$, halo, nitro, cyano, 4–10 membered heterocyclic, —$R^{10}$, —$NR^{10}R^{11}$, —$NHC(O)R^{10}$, —$NHC(O)NR^{10}R^{11}$, $C_6$–$C_{10}$ aryl, 4–10 membered heterocyclic, —$S(O)_nR^{10}$, and —$SO_2NR^{10}R^{11}$, wherein n is an integer ranging from 0 to 2;

Y is $R^7$ or —$(CR^5R^6)_mR^{12}$, wherein m is an integer ranging from 0 to 6; and $R^5$ and $R^6$ may each independently vary when m is greater than 1;

$R^1$ is H, $R^7$, —$C(O)R^7$, —$C(O)R^{12}$, —$C(O)OR^7$, —$C(O)OR^{12}$, or —$(CR^5R^6)_mR^{12}$, wherein m is an integer ranging from 0 to 6;

$R^2$ is H or $C_1$–$C_{12}$ alkyl, wherein one or two carbons of said alkyl are optionally replaced by a heteroatom selected from the group consisting of O, S and N, and are optionally substituted by 1 to 3 substituents selected from the group consisting of —$C(O)OR^{10}$, —$OR^{10}$, —$C(O)R^{10}$, halo, nitro, cyano, 4–10 membered heterocyclic, —$R^{10}$, —$NR^{10}R^{11}$, —$NHC(O)R^{10}$, —$NHC(O)NR^{10}R^{11}$, $C_6$–$C_{10}$ aryl, 4–10 membered heterocyclic, —$S(O)_nR^{10}$, and —$SO_2NR^{10}R^{11}$, wherein n is an integer ranging from 0 to 2;

each $R^3$ is independently selected from the group consisting of H, —$C(O)R^{12}$ or $C_1$–$C_{18}$ alkanoyl, wherein in the alkyl portion of said alkanoyl one or two carbons optionally may be replaced by a heteroatom selected from O, S and N;

each $R^5$ and $R^6$ is independently H, halo, or $C_1$–$C_{10}$ alkyl and $R^5$ and $R^6$ may each independently vary when m is greater than 1;

each $R^7$ and $R^8$ is independently selected from H and $C_1$–$C_{18}$ alkyl, wherein one or two carbons of said alkyl are optionally replaced by a heteroatom selected from the group consisting of O, S and N, and are optionally substituted by 1 to 3 substituents selected from the group consisting of —$C(O)OR^{10}$, —$OR^{10}$, —$C(O)R^{10}$, halo, nitro, cyano, 4–10 membered heterocyclic, —$R_{01}$, —$NR^{10}R^{11}$, —$NHC(O)R^{10}$, —$NHC(O)NR^{10}R^{11}$, $C_6$–$C_{10}$ aryl, 4–10 membered heterocyclic, —$S(O)n R10$ and —$SO_2NR^{10}R^{11}$, wherein n is an integer ranging from 0 to 2;

each $R^{10}$ and $R^{11}$ is independently H or $C_1$–$C_{10}$ alkyl; and, $R^{12}$ is a 4–10 membered heterocycyl or $C_6$–$C_{10}$ aryl, wherein said heterocycyl and aryl groups are optionally substituted by 1 to 3 substituents independently selected from the group consisting of —$C(O)OR^{10}$, —$OR^{10}$, —$C(O)R^{10}$, halo, nitro, cyano, 4–10 membered heterocyclic, —$R^{10}$, —$NR^{10}R^{11}$, —$NHC(O)R^{10}$, —NHC(O)NR$^{10}$R$^{11}$, C$_6$–C$_{10}$ aryl, 4–10 membered heterocyclic, —S(O)$_n$R$^{10}$, and —SO$_2$NR$^{10}$R$^{11}$, wherein n is an integer ranging from 0 to 2.

2. A compound of the formula 2

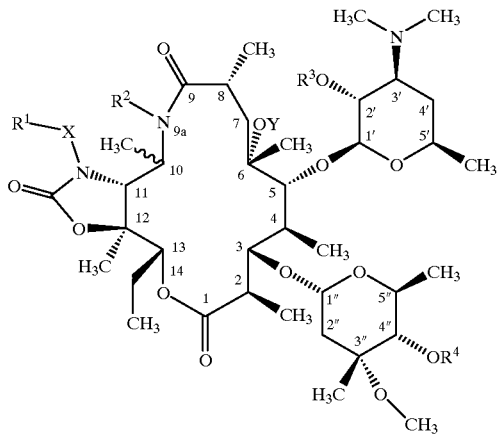

and pharmaceutically acceptable salts thereof, wherein:

X is —O—, —NR$^5$—, or (CR$^5$R$^6$)$_g$, wherein g is 0 or 1 and wherein, when X is —NR$^5$—, R$^5$ and R$^2$ are taken together to form —(CR$^7$R$^8$)—;

or X is taken together with R$^1$ to form —N=CR$^7$R$^8$;

or X and R$_1$ are taken together to form a heterocyclic ring of the formula XI

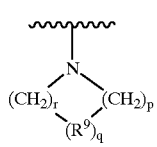

XI wherein in said ring of formula XI, r and p are each independently an integer ranging from 1 to 3, q is 0 or 1, and R$^9$ is —CH$_2$—, O, S, —C(O)—, —C(S)—, —SO$_2$—, —CH=CH—, —CH(OH)CH(OH)—, or —NH—; and wherein the (CH$_2$)$_r$ and (CH$_2$)$_p$ portions of said ring of formula XI are optionally substituted by 1 to 4 substituents and wherein each hydrogen atom of R$^9$ when R$^9$ is —CH$_2$—, —CH=CH—, —CH(OH)CH(OH)—, or —NH is optionally substituted by one substituent, said optional substituents being independently selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, C$_6$–C$_{10}$ aryl, 4–10 membered heterocyclic, —S(O)$_n$R$^{10}$, and —SO$_2$NR$^{10}$ R$^{11}$, wherein n is an integer ranging from 0 to 2;

R$^1$ is H, R$^7$, —C(O)R$^7$, —C(O)R$^{12}$, —C(O)OR$^7$, —C(O)OR$^{12}$, or —(CR$^5$R$^6$)$_m$R$^{12}$, wherein m is an interger ranging from 0 to 6;

R$^2$ is H or C$_1$–C$_{12}$ alkyl, wherein one or two carbons of said alkyl are optionally replaced by a heterotom selected from the group consisting of O, S and N, and are optionally substituted by 1 to 3 substituents selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, C$_6$–C$_{10}$ aryl, 4–10 membered heterocyclic, —S(O)$_n$R$^{10}$, and —SO$_2$NR$^{10}$R$^{11}$, wherein n is an integer ranging from 0 to 2;

each R$^3$ and R$^4$ is independently selected from the group consisting of H, —C(O)R$^{12}$ or C$_1$–C$_{18}$ alkanoyl, wherein in the alkyl portion of said alkanoyl one or two carbons optionally may be replaced by a heteroatom selected from the group consisting of O, S and N;

each R$^5$ and R$^6$ is independently H, halo, or C$_1$–C$_{10}$ alkyl and R$^5$ and R$^6$ may each independently vary when m is greater than 1;

each R$^7$ and R$^8$ is independently selected from the group consisting of H and C$_1$–C$_{18}$ alkyl, wherein one or two carbons of said alkyl are optionally replaced by a heteroatom selected from the group consisting of O, S and N, and are optionally substituted by 1 to 3 substituents selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, C$_6$–C$_{10}$ aryl, 4–10 membered heterocyclic, —S(O)nR10 and —SO$_2$NR$^{10}$R$^{11}$, wherein n is an integer ranging from 0 to 2;

each R$^{10}$, and R$^{11}$ is independently H or C$_1$–C$_{10}$ alkyl;

R$^{12}$ is a 4–10 membered heterocycyl or C$_6$–C$_{10}$ aryl, wherein said heterocycyl and aryl groups are optionally substituted by 1 to 3 substituents independently selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, C$_6$–C$_{10}$ aryl, 4–10 membered heterocyclic, —S(O)$_n$R$^{10}$, and —SO$_2$NR$^{10}$R$^{11}$, wherein n is an integer ranging from 0 to 2; and Y is R$^7$ or —(CR$^5$R$^6$)$_m$R$^{12}$, wherein m is an interger ranging from 0 to 6; and R$^5$ and R$^6$ may each independently vary when m is greater than 1.

3. A compound of the formula 3

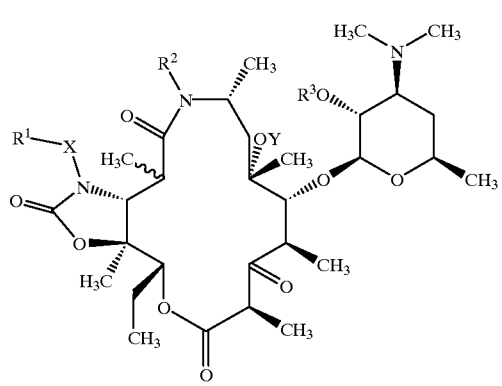

and pharmaceutically acceptable salts thereof, wherein:

X is —O—, —NR$^5$—, or (CR$^5$R$^6$)$_g$, wherein g is 0 or 1;

or X is taken together with R$^1$ to form —N=CR$^7$R$^8$;

or X and R$^1$ are taken together to form a heterocyclic ring of the formula XI

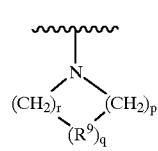

XI wherein in said ring of formula XI, r and p are each independently an integer ranging from 1 to 3, q is 0 or 1, and $R^9$ is —$CH_2$—, O, S, —C(O)—, —C(S)—, —$SO_2$—, —CH=CH—, —CH(OH)CH(OH)—, or —NH—; and wherein the $(CH_2)_r$ and $(CH_2)_p$ portions of said ring of formula XI are optionally substituted by 1 to 4 substituents and wherein each hydrogen atom of $R^9$ when $R^9$ is —$CH_2$—, —CH=CH—, —CH(OH)CH(OH)—, or —NH is optionally substituted by one substituent, said optional substituents being independently selected from the group consisting of —C(O)$OR^{10}$, —$OR^{10}$, —C(O)$R^{10}$, halo, nitro, cyano, 4–10 membered heterocyclic, —$R^{10}$, —$NR^{10}R^{11}$, —NHC(O)$R^{10}$, —NHC(O)$NR^{10}R^{11}$, $C_6$–$C_{10}$ aryl, 4–10 membered heterocyclic, —S(O)$_nR^{10}$, and —$SO_2NR^{10}R^{11}$, wherein n is an integer ranging from 0 to 2;

$R^1$ is H, $R^7$, —C(O)$R^7$, —C(O)$R^{12}$, —C(O)$OR^7$, —C(O)$OR^{12}$, or —$(CR^5R^6)_mR^{12}$, wherein m is an interger ranging from 0 to 6;

$R^2$ is H or $C_1$–$C_{12}$ alkyl, wherein one or two carbons of said alkyl are optionally replaced by a heteroatom selected from the group consisting of O, S and N, and are optionally substituted by 1 to 3 substituents selected from the group consisting of —C(O)$OR^{10}$, —$OR^{10}$, —C(O)$R^{10}$, halo, nitro, cyano, 4–10 membered heterocyclic, —$R^{10}$, —$NR^{10}R^{11}$, —NHC(O)$R^{10}$, —NHC(O)$NR^{10}R^{11}$, $C_6$–$C_{10}$ aryl, 4–10 membered heterocyclic, —S(O)$_nR^{10}$, and —$SO_2NR^{10}R^{11}$, wherein n is an integer ranging from 0 to 2;

each $R^3$ is independently selected from the group consisting of H, —C(O)$R^{12}$ or $C_1$–$C_{18}$ alkanoyl, wherein in the alkyl portion of said alkanoyl one or two carbons optionally may be replaced by a heteroatom selected from O, S and N;

each $R^5$ and $R^6$ is independently H, halo, or $C_1$–$C_{10}$ alkyl and $R^5$ and $R^6$ may each independently vary when m is greater than 1;

each $R^7$ and $R^8$ is independently selected from the group consisting of H and $C_1$–$C_{18}$ alkyl, wherein one or two carbons of said alkyl are optionally replaced by a heteroatom selected from the group consisting of O, S and N, and are optionally substituted by 1 to 3 substituents selected from the group consisting of —C(O)$OR^{10}$, —$OR^{10}$, —C(O)$R^{10}$, halo, nitro, cyano, 4–10 membered heterocyclic, —$R^{10}$, —$NR^{10}R^{11}$, —NHC(O)$R^{10}$, —NHC(O)$NR^{10}R^{11}$, $C_6$–$C_{10}$ aryl, 4–10 membered heterocyclic, —S(O)n$R^{10}$ and —$SO_2NR^{10}R^{11}$, wherein n is an integer ranging from 0 to 2;

each $R^{10}$, and $R^{11}$ is independently H or $C_1$–$C_{10}$ alkyl;

$R^{12}$ is a 4–10 membered heterocycyl or $C_6$–$C_{10}$ aryl, wherein said heterocycyl and aryl groups are optionally substituted by 1 to 3 substituents independently selected from the group consisting of —C(O)$OR^{10}$, —$OR^{10}$, —C(O)$R^{10}$, halo, nitro, cyano, 4–10 membered heterocyclic, —$R^{10}$, —$NR^{10}R^{11}$, —NHC(O)$R^{10}$, —NHC(O)$NR^{10}R^{11}$, $C_6$–$C_{10}$ aryl, 4–10 membered heterocyclic, —S(O)$_nR^{10}$, and —$SO_2NR^{10}R^{11}$, wherein n is an integer ranging from 0 to 2; and Y is $R^7$ or —$(CR^5R^6)_mR^{12}$, wherein m is an interger ranging from 0 to 6; and $R^5$ and $R^6$ may each independently vary when m is greater than 1.

4. A compound of the formula 4

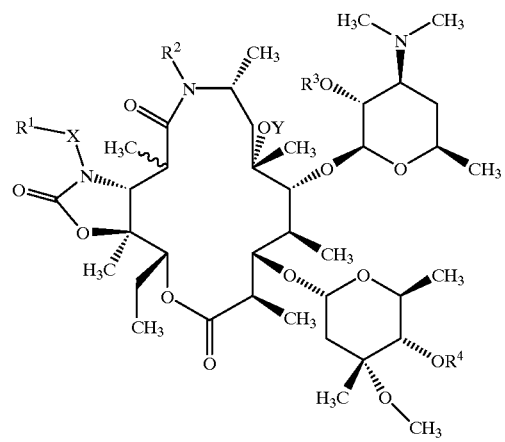

and pharmaceutically acceptable salts thereof, wherein:
X is —O—, —$NR^5$—, or $(CR^5R^6)_g$, wherein g is 0 or 1; or X is taken together with $R^1$ to form —N=$CR^7R^8$; or X and $R^1$ are taken together to form a heterocyclic ring of the formula XI

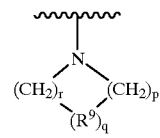

XI wherein in said ring of formula XI, r and p are each independently an integer ranging from 1 to 3, q is 0 or 1, and $R^9$ is —$CH_2$—, O, S, —C(O)—, —C(S)—, —$SO_2$—, —CH=CH—, —CH(OH)CH(OH)—, or —NH—; and wherein the $(CH_2)_r$ and $(CH_2)_p$ portions of said ring of formula XI are optionally substituted by 1 to 4 substituents and wherein each hydrogen atom of $R^9$ when $R^9$ is —$CH_2$—, —CH=CH—, —CH(OH)CH(OH)—, or —NH is optionally substituted by one substituent, said optional substituents being independently selected from the group consisting of —C(O)$OR^{10}$, —$OR^{10}$, —C(O)$R^{10}$, halo, nitro, cyano, 4–10 membered heterocyclic, —$R^{10}$, —$NR^{10}R^{11}$, —NHC(O)$R^{10}$, —NHC(O)$NR^{10}R^{11}$, $C_6$–$C_{10}$ aryl, 4–10 membered heterocyclic, —S(O)$_nR^{10}$, and —$SO_2NR^{10}R^{11}$, wherein n is an integer ranging from 0 to 2;

$R^1$ is H, $R^7$, —C(O)$R^7$, —C(O)$R^{12}$, —C(O)$OR^7$, —C(O)$OR^{12}$, or —$(CR^5R^6)_mR^{12}$, wherein m is an interger ranging from 0 to 6;

$R^2$ is H or $C_1$–$C_{12}$ alkyl, wherein one or two carbons of said alkyl are optionally replaced by a heteroatom selected from the group consisting of O, S and N, and are optionally substituted by 1 to 3 substituents selected from the group consisting of —C(O)$OR^{10}$, —$OR^{10}$, —C(O)$R^{10}$, halo, nitro, cyano, 4–10 membered heterocyclic, —$R^{10}$, —$NR^{10}R^{11}$, —NHC(O)$R^{10}$, —NHC(O)$NR^{10}R^{11}$, $C_6$–$C_{10}$ aryl, 4–10 membered heterocyclic, —S(O)$_nR^{10}$, and —$SO_2NR^{10}R^{11}$, wherein n is an integer ranging from 0 to 2;

each $R^3$ and $R^4$ is independently selected from the group consisting of H, —C(O)$R^{12}$ or $C_1$–$C_{18}$ alkanoyl, wherein in the alkyl portion of said alkanoyl one or two carbons optionally may be replaced by a heteroatom selected from O, S and N;

each $R^5$ and $R^6$ is independently H, halo, or $C_1$–$C_{10}$ alkyl and $R^5$ and $R^6$ may each independently vary when m is greater than 1;

each $R^7$ and $R^8$ is independently selected from the group consisting of H and $C_1$–$C_{18}$ alkyl, wherein one or two carbons of said alkyl are optionally replaced by a heteroatom selected from the group consisting of O, S and N, and are optionally substituted by 1 to 3 substituents selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, $C_6$–$C_{10}$ aryl, 4–10 membered heterocyclic, —S(O)nR10 and —SO$_2$NR$^{10}$R$^{11}$, wherein n is an integer ranging from 0 to 2;

each $R^{10}$, and $R^{11}$ is independently H or $C_1$–$C_{10}$ alkyl;

$R^{12}$ is a 4–10 membered heterocycyl or $C_6$–$C_{10}$ aryl, wherein said heterocycyl and aryl groups are optionally substituted by 1 to 3 substituents independently selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, $C_6$–$C_{10}$ aryl, 4–10 membered heterocyclic, —S(O)$_n$R$^{10}$, and —SO$_2$NR$^{10}$R$^{11}$, wherein n is an integer ranging from 0 to 2; and Y is $R^7$ or —(CR$^5$R$^6$)$_m$R$^{12}$, wherein m is an interger ranging from 0 to 6; and $R^5$ and $R^6$ may each independently vary when m is greater than 1.

5. A compound of the formula 5

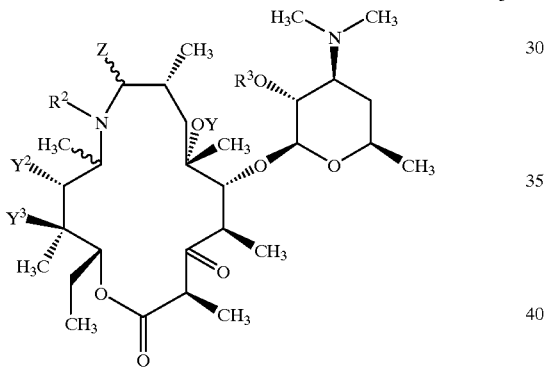

or a pharmaceutically acceptable salt thereof, wherein:

X is —O—, —NR$^5$—, or (CR$^5$R$^6$)$_g$, wherein g is 0 or 1 and wherein, when X is —NR$^5$—, $R^5$ and $R^2$ are taken together to form —(CR$^7$R$^8$)—;

or X is taken together with $R^1$ to form —N=CR$^7$R$^8$;

or X and $R^1$ are taken together to form a heterocyclic ring of the formula XI

XI

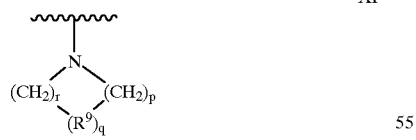

wherein in said ring of formula XI, r and p are each independently an integer ranging from 1 to 3, q is 0 or 1, and $R^9$ is —CH$_2$—, O, S, —C(O)—, —C(S)—, —SO$_2$, —CH=CH—, —CH(OH)CH(OH)—, or —NH—; and wherein the (CH$_2$)$_r$ and (CH$_2$)$_p$ portions of said ring of formula XI are optionally substituted by 1 to 4 substituents and wherein each hydrogen atom of $R^9$ when $R^9$ is —CH$_2$—, —CH=CH—, —CH(OH)CH(OH)—, or —NH is optionally substituted by one substituent, said optional substituents being independently selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, $C_6$–$C_{10}$ aryl, 4–10 membered heterocyclic, —S(O)$_n$R$^{10}$, and —SO$_2$NR$^{10}$R$^{11}$, wherein n is an integer ranging from 0 to 2;

$R^1$ is H, $R^7$,—C(O)R$^7$, —C(O)R$^{12}$, —C(O)OR$^7$, —C(O)OR$^{12}$, or —(CR$^5$R$^6$)$_m$R$^{12}$, wherein m is an interger ranging from 0 to 6;

$R^2$ is H or $C_1$–$C_{16}$ alkyl, wherein one or two carbons of said alkyl are optionally replaced by a heteroatom selected from the group consisting of O, S and N(R$^5$), and are optionally substituted by 1 to 3 substituents selected from the group consisting of the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, $C_6$–$C_{10}$ aryl, 4–10 membered heterocyclic, —S(O)$_n$R$^{10}$, and —SO$_2$NR$^{10}$R$^{11}$, wherein n is an integer ranging from 0 to 2;

each $R^3$ is independently selected from the group consisting of H, —C(O)R$^{12}$ or $C_1$–$C_{18}$ alkanoyl, wherein in the alkyl portion of said alkanoyl one or two carbons optionally may be replaced by a heteroatom selected from the group consisting of O, S and N;

each $R^5$ and $R^6$ is independently H, halo, or $C_1$–$C_{10}$ alkyl and $R^5$ and $R^6$ may each independently vary when m is greater than 1;

each $R^7$ and $R^8$ is independently selected from the group consisting of H and $C_1$–$C_{18}$ alkyl, wherein one or two carbons of said alkyl are optionally replaced by a heteroatom selected from the group consisting of O, S and N, and are optionally substituted by 1 to 3 substituents selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, $C_6$–$C_{10}$ aryl, 4–10 membered heterocyclic, —S(O)nR10 and —SO$_2$NR$^{10}$R$^{11}$, wherein n is an integer ranging from 0 to 2;

each $R^{10}$, $R^{11}$ and Z is independently H or $C_1$–$C_{10}$ alkyl; wherein one or two carbons of said alkyl are optionally replaced by a heteroatom selected from the group consisting of O, S and N, and are optionally substituted by 1 to 3 substituents selected from the group consisting of —C(O)OR$^{13}$, —OR$^{13}$, —C(O)R$^{13}$, halo, nitro, cyano, 4–10 membered heterocyclic, —R$^{13}$, —NR$^{13}$R$^{14}$, —NHC(O)R$^{13}$, —NHC(O)NR$^{13}$R$^{14}$, $C_6$–$C_{10}$ aryl, 4–10 membered heterocyclic, —S(O)$_n$R$^{13}$ wherein n is an integer ranging from 0 to 2, and —SO$_2$NR$^{13}$R$^{14}$;

$R^{12}$ is a 4–10 membered heterocycyl or $C_6$–$C_{10}$ aryl, wherein said heterocycyl and aryl groups are optionally substituted by 1 to 3 substituents independently selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, $C_6$–$C_{10}$ aryl, 4–10 membered heterocyclic, —S(O)$_n$R$^{10}$, and —SO$_2$NR$^{10}$R$^{11}$, wherein n is an integer ranging from 0 to 2;

each $R^{13}$ and $R^{14}$ is independently H or $C_1$–$C_6$ alkyl optionally substituted by 1 to 3 halo groups;

Y is $R^7$ or —(CR$^5$R$^6$)$_m$R$^{12}$, wherein m is an integer ranging from 0 to 6; and $R^5$ and $R^6$ may each independently vary when m is greater than 1;

$Y^2$ is $C_1$–$C_{16}$ alkoxy, —C(O)NH($C_1$–$C_{16}$ alkyl), or —OC(O)NH($C_1$–$C_{16}$ alkyl), wherein the alkyl moieties of the foregoing $Y^2$ groups are optionally substituted by an $R^{12}$ group or 1 to 3 halo groups;

$Y^3$ is hydroxy;

or $Y^2$ and $Y^3$ are taken together to form:

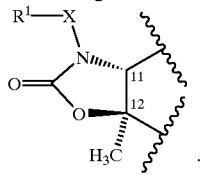

6. A compound of the formula 6

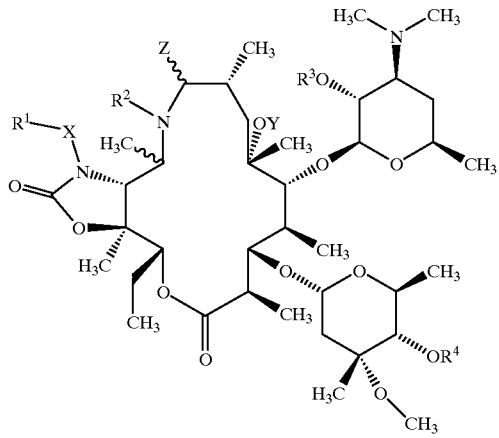

or a pharmaceutically acceptable salt thereof, wherein:
X is —O—, —$NR^5$—, or $(CR^5R^6)_g$, wherein g is 0 or 1 and wherein, when X is —$NR^5$—, $R^5$ and $R^2$ are taken together to form —$(CR^7R^8)$—;
or X is taken together with $R^1$ to form —N=$CR^7R^8$;
or X and $R^1$ are taken together to form a heterocyclic ring of the formula XI

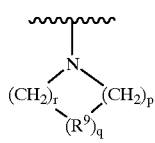

XI wherein in said ring of formula XI, r and p are each independently an integer ranging from 1 to 3, q is 0 or 1, and $R^9$ is —$CH_2$—, O, S, —C(O)—, —C(S)—, —$SO_2$—, —CH=CH—, —CH(OH)CH(OH)—, or —NH—; and wherein the $(CH_2)_r$ and $(CH_2)_p$ portions of said ring of formula XI are optionally substituted by 1 to 4 substituents and wherein each hydrogen atom of $R^9$ when $R^9$ is —$CH_2$—, —CH=CH—, —CH(OH)CH(OH)—, or —NH is optionally substituted by one substituent, said optional substituents being independently selected from the group consisting of —C(O)$OR^{10}$, —$OR^{10}$, —C(O)$R^{10}$, halo, nitro, cyano, 4–10 membered heterocyclic, —$R^{10}$, —$NR^{10}R^{11}$, —NHC(O)$R^{10}$, —NHC(O)$NR^{10}R^{11}$, $C_6$–$C_{10}$ aryl, 4–10 membered heterocyclic, —S(O)$_n$$R^{10}$, and —$SO_2NR^{10}R^{11}$, wherein n is an integer ranging from 0 to 2;

$R^1$ is H, $R^7$, —C(O)$R^7$, —C(O)$R^{12}$, —C(O)$OR^7$, C(O)$OR^{12}$, or —$(CR^5R^6)_mR^{12}$, wherein m is an interger ranging from 0 to 6;

$R^2$ is H or $C_1$–$C_{16}$ alkyl, wherein one or two carbons of said alkyl are optionally replaced by a heteroatom selected from the group consisting of O, S and N($R^5$), and are optionally substituted by 1 to 3 substituents selected from the group consisting of —C(O)$OR^{10}$, —$OR^{10}$, —C(O)$R^{10}$, halo, nitro, cyano, 4–10 membered heterocyclic, —$R^{10}$, —$NR^{10}R^{11}$, —NHC(O)$R^{10}$, —NHC(O)$NR^{10}R^{11}$, $C_6$–$C_{10}$ aryl, 4–10 membered heterocyclic, —S(O)$_n$$R^{10}$, and —$SO_2NR^{10}R^{11}$, wherein n is an integer ranging from 0 to 2;

each $R^3$ and $R^4$ is independently selected from the group consisting of H, —C(O)$R^{12}$ or $C_1$–$C_{18}$ alkanoyl, wherein in the alkyl portion of said alkanoyl one or two carbons optionally may be replaced by a heteroatom selected from the group consisting of O, S and N;

each $R^5$ and $R^6$ is independently H, halo, or $C_1$–$C_{10}$ alkyl and $R^5$ and $R^6$ may each independently vary when m is greater than 1;

each $R^7$ and $R^8$ is independently selected from the group consisting of H and $C_1$–$C_{18}$ alkyl, wherein one or two carbons of said alkyl are optionally replaced by a heteroatom selected from the group consisting of O, S and N, and are optionally substituted by 1 to 3 substituents selected from the group consisting of —C(O)$OR^{10}$, —$OR^{10}$, —C(O)$R^{10}$, halo, nitro, cyano, 4–10 membered heterocyclic, —$R^{10}$, —$NR^{10}R^{11}$, —NHC(O)$R^{10}$, —NHC(O)$NR^{10}R^{11}$, $C_6$–$C_{10}$ aryl, 4–10 membered heterocyclic, —S(O)nR10 and —$SO_2NR^{10}R^{11}$, wherein n is an integer ranging from 0 to 2;

each $R^{10}$, $R^{11}$ and Z is independently H or $C_1$–$C_{10}$ alkyl; wherein one or two carbons of said alkyl are optionally replaced by a heteroatom selected from the group consisting of O, S and N, and are optionally substituted by 1 to 3 substituents selected from the group consisting of —C(O)$OR^{13}$, —OR—, —C(O)$R^{13}$, halo, nitro, cyano, 4–10 membered heterocyclic, —$R^{13}$, —$NR^{13}R^{14}$, —NHC(O)$R^{13}$, —NHC(O)$NR^{13}R^{14}$, $C_6$–$C_{10}$ aryl, 4–10 membered heterocyclic, —S(O)$_n$$R^{13}$ wherein n is an integer ranging from 0 to 2, and —$SO_2NR^{13}R^{14}$;

$R^{12}$ is a 4–10 membered heterocycyl or $C_6$–$C_{10}$ aryl, wherein said heterocycyl and aryl groups are optionally substituted by 1 to 3 subsfituents independently selected from the group consisting of —C(O)$OR^{10}$, —$OR^{10}$, —C(O)$R^{10}$, halo, nitro, cyano, 4–10 membered heterocyclic, —$R^{10}$, —$NR^{10}R^{11}$, —NHC(O)$R^{10}$, —NHC(O)$NR^{10}R^{11}$, $C_6$–$C_{10}$ aryl, 4–10 membered heterocyclic, —S(O)$_n$$R^{10}$, and —$SO_2NR^{10}R^{11}$, wherein n is an integer ranging from 0 to 2;

each $R^{13}$ and $R^{14}$ is independently H or $C_1$–$C_6$ alkyl optionally substituted by 1 to 3 halo groups;

Y is $R^7$ or —$(CR^5R^6)_mR^{12}$, wherein m is an interger ranging from 0 to 6; and $R^5$ and $R^6$ may each independently vary when m is greater than 1.

7. A compound of the formula 7

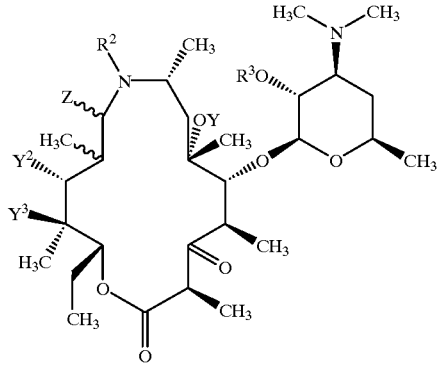

or a pharmaceutically acceptable salt thereof, wherein:
X is —O—, —$NR^5$—, or $(CR^5R^6)_g$, wherein g is 0 or 1;
or X is taken together with $R^1$ to form —N=$CR^7R^8$;

or X and R¹ are taken together to form a heterocyclic ring of the formula XI

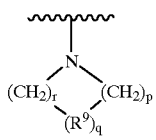

wherein in said ring of formula XI, r and p are each independently an integer ranging from 1 to 3, q is 0 or 1, and $R^9$ is —CH$_2$—, O, S, —C(O)—, —C(S)—, —SO$_2$—, —CH=CH—, —CH(OH)CH(OH)—, or —NH—; and wherein the (CH$_2$)$_r$ and (CH$_2$)$_p$ portions of said ring of formula XI are optionally substituted by 1 to 4 substituents and wherein each hydrogen atom of $R^9$ when $R^9$ is —CH$_2$—, —CH=CH—, —CH(OH)CH(OH)—, or —NH is optionally substituted by one substituent, said optional substituents being independently selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, C$_6$–C$_{10}$ aryl, 4–10 membered heterocyclic, —S(O)$_n$R$^{10}$, and —SO$_2$NR$^{10}$R$^{11}$, wherein n is an integer ranging from 0 to 2;

$R^1$ is H, $R^7$, —C(O)R$^7$, —C(O)R$^{12}$, —C(O)OR$^7$, —C(O)OR$^{12}$, or —(CR$^5$R$^6$)$_m$R$^{12}$, wherein m is an interger ranging from 0 to 6;

$R^2$ is H or C$_1$–C$_{16}$ alkyl, wherein one or two carbons of said alkyl are optionally replaced by a heteroatom selected from the group consisting of O, S and N, and are optionally substituted by 1 to 3 substituents selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, C$_6$–C$_{10}$ aryl, 4–10 membered heterocyclic, —S(O)$_n$R$^{10}$, and —SO$_2$NR$^{10}$R$^{11}$, wherein n is an integer ranging from 0 to 2;

each $R^3$ is independently selected from the group consisting of H, —C(O)R$^{12}$ or C$_1$–C$_{18}$ alkanoyl, wherein in the alkyl portion of said alkanoyl one or two carbons optionally may be replaced by a heteroatom selected from the group consisting of O, S and N;

each $R^5$ and $R^6$ is independently H, halo, or C$_1$–C$_{10}$ alkyl and $R^5$ and $R^6$ may each independently vary when m is greater than 1;

each $R^7$ and $R^8$ is independently selected from the group consisting of H and C$_1$–C$_{18}$ alkyl, wherein one or two carbons of said alkyl are optionally replaced by a heteroatom selected from the group consisting of O, S and N, and are optionally substituted by 1 to 3 substituents selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, C$_6$–C$_{10}$ aryl, 4–10 membered heterocyclic, —S(O)nR10 and —SO$_2$NR$^{10}$R$^{11}$, wherein n is an integer ranging from 0 to 2;

each R$^{10}$, R$^{11}$ and Z is independently H or C$_1$–C$_{10}$ alkyl; wherein one or two carbons of said alkyl are optionally replaced by a heteroatom selected from the group consisting of O, S and N, and are optionally substituted by 1 to 3 substituents selected from the group consisting of —C(O)OR$^{13}$, —OR$^{13}$, —C(O)R$^{13}$, halo, nitro, cyano, 4–10 membered heterocyclic, —R$^{13}$, —NR$^{13}$R$^{14}$, —NHC(O)R$^{13}$, —NHC(O)NR$^{13}$R$^{14}$, C$_6$–C$_{10}$ aryl, 4–10 membered heterocyclic, —S(O)$_n$R$^{13}$ wherein n is an integer ranging from 0 to 2, and —SO$_2$NR$^{13}$R$^{14}$;

R$^{12}$ is a 4–10 membered heterocycyl or C$_6$–C$_{10}$ aryl, wherein said heterocycyl and aryl groups are optionally substituted by 1 to 3 substituents independently selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, C$_6$–C$_{10}$ aryl, 4–10 membered heterocyclic, —S(O)$_n$R$^{10}$, and —SO$_2$NR$^{10}$R$^{11}$, wherein n is an integer ranging from 0 to 2;

each R$^{13}$ and R$^{14}$ is independently H or C$_1$–C$_6$ alkyl optionally substituted by 1 to 3 halo groups;

Y is $R^7$ or —(CR$^5$R$^6$)$_m$R$^{12}$, wherein m is an interger ranging from 0 to 6; and $R^5$ and $R^6$ may each independently vary when m is greater than 1;

$Y^2$ is C$_1$–C$_{16}$ alkoxy, —C(O)NH(C$_1$–C$_{16}$ alkyl), or —OC(O)NH(C$_1$–C$_{16}$ alkyl), wherein the alkyl moieties of the foregoing $Y^2$ groups are optionally substituted by an R$^{12}$ group or 1 to 3 halo groups;

$Y^3$ is hydroxy;

or $Y^2$ and $Y^3$ are taken together to form:

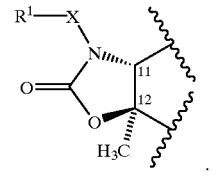

8. A compound of the formula 8

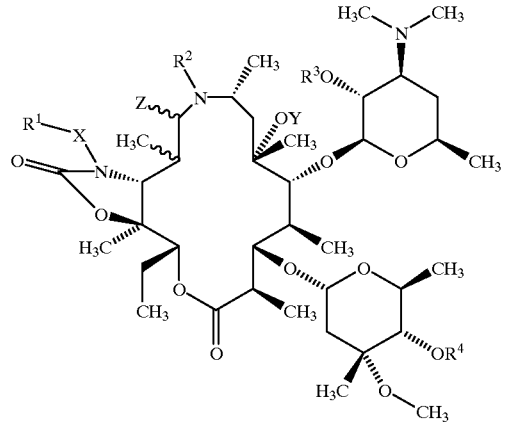

or pharmaceutically acceptable salt thereof, wherein:

X is —O—, —NR$^5$—, or (CR$^5$R$^6$)$_g$, wherein g is 0 or 1; or X is taken together with R$^1$ to form —N=CR$^7$R$^8$; or X and R$^1$ are taken together to form a heterocyclic ring of the formula XI

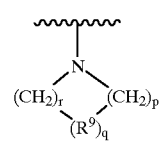

wherein in said ring of formula XI, r and p are each independently an integer ranging from 1 to 3, q is 0 or 1, and $R^9$ is CH$_2$—, O, S, —C(O)—, —C(S)—, —SO$_2$—, —CH=CH—, —CH(OH)CH(OH)—, or —NH—; and wherein the $(CH_2)_r$ and $(CH_2)_p$ portions of said ring of formula XI are optionally substituted by 1 to 4 substituents and wherein each hydrogen atom of $R^9$ when $R^9$ is —CH$_2$—, —CH=CH—, —CH(OH)CH(OH)—, or —NH is optionally substituted by one substituent, said optional substituents being independently selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)NR$^{10}$, —NHC(O)NR$^{10}$R$^{11}$, $C_6$–$C_{10}$ aryl, 4–10 membered heterocyclic, —S(O)$_n$R$^{10}$, and —SO$_2$NR$^{10}$R$^{11}$, wherein n is an integer ranging from 0 to 2;

- $R^1$ is H, $R^7$, —C(O)R$^7$, —C(O)R$^{12}$, —C(O)OR$^7$, —C(O)OR$^{12}$, or —(CR$^5$R$^6$)$_m$R$^{12}$, wherein m is an interger ranging from 0 to 6;
- $R^2$ is H or $C_1$–$C_{12}$ alkyl, wherein one or two carbons of said alkyl are optionally replaced by a heteroatom selected from the group consisting of O, S and N, and are optionally substituted by 1 to 3 substituents selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, $C_6$–$C_{10}$ aryl, 4–10 membered heterocyclic, —S(O)$_n$R$^{10}$, and —SO$_2$NR$^{10}$R$^{11}$, wherein n is an integer ranging from 0 to 2;
- each $R^3$ and $R^4$ is independently selected from the group consisting of H, —C(O)R$^{12}$ or $C_1$–$C_{18}$ alkanoyl, wherein in the alkyl portion of said alkanoyl one or two carbons optionally may be replaced by a heteroatom selected from O, S and N;
- each $R^5$ and $R^6$ is independently H, halo, or $C_1$–$C_{10}$ alkyl and $R^5$ and $R^6$ may each independently vary when m is greater than 1;
- each $R^7$ and $R^8$ is independently selected from the group consisting of H and $C_1$–$C_{18}$ alkyl, wherein one or two carbons of said alkyl are optionally replaced by a heteroatom selected from the group consisting of O, S and N, and are optionally substituted by 1 to 3 substituents selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, $C_6$–$C_{10}$ aryl, 4–10 membered heterocyclic, —S(O)nR10 and —SO$_2$NR$^{10}$R$^{11}$, wherein n is an integer ranging from 0 to 2;
- each $R^{10}$, $R^{11}$ and Z is independently H or $C_1$–$C_{10}$ alkyl; wherein one or two carbons of said alkyl are optionally replaced by a heteroatom selected from the group consisting of O, S and N, and are optionally substituted by 1 to 3 substituents selected from the group consisting of —C(O)OR$^{13}$, —OR$^{13}$, —C(O)R$^{13}$, halo, nitro, cyano, 4–10 membered heterocyclic, —R$^{13}$, —NR$^{13}$R$^{14}$, —NHC(O)R$^{13}$, —NHC(O)NR$^{13}$R$^{14}$, $C_6$–$C_{10}$ aryl, 4–10 membered heterocyclic, —S(O)$_n$R$^{13}$ wherein n is an integer ranging from 0 to 2, and SO$_2$NR$^{13}$R$^{14}$;
- $R^{12}$ is a 4–10 membered heterocycyl or $C_6$–$C_{10}$ aryl, wherein said heterocycyl and aryl groups are optionally substituted by 1 to 3 substituents independently selected from the group consisting of —C(O)OR$^{10}$, —OR$^{10}$, —C(O)R$^{10}$, halo, nitro, cyano, 4–10 membered heterocyclic, —R$^{10}$, —NR$^{10}$R$^{11}$, —NHC(O)R$^{10}$, —NHC(O)NR$^{10}$R$^{11}$, $C_6$–$C_{10}$ aryl, 4–10 membered heterocyclic, —S(O)$_n$R$^{10}$, and —SO$_2$NR$^{10}$R$^{11}$, wherein n is an integer ranging from 0 to 2;
- each $R^{13}$ and $R^{14}$ is independently H or $C_1$–$C_6$ alkyl optionally substituted by 1 to 3 halo groups;
- Y is $R^7$ or —(CR$^5$R$^6$)$_m$R$^{12}$, wherein m is an interger ranging from 0 to 6; and $R^5$ and $R^6$ may each independently vary when m is greater than 1.

9. The compound of claim 1 wherein:

$R^2$ is H, $R^3$ is H, X is NH, Y is Me and $R^1$ is 3-(imidazo (4,5-b)pyridin-3-yl)-propyl;

$R^2$ is H, $R^3$ is H, X is NH, Y is Me and $R^1$ is 3-(4-pyridin-3-yl-imidazol-1-yl)-propyl;

$R^2$ is H, $R^3$ is H, X is NH, Y is Me and $R^1$ is 3-quinolin-4-yl-propyl;

$R^2$ is H, $R^3$ is H, X is NH, Y is Me and $R^1$ is 3-(7-methoxy-quinolin-4-yl)-propyl;

$R^2$ is H, $R^3$ is H, X is NH, Y is Me and $R^1$ is 3-benzoimidazol-1-yl-propyl;

$R^2$ is H, $R^3$ is H, X is NH, Y is Me and $R^1$ is 3-indol-1-yl-propyl;

$R^2$ is H, $R^3$ is H, X is NH, Y is Me and $R^1$ is 3-indazol-1-yl-propyl;

$R^2$ is H, $R^3$ is H, X is NH, Y is Me and $R^1$ is 3-carbazol-1-yl-propyl;

$R^2$ is H, $R^3$ is H, X is NH, Y is Me and $R^1$ is 3(5-phenyl-1H-pyrrol-2-yl)-propyl;

$R^2$ is H, $R^3$ is H, X is NH, Y is Me and $R^1$ is 3-(4-phenyl-imidazol-1-yl)-propyl);

$R^2$ is H, $R^3$ is H, X is NH, Y is Me and $R^1$ is 3-(3-(4-chlorophenyl)-(1,2,4)oxadizol-5-yl)-propyl;

$R^2$ is H, $R^3$ is H, X is NH, Y is Me and $R^1$ is 3-(3-(4-methoxyphenyl)1,2,4)oxadizol-5-yl)-propyl;

$R^2$ is H, $R^3$ is H, X is NH, Y is Me and $R^1$ is 3-(3-(4-pyridin-4-yl)-(1,2,4)oxadizol-5-yl)-propyl;

$R^2$ is H, $R^3$ is H, X is NH, Y is Me and $R^1$ is 3-benzotrizol-1-yl-propyl;

$R^2$ is H, $R^3$ is H, X is NH, Y is Me and $R^1$ is 3-pyridin-4-yl-propyl;

$R^2$ is H, $R^3$ is H, X is NH, Y is Me and $R^1$ is 3-(2-pyridin-3-yl-thiazol-4-yl)-propyl;

$R^2$ is H, $R^3$ is H, X is NH, Y is Me and $R^1$ is 3-(2-phenyl-thiazol-5-yl)-propyl;

$R^2$ is H, $R^3$ is H, X is NH, Y is Me and $R^1$ is 3-(4-phenyl-1H-imidazol-2-yl)-propyl.

10. The compound of claim 2 wherein:

$R^2$ is H, $R^3$ is H, $R^4$ is H, X is NH, Y is Me and $R^1$ is 3-(imidazo(4,5-b)pyridin-3-yl)-propyl;

$R^2$ is H, $R^3$ is H, $R^4$ is H, X is NH, Y is Me and $R^1$ is 3-(4-pyridin-3-yl-imidazol-1-yl)-propyl;

$R^2$ is H, $R^3$ is H, $R^4$ is H, X is NH, Y is Me and $R^1$ is 3-quinolin-4-yl-propyl;

$R^2$ is H, $R^3$ is H, $R^4$ is H, X is NH, Y is Me and $R^1$ is 3-(7-methoxy-quinolin-4-yl)-propyl;

$R^2$ is H, $R^3$ is H, $R^4$ is H, X is NH, Y is Me and $R^1$ is 3-benzoimidazol-1-yl-propyl;

$R^2$ is H, $R^3$ is H, $R^4$ is H, X is NH, Y is Me and $R^1$ is 3-indol-1-yl-propyl;

$R^2$ is H, $R^3$ is H, $R^4$ is H, X is NH, Y is Me and $R^1$ is 3-indazol-1-yl-propyl;

$R^2$ is H, $R^3$ is H, $R^4$ is H, X is NH, Y is Me and $R^1$ is 3-carbazol-1-yl-propyl;

$R^2$ is H, $R^3$ is H, $R^4$ is H, X is NH, Y is Me and $R^1$ is 3-(5-phenyl-1H-pyrrol-2-yl)-propy;

$R^2$ is H, $R^3$ is H, $R^4$ is H, X is NH, Y is Me and $R^1$ is 3-(4-phenyl-imidazol-1-yl)-propyl);

$R^2$ is H, $R^3$ is H, $R^4$ is H, X is NH, Y is Me and $R^1$ is 3-(3-(4-chlorophenyl)-(1,2,4)oxadizol-5-yl)-propyl;

$R^2$ is H, $R^3$ is H, $R^4$ is H, X is NH, Y is Me and $R^1$ is 3-(3-(4-methoxyphenyl)-(1,2,4)oxadizol-5-yl)-propyl;

$R^2$ is H, $R^3$ is H, $R^4$ is H, X is NH, Y is Me and $R^1$ is 3-(3-(4-pyridin4-yl)-(1,2,4)-yl)oxadizol-5-yl)-propyl;

R² is H, R³ is H, R⁴ is H, X is NH, Y is Me and R¹ is 3-benzotrizol-1-yl-propyl;

R² is H, R³ is H, R⁴ is H, X is NH, Y is Me and R¹ is 3-pyridin-4-yl-propyl;

R² is H, R³ is H, R⁴ is H, X is NH, Y is Me and R¹ is 3-(2-pyridin-3-yl-thiazol-4-yl)-propyl;

R² is H, R³ is H, R⁴ is H, X is NH, Y is Me and R¹ is 3-(2-phenyl-thiazol-5-yl)-propyl; or R² is H, R³ is H, R⁴ is H, X is NH, Y is Me and R¹ is 3-(4-phenyl-1H-imidazol-2-yl)-propyl.

11. The compound of claim 3 wherein:

R² is H, R³ is H, X is NH, Y is Me and R¹ is 3-(imidazo(4,5-b)pyridin-3-yl)-propyl;

R² is H, R³ is H, X is NH, Y is Me and R¹ is 3-(4-pyridin-3-yl-imidazol-1-yl)-propyl;

R² is H, R³ is H, X is NH, Y is Me and R¹ is 3-quinolin-4-yl-propyl;

R² is H, R³ is H, X is NH, Y is Me and R¹ is 3-(7-methoxy-quinolin-4-yl)-propyl;

R² is H, R³ is H, X is NH, Y is Me and R¹ is 3-benzoimidazol-1-yl-propyl;

R² is H, R³ is H, X is NH, Y is Me and R¹ is 3-indol-1-yl-propyl;

R² is H, R³ is H, X is NH, Y is Me and R¹ is 3-indazol-1-yl-propyl;

R² is H, R³ is H, X is NH, Y is Me and R¹ is 3-(5-phenyl-1H-pyrrol-2-yl)-propyl;

R² is H, R³ is H, X is NH, Y is Me and R¹ is 3-(4-phenyl-imidazol-1-yl)-propyl);

R² is H, R³ is H, X is NH, Y is Me and R¹ is 3-(3-(4-chlorophenyl)-(1,2,4)oxadizol-5-yl)-propyl;

R² is H, R³ is H, X is NH, Y is Me and R¹ is 3-(3-(4-methoxyphenyl)-(1,2,4)oxadizol-5-yl)-propyl;

R² is H, R³ is H, X is NH, Y is Me and R¹ is 3-(3-(4-pyridin-4-yl)-(1,2,4)oxadizol-5-yl)-propyl;

R² is H, R³ is H, X is NH, Y is Me and R¹ is 3-benzotrizol-1-yl-propyl;

R² is H, R³ is H, X is NH, Y is Me and R¹ is 3-pyridin-4-yl-propyl;

R² is H, R³ is H, X is NH, Y is Me and R¹ is 3-(2-pyridin-3-yl-thiazol-4-yl)-propyl;

R² is H, R³ is H, X is NH, Y is Me and R¹ is 3-(2-phenyl-thiazol-5-yl)-propyl; or R² is H, R³ is H, X is NH, Y is Me and R¹ is 3-(4-phenyl-1H-imidazol-2-yl)-propyl.

12. The compound of claim 4 wherein:

R² is H, R³ is H, R⁴ is H, X is NH, Y is Me and R¹ is 3-(imidazo(4,5-b)pyridin-3-yl)-propyl;

R² is H, R³ is H, R⁴ is H, X is NH, Y is Me and R¹ is 3-(4-pyridin-3-yl-imidazol-1-yl)-propyl;

R² is H, R³ is H, R⁴ is H, X is NH, Y is Me and R¹ is 3-benzoimidazol-1-yl-propyl;

R² is H, R³ is H, R⁴ is H, X is NH, Y is Me and R¹ is 3-benzoimidazol-1-yl-propyl;

R² is H, R³ is H, R⁴ is H, X is NH, Y is Me and R¹ is 3-indol-1-yl-propyl;

R² is H, R³ is H, R⁴ is H, X is NH, Y is Me and R¹ is 3-imidazol-1-yl-propyl;

R² is H, R³ is H, R⁴ is H, X is NH, Y is Me and R¹ is 3-(5-phenyl-1H-pyrrol-2-yl)-propyl;

R² is H, R³ is H, R⁴ is H, X is NH, Y is Me and R¹ is 3-(4-phenyl-imidazol-1-yl)-propyl);

R² is H, R³ is H, R⁴ is H, X is NH, Y is Me and R¹ is 3-(3-(4chlorophenyl)-(1,2,4)oxadizol-5-yl)-propyl;

R² is H, R³ is H, R⁴ is H, X is NH, Y is Me and R¹ is 3-(3-(4-methoxyphenyl)-(1,2,4)oxadizol-5-yl-propyl;

R² is H, R³ is H, R⁴ is H, X is NH, Y is Me and R¹ is 3-(3-(4-pyridin-4-yl)-(1,2,4)oxadizol-5-yl)-propyl;

R² is H, R³ is H, R⁴ is H, X is NH, Y is Me and R¹ is 3-benzotrizol-1-yl-propyl;

R² is H, R³ is H, R⁴ is H, X is NH, Y is Me and R¹ is 3-pyridin-4-yl-propyl;

R² is H, R³ is H, R⁴ is H, X is NH, Y is Me and R¹ is 3-(2-pyridin-3-yl-thiazol-4-yl)-propyl;

R² is H, R³ is H, R⁴ is H, X is NH, Y is Me and R¹ is 3-(2-phenyl-thiazol-5-yl)-propyl; or R² is H, R³ is H, R⁴ is H, X is NH, Y is Me and R¹ is 3-(4-phenyl-1H-imidazol-2-yl)-propyl.

13. The compound of claim 5 wherein:

Z is H, R³ is H, X is NH, R² is H or Me, Y is Me and R¹ is 3-(imidazo(4,5-b)pyridin-3-yl)-propyl;

Z is H, R³ is H, X is NH, R² is H or Me, Y is Me, R² is H or Me and R¹ is 3-(4-pyridin-3-yl-imidazol-1-yl)-propyl;

Z is H, R³ is H, X is NH, R² is H or Me, Y is Me, R² is H or Me and R¹ is 3-quinolin-4-yl-propyl;

Z is H, R³ is H, X is NH, R² is H or Me, Y is Me, R² is H or Me and R¹ is 3-(7-methoxy-quinolin-4-yl)-propyl;

Z is H, R³ is H, X is NH, Y is Me, R² is H or Me and R¹ is 3-benzoimidazol-1-yl-propyl;

Z is H, R³ is H, X is NH, Y is Me, R² is H or Me and R¹ is 3-indol-1-yl-propyl;

Z is H, R³ is H, X is NH, Y is Me, R² is H or Me and R¹ is 3-indazol-1-yl-propyl;

Z is H, R³ is H, X is NH, Y is Me, R² is H or Me and R¹ is 3-carbazol-1-yl-propyl;

Z is H, R³ is H, X is NH, Y is Me, R² is H or Me and R¹ is 3-(5-phenyl-1H-pyrrol-2-yl)-propyl;

Z is H, R³ is H, X is NH, Y is Me, R² is H or Me and R¹ is 3-(4-phenyl-imidazol-1-yl)-propyl);

Z is H, R³ is H, X is NH, Y is Me, R² is H or Me and R¹ is 3-(3-(4-chlorophenyl)-(1,2,4)oxadizol-5-yl)-propyl;

R² is H, R³ is H, X is NH, Y is Me, R² is H or Me and R¹ is 3-(3-(4-methoxyphenyl)-(1,2,4)oxadizol-5-yl)-propyl;

R² is H, R³ is H, X is NH, Y is Me, R² is H or Me and R¹ is 3-(3-(4-pyridin-4-yl)-(1,2,4)oxadizol-5-yl)-propyl;

R² is H, R³ is H, X is NH, Y is Me, R² is H or Me and R¹ is 3-benzotrizol-1-yl-propyl;

Z is H, R³ is H, X is NH, Y is Me, R² is H or Me and R¹ is 3-pyridin-4-yl-propyl;

Z is H, R³ is H, X is NH, Y is Me, R² is H or Me and R¹ is 3-(2-pyridin-3-yl-thiazol-4-yl)-propyl;

Z is H, R³ is H, X is NH, Y is Me, R² is H or Me and R¹ is 3-(2-phenyl-thiazol-5-yl)-propyl; or Z is H, R³ is H, X is NH, R² is H or Me, Y is Me and R¹ is 3-(4-phenyl-1H-imidazol-2-yl)-propyl.

14. The compound of claim 6 wherein:

Z is H, R³ is H, R⁴ is H, X is NH, R² is H or Me, Y is Me and R¹ is 3-(imidazo(4,5-b)pyridin-3-yl)-propyl;

Z is H, R³ is H, R⁴ is H, X is NH, R² is H or Me, Y is Me, R² is H or Me and R¹ is 3-(4-pyridin-3-yl-imidazol-1-yl)-propyl;

Z is H, R³ is H, R⁴ is H, X is NH, R² is H or Me, Y is Me, R² is H or Me and R¹ is 3-quinolin-4-yl-propyl;

Z is H, R³ is H, R⁴ is H, X is NH, R² is H or Me, Y is Me, R² is H or Me and R¹ is 3-(7-methoxy-quinolin-4-yl)-propyl;

Z is H, R³ is H, R⁴ is H, X is NH, Y is Me, R² is H or Me and R¹ is 3-benzoimidazol-1-yl-propyl;

Z is H, R³ is H, R⁴ is H, X is NH, Y is Me, R² is H or Me and R¹ is 3-indol-1-yl-propyl;

Z is H, R³ is H, R⁴ is H, X is NH, Y is Me, R² is H or Me and R¹ is 3-indazol-1-yl-propyl;

Z is H, R³ is H, R⁴ is H, X is NH, Y is Me, R² is H or Me and R¹ is 3-carbazol-1-yl-propyl;

Z is H, R³ is H, R⁴ is H, X is NH, Y is Me, R² is H or Me and R¹ is 3-(5-phenyl-1H-pyrrol-2-yl)-propyl;

Z is H, R³ is H, R⁴ is H, X is NH, Y is Me, R² is H or Me and R¹ is 3-(4-phenyl-imidazol-1-yl)-propyl);

Z is H, R³ is H, R⁴ is H, X is NH, Y is Me, R² is H or Me and R¹ is 3-(3-(4-chlorophenyl)-(1,2,4)oxadizol-5-yl)-propyl;

R² is H, R³ is H, R⁴ is H, X is NH, Y is Me, R² is H or Me and R¹ is 3-(3-(4-methoxyphenyl)-(1,2,4)oxadizol-5-yl)-propyl;

R² is H, R³ is H, R⁴ is H, X is NH, Y is Me, R² is H or Me and R¹ is 3-(3-(4-pyridin-4-yl)-(1,2,4)oxadizol-5-yl)-propyl;

R² is H, R³ is H, R⁴ is H, X is NH, Y is Me, R² is H or Me and R¹ is 3-benzotrizol-1-yl-propyl;

Z is H, R³ is H, R⁴ is H, X is NH, Y is Me, R² is H or Me and R¹ is 3-pyridin-4-yl-propyl;

Z is H, R³ is H, R⁴ is H, X is NH, Y is Me, R² is H or Me and R¹ is 3-(2-pyridin-3-yl-thiazol-4-yl)-propyl;

Z is H, R³ is H, R⁴ is H, X is NH, Y is Me, R² is H or Me and R¹ is 3-(2-phenyl-thiazol-5-yl)-propyl; or Z is H, R³ is H, R⁴ is H, X is NH, R² is H or Me, Y is Me and R¹ is 3-(4-phenyl-1H-imidazol-2-yl)-propyl.

15. The compound of claim 7 wherein:

Z is H, R³ is H, X is NH, R² is H or Me, Y is Me and R¹ is 3-(imidazo(4,5-b)pyridin-3-yl)-propyl;

Z is H, R³ is H, X is NH, R² is H or Me, Y is Me, R² is H or Me and R¹ is 3-(4-pyridin-3-yl-imidazol-1-yl)-propyl;

Z is H, R³ is H, X is NH, R² is H or Me, Y is Me, R² is H or Me and R¹ is 3-quinolin-4-yl-propyl;

Z is H, R³ is H, X is NH, R² is H or Me, Y is Me, R² is H or Me and R¹ is 3-(7-methoxy-quinolin-4-yl)-propyl;

Z is R³ is H, X is NH, Y is Me, R² is H or Me and R¹ is 3-benzoimidazol-1-yl-propyl;

Z is R³ is H, X is NH, Y is Me, R² is H or Me and R¹ is 3-indol-1-yl-propyl;

Z is R³ is H, X is NH, Y is Me, R² is H or Me and R¹ is 3-indazol-1-yl-propyl;

Z is R³ is H, X is NH, Y is Me, R² is H or Me and R¹ is 3-carbazol-1-yl-propyl;

Z is R³ is H, X is NH, Y is Me, R² is H or Me and R¹ is 3-(5-phenyl-1H-pyrrol-2-yl)-propyl;

Z is R³ is H, X is NH, Y is Me, R² is H or Me and R¹ is 3-(4-phenyl-imidazol-1-yl)propyl);

Z is R³ is H, X is NH, Y is Me, R² is H or Me and R¹ is 3-(3-(4-chlorophenyl)-(1,2,4)oxadizol-5-yl)-propyl;

R² is H, R³ is H, X is NH, Y is Me, R² is H or Me and R¹ is 3-(3-(4-methoxyphenyl)-(1,2,4)oxadizol-5-yl)-propyl;

R² is H, R³ is H, X is NH, Y is Me, R² is H or Me and R¹ is 3-(3-(4-pyridin-4-yl)-(1,2,4)oxadizol-5-yl)-propyl;

Z is R³ is H, X is NH, Y is Me, R² is H or Me and R¹ is 3-benzotrizol-1-yl-propyl;

Z is R³ is H, X is NH, Y is Me, R² is H or Me and R¹ is 3-pyridin-4-yl-propyl;

Z is R³ is H, X is NH, Y is Me, R² is H or Me and R¹ is 3-(2-pyridin-3-yl-thiazol4-yl)-propyl;

Z is R³ is H, X is NH, Y is Me, R² is H or Me and R¹ is 3-(2-phenyl-thiazol-5-yl)-propyl; or Z is R³ is H, X is NH, R² is H or Me, Y is Me and R¹ is 3-(4-phenyl-1H-imidazol-2-yl)-propyl.

16. The compound of claim 8 wherein:

Z is H, R³ is H, R⁴ is H, X is NH, R² is H or Me, Y is Me and R¹ is 3-(imidazo(4,5-b)pyridin-3-yl)-propyl;

Z is H, R³ is H, R⁴ is H, X is NH, R² is H or Me, Y is Me, R² is H or Me and R¹ is 3-(4-pyridin-3-yl-imidazol-1-yl)-propyl;

Z is H, R³ is H, R⁴ is H, X is NH, R² is H or Me, Y is Me, R² is H or Me and R is 3-quinolin-4-yl-propyl;

Z is H, R³ is H, R⁴ is H, X is NH, R² is H or Me, Y is Me, R² is H or Me and R¹ is 3-(7-methoxy-quinolin-4-yl)-propyl;

Z is H, R³ is H, R⁴ is H, X is NH, Y is Me, R² is H or Me and R¹ is 3-benzoimidazol-1-yl-propyl;

Z is H, R³ is H, R⁴ is H, X is NH, Y is Me, R² is H or Me and R¹ is 3-indol-1-yl-propyl;

Z is H, R³ is H, R⁴ is H, X is NH, Y is Me, R² is H or Me and R¹ is 3-indazol-1-yl-propyl;

Z is H, R³ is H, R⁴ is H, X is NH, Y is Me, R² is H or Me and R¹ is 3-carbazol-1-yl-propyl;

Z is R³ is H, R⁴ is H, X is NH, Y is Me, R² is H or Me and R¹ is 3-(5-phenyl-1H-pyrrol-2-yl)-propyl;

Z is R³ is H, R⁴ is H, X is NH, Y is Me, R² is H or Me and R¹ is 3-(4-phenyl-imidazol-1-yl)-propyl);

Z is R³ is H, R⁴ is H, X is NH, Y is Me, R² is H or Me and R¹ is 3-(3-(4-chlorophenyl)-(1,2,4)oxadizol-5-yl)-propyl;

R² is H, R³ is H, R⁴ is H, X is NH, Y is Me, R² is H or Me and R¹ is 3-(3-(4-methoxyphenyl)-(1,2,4)oxadizol-5-yl)-propyl;

R² is H, R³ is H, R⁴ is H, X is NH, Y is Me, R² is H or Me and R¹ is 3-(3-(4-pyridin-4-yl)-(1,2,4)oxadizol-5-yl)-propyl;

R² is H, R³ is H, R⁴ is H, X is NH, Y is Me, R² is H or Me and R¹ is 3-benzotrizol-1-yl-propyl;

Z is H, R³ is H, R⁴ is H, X is NH, Y is Me, R² is H or Me and R¹ is 3-pyridin-4-yl-propyl;

Z is H, R³ is H, R⁴ is H, X is NH, Y is Me, R² is H or Me and R¹ is 3-(2-pyridin-3-yl-thiazol-4-yl)-propyl;

Z is H, R³ is H, R⁴ is H, X is NH, Y is Me, R² is H or Me and R¹ is 3-(2-phenyl-thiazol-5-yl)-propyl; or Z is H, R³ is H, R⁴ is H, X is NH, R² is H or Me, Y is Me and R¹ is 3-(4-phenyl-1H-imidazol-2-yl)-propyl.

17. A pharmaceutical composition for the treatment of an infection in a mammal, fish or bird which comprises a therapeutically effective amount of a the compound of claims 1, 2, 3, 4, 5, 6, 7 or 8 and a pharmaceutically acceptable carrier.

18. A method of treating an infection in a mammal, fish, or bird which comprises administering to said mammal, fish, or bird a therapeutically effective amount of a the compound of claims 1, 2, 3, 4, 5, 6, 7 or 8.

19. A method of preparing a compound according to claim 1 which comprises treating a compound of the formula 9

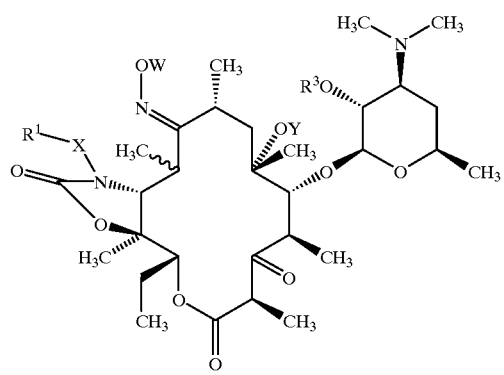

9

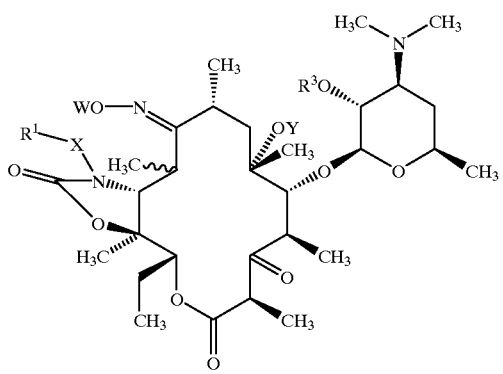

11 wherein X, Y, R¹ and R³ are as defined for the compound of formula 1 in claim 1 and wherein W is a tosyl or a mesyl group, with $PCl_5$ or an acid, to form the compound of formula 1.

20. The method of claim 19 wherein the acid is selected from the group consisting of $H_2SO_4$, formic acid, hydrochloric acid and methanesulfonic acid.

21. A method of preparing a compound according to claim 2 which comprises treating a compound of the formula 10

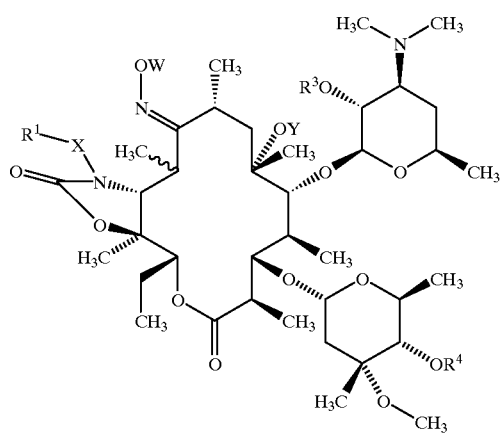

10 wherein X, Y, R¹, R³ and R⁴ are as defined for the compound of formula 2 in claim 2 and wherein W is a tosyl or a mesyl group, with $PCl_5$ or an acid, to form the compound of formula 2.

22. The method of claim 21 wherein the acid is selected from the group consisting of: $H_2SO_4$, formic acid, hydrochloric acid and methanesulfonic acid.

23. A method of preparing a compound according to claim 3 which comprises treating a compound of the formula 11 wherein X, Y, R¹ and R³ are as defined for the compound of formula 3 in claim 3, and wherein W is a tosyl or a mesyl group, with $PCl_5$ or an acid to form the compound of formula 3.

24. The method of claim 23 wherein the acid is selected from the group consisting of: $H_2SO_4$, formic acid, hydrochloric acid and methanesulfonic acid.

25. A method of preparing a compound according to claim 4 which comprises treating a compound of the formula 12

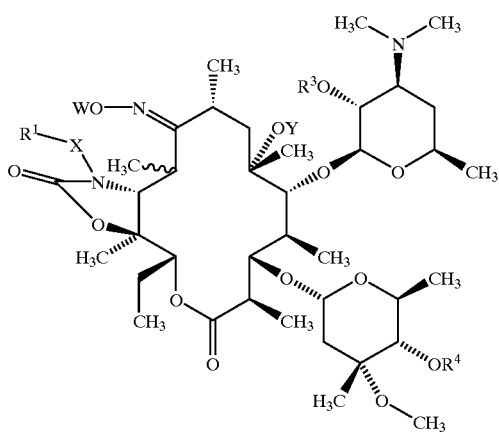

12 wherein X, Y, R¹, R³ and R⁴ are as defined for the compound of formula 4 in claim 4 and wherein W is a tosyl or a mesyl group, with $PCl_5$ or an acid to form the compound of formula 4.

26. The method of claim 25 wherein the acid is selected from the group consisting of: $H_2SO_4$, formic acid, hydrochloric acid and methanesulfonic.

27. A method of preparing a compound according to claim 5 which comprises treating a compound of the formula 9

9

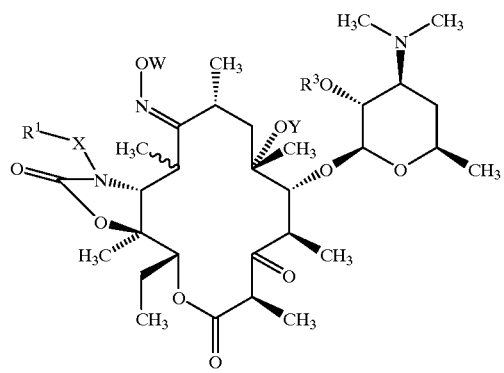

wherein X, Y, $R^1$ and $R^3$ are as defined for the compound of formula 5 in claim 5 and wherein W is a tosyl or a mesyl group, with a compound of the formula $Z_3Al$, wherein Z is defined for the compound of formula 5 to form the compound of formula 5.

28. A method of preparing a compound according to claim 6 which comprises treating a compound of the formula 10

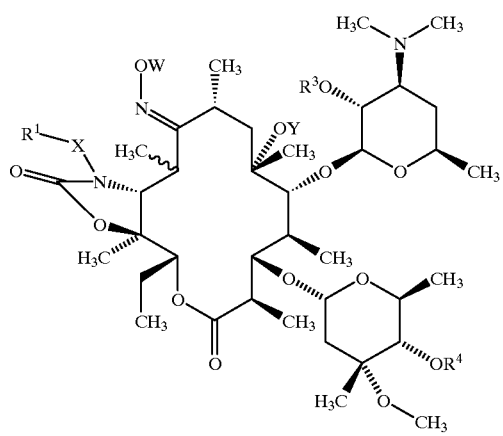

wherein X, Y, $R^1$, $R^3$ and $R^4$ are as defined for the compound of formula 6 in claim 6 and wherein W is a tosyl or a mesyl group, with a compound of the formula $Z_3Al$, wherein Z is defined for the compound of formula 6 to form the compound of formula 6.

29. A method of preparing a compound according to claim 7 which comprises treating a the compound of the formula 11

11

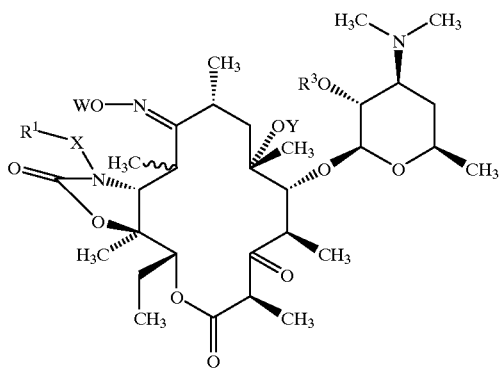

wherein X, Y, $R^1$ and $R^3$ are as defined for the compound of formula 7 in claim 7 and wherein W is a tosyl or a mesyl group, with a compound of the formula $Z_3Al$, where Z is defined for the compound of 7 to form the compound of formula 7.

30. A method of preparing a compound according to claim 8 which comprises treating a compound of the formula 12

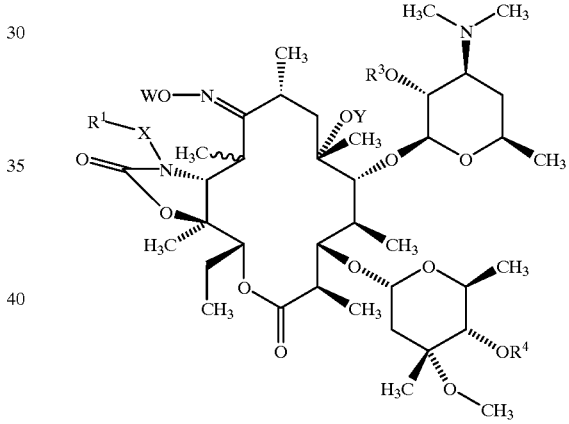

wherein X, Y, $R^1$, $R^3$ and $R^4$ are as defined for the compound of formula 8 in claim 8 and wherein W is a tosyl or a mesyl group, with a compound of the formula $Z_3Al$, wherein Z is as defined for the compound of formula 8, to form the compound of formula 8.

* * * * *